(12) United States Patent
Jung et al.

(10) Patent No.: US 10,889,583 B2
(45) Date of Patent: Jan. 12, 2021

(54) PESTICIDALLY ACTIVE HETEROCYCLIC DERIVATIVES WITH SULPHUR AND HYDROXYLAMINE SUBSTITUENTS

(71) Applicant: Syngenta Participations AG, Basel (CH)

(72) Inventors: Pierre Joseph Marcel Jung, Stein (CH); Vikas Sikervar, Ilhas (IN); Indira Sen, Ilhas (IN); Girish Rawal, Ilhas (IN); Michel Muehlebach, Stein (CH); Andrew Edmunds, Stein (CH); Sebastian Rendler, Stein (CH); Daniel Emery, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/345,709

(22) PCT Filed: Sep. 28, 2017

(86) PCT No.: PCT/EP2017/074590
§ 371 (c)(1),
(2) Date: Apr. 27, 2019

(87) PCT Pub. No.: WO2018/077565
PCT Pub. Date: May 3, 2018

(65) Prior Publication Data
US 2019/0352299 A1 Nov. 21, 2019

(30) Foreign Application Priority Data

Oct. 27, 2016 (IN) .............................. 201611036908

(51) Int. Cl.
*C07D 471/04* (2006.01)
*A01N 43/90* (2006.01)
(52) U.S. Cl.
CPC ............ *C07D 471/04* (2013.01); *A01N 43/90* (2013.01)
(58) Field of Classification Search
CPC .................................................. C07D 471/04

USPC ......................................................... 514/303
See application file for complete search history.

(56) References Cited

U.S. PATENT DOCUMENTS

| 10,005,775 | B2 * | 6/2018 | Jung | ...................... A01N 43/90 |
| 10,323,031 | B2 * | 6/2019 | Jung | .................... C07D 471/04 |
| 2018/0354942 | A1 * | 12/2018 | Jung | .................... C07D 471/04 |

FOREIGN PATENT DOCUMENTS

| WO | 2016023954 A2 | 2/2016 |
| WO | 2016142326 A1 | 9/2016 |
| WO | 2017001314 A1 | 1/2017 |

OTHER PUBLICATIONS

Kocevar, Heterocycles (1990), 30(1, Spec. Issue), 227-30.*
Dorwald F. A. Side Reactions in Organic Synthesis, 2005, Wiley: VCH, Weinheim p. IX of Preface p. 1-15.*
Kelly, Chem. Commun., 2013, 49, 11133.*
ISR & WrOp for PCT/EP2017/074590, dated Dec. 13, 2017.

* cited by examiner

*Primary Examiner* — Nizal S Chandrakumar
(74) *Attorney, Agent, or Firm* — Baker & Hostetler LLP; Toni-Junell Herbert

(57) ABSTRACT

Compounds of formula (I) wherein the substituents are as defined in claim 1, and the agrochemically acceptable salts, stereoisomers, enantiomers, tautomers and N-oxides of those compounds, can be used as insecticides and can be prepared in a manner known per se.

7 Claims, No Drawings

PESTICIDALLY ACTIVE HETEROCYCLIC DERIVATIVES WITH SULPHUR AND HYDROXYLAMINE SUBSTITUENTS

CROSS-REFERENCE TO RELATED APPLICATIONS

This application is a 371 National Stage application of International Application No. PCT/EP2017/074590, filed Sep. 28, 2017, which claims priority to European Application No. 201611036908 filed Oct. 27, 2016, the entire contents of which applications are hereby incorporated by reference.

The present invention relates to pesticidally active, in particular insecticidally active heterocyclic derivatives containing sulphur substituents, to compositions comprising those compounds, and to their use for controlling animal pests (including arthropods and in particular insects or representatives of the order Acarina).

Heterocyclic compounds with pesticidal action are known and described, for example, in WO 2012/086848, WO 2013/018928 and WO 2016/023954.

There have now been found novel pesticidally active heterocyclic derivatives with sulphur containing phenyl and pyridyl substituents.

The present invention accordingly relates to compounds of formula I,

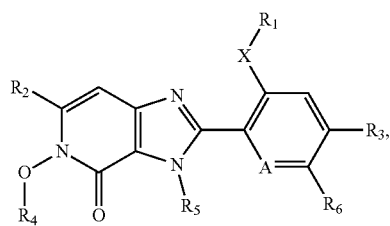

(I)

wherein
A is CH or N;
X is S, SO, $SO_2$ or SO(NH);
$R_1$ is $C_1$-$C_6$alkyl, $C_1$-$C_6$ haloalkyl, $C_1$-$C_4$alkyl-$C_3$-$C_6$cycloalkyl, $C_3$-$C_6$halocycloalkyl, $C_1$-$C_4$alkyl-$C_3$-$C_6$halocycloalkyl, $C_2$-$C_6$alkenyl, $C_2$-$C_6$haloalkenyl, $C_2$-$C_6$alkynyl or $C_2$-$C_6$ haloalkynyl; or
$R_1$ is $C_3$-$C_6$cycloalkyl which can be mono- or polysubstituted by substituents selected from the group consisting of halogen, cyano, $C_1$-$C_4$haloalkyl and $C_1$-$C_4$alkyl;
$R_2$ is cyano, $C_1$-$C_6$haloalkyl, $C_1$-$C_6$haloalkoxy, $C_1$-$C_4$haloalkylsulfanyl, $C_1$-$C_4$haloalkylsulfinyl or $C_1$-$C_4$haloalkylsulfonyl; or
$R_2$ is $C_3$-$C_6$cycloalkyl which can be mono- or polysubstituted by substituents selected from the group consisting of halogen, cyano, $C_1$-$C_4$haloalkyl, $C_1$-$C_4$alkoxy and $C_1$-$C_4$alkyl;
$R_4$ is hydrogen, $C_1$-$C_6$alkyl, $C_1$-$C_6$ haloalkyl, $C_2$-$C_6$alkenyl, $C_2$-$C_6$haloalkenyl, $C_2$-$C_6$alkynyl or $C_2$-$C_6$ haloalkynyl; or
$R_4$ is $C_3$-$C_6$cycloalkyl which can be mono- or polysubstituted by substituents selected from the group consisting of halogen, cyano, $C_1$-$C_4$haloalkyl, $C_1$-$C_4$alkoxy and $C_1$-$C_4$alkyl; or
$R_4$ is $C_1$-$C_4$alkyl mono- or polysubstituted by substituents selected from the group consisting of halogen, cyano, $C_3$-$C_6$cycloalkyl, phenyl, pyridyl, pyrimidinyl, $C_1$-$C_4$ alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl and $C_1$-$C_4$alkoxy;
$R_3$ and $R_6$ are independently hydrogen, halogen, cyano, $C_1$-$C_6$alkyl, $C_1$-$C_6$haloalkyl, $C_1$-$C_6$alkoxy, $C_1$-$C_6$haloalkoxy, $C_1$-$C_6$alkylsulfanyl, $C_1$-$C_6$haloalkylsulfanyl, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $R_7R_8N$—, hydroxyl, $C_2$-$C_6$alkenyl, $C_2$-$C_6$haloalkenyl, $C_2$-$C_6$alkynyl, $C_2$-$C_6$haloalkynyl, —$SF_5$ or —$N=S(O)_pR_9R_{10}$; or
$R_3$ and $R_6$ are independently $C_3$-$C_6$cycloalkyl which can be mono- or polysubstituted by substituents selected from the group consisting of halogen, $C_1$-$C_4$alkyl, $C_1$-$C_4$haloalkyl, cyano and $C_1$-$C_4$alkoxy; or
$R_3$ and $R_6$ are independently $C_1$-$C_4$alkyl-$C_3$-$C_6$cycloalkyl which can be mono- or polysubstituted by substituents selected from the group consisting of halogen, $C_1$-$C_4$alkyl, $C_1$-$C_4$haloalkyl and cyano; or
$R_3$ and $R_6$ are independently $C_1$-$C_4$alkyl mono- or polysubstituted by substituents selected from the group consisting of halogen, cyano, $C_1$-$C_4$alkoxy, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $R_7R_8N$— and hydroxyl; or
$R_3$ and $R_6$ are independently a five- to six-membered aromatic ring system, linked via a carbon atom to the ring which contains the substituent A, said ring system can be mono- or polysubstituted by substituents selected from the group consisting of halogen, cyano, nitro, $C_1$-$C_4$alkyl, $C_2$-$C_6$alkenyl, $C_2$-$C_6$haloalkenyl, $C_2$-$C_6$alkynyl, $C_2$-$C_6$haloalkynyl, $C_1$-$C_4$alkoxy-$C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —$C(O)C_1$-$C_4$alkyl, $C_1$-$C_4$haloalkylsulfanyl, $C_1$-$C_4$haloalkylsulfinyl, $C_1$-$C_4$haloalkylsulfonyl, $R_7R_8N$—, hydroxyl and —$C(O)C_1$-$C_4$haloalkyl; and said ring system can contain 1, 2 or 3 heteroatoms selected from the group consisting of nitrogen, oxygen and sulphur, where said ring system may not contain more than one oxygen atom and not more than one sulfur atom; or
$R_3$ and $R_6$ are independently a five-membered aromatic ring system linked via a nitrogen atom to the ring which contains the substituent A, said ring system can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —$C(O)C_1$-$C_4$alkyl, $C_1$-$C_4$haloalkylsulfanyl, $C_1$-$C_4$haloalkylsulfinyl, $C_1$-$C_4$haloalkylsulfonyl, $R_7R_8N$—, hydroxyl and —$C(O)$ $C_1$-$C_4$haloalkyl; and said ring system contains 1, 2 or 3 heteroatoms selected from the group consisting of nitrogen, oxygen and sulphur, where said ring system may not contain more than one oxygen atom and not more than one sulfur atom;
$R_5$ is $C_1$-$C_6$alkyl; or
$R_5$ is $C_1$-$C_4$alkyl mono- or polysubstituted by substituents selected from the group consisting of halogen, cyano, $C_1$-$C_4$ alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl and $C_1$-$C_4$alkoxy;
$R_7$ and $R_8$ are independently hydrogen, cyano, $C_2$-$C_4$ alkenyl, $C_2$-$C_4$haloalkenyl, $C_2$-$C_4$alkynyl, $C_2$-$C_4$haloalkynyl, $C_1$-$C_4$alkoxy-$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl, —C(O)$C_1$-$C_4$haloalkyl; or $R_7$ and $R_8$ are independently —C(O)$C_3$-$C_6$cycloalkyl wherein the $C_3$-$C_6$cycloalkyl can be mono- to polysubstituted by substituents selected from the group consisting of halogen, cyano, $C_1$-$C_4$haloalkyl and $C_1$-$C_4$alkyl; or $R_7$ and $R_8$ are independently $C_3$-$C_6$cycloalkyl which can be mono- to polysubstituted by substituents selected from the group consisting of halogen, cyano, $C_1$-$C_4$ haloalkyl and $C_1$-$C_4$alkyl;

$R_9$ and $R_{10}$ are independently $C_1$-$C_4$alkyl or $C_1$-$C_4$haloalkyl; or $R_9$ and $R_{10}$ are independently $C_3$-$C_6$cycloalkyl which can be mono- or polysubstituted by substituents selected from the group consisting of halogen, cyano, $C_1$-$C_4$ haloalkyl and $C_0$-$C_4$alkyl; and p is 0 or 1;

and agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals.

Haloalkoxy groups preferably have a chain length of from 1 to 6 carbon atoms. Haloalkoxy is, for example, difluoromethoxy, trifluoromethoxy or 2,2,2-trifluoroethoxy.

Alkoxyalkyl groups preferably have a chain length of 1 to 6 carbon atoms containing one or more oxygen atoms. Alkoxyalkyl is, for example, methoxymethyl, methoxyethyl, ethoxymethyl, ethoxyethyl, n-propoxymethyl, n-propoxyethyl, isopropoxymethyl, isopropoxyethyl or a dialkoxyalkyl derivative such as for example —$CH_2OCH_2CH_2OCH_3$.

Alkoxycarbonyl is for example methoxycarbonyl (which is Cialkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example cyclopropyl, cyclobutyl, cyclopentyl and cyclohexyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, di- or tri-substituted.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_2$-$C_4$alkynyl" and "$C_2$-$C_3$alkynyl" are to be construed accordingly. Examples of $C_2$-$C_6$ alkynyl include, but are not limited to, ethynyl, prop-1-ynyl, but-1-ynyl and but-2-ynyl.

As used herein, the term "$C_2$-$C_6$alkenyl" refers to a straight or branched hydrocarbon chain radical group consisting solely of carbon and hydrogen atoms, containing at least one double bond, having from two to six carbon atoms, and which is attached to the rest of the molecule by a single bond. The term "$C_2$-$C_4$alkenyl" and "$C_2$-$C_3$alkenyl" are to be defined accordingly. Examples of $C_2$-$C_6$alkenyl include, but are not limited to prop-1-enyl, but-1-enyl and but-2-enyl.

Alkylsulfanyl is for example methylsulfanyl, ethylsulfanyl, propylsulfanyl, isopropylsulfanyl, butylsulfanyl, pentylsulfanyl and hexylsulfanyl.

Alkylsulfinyl is for example methylsulfinyl, ethylsulfinyl, propylsulfinyl, isopropylsulfinyl, a butylsulfinyl, pentylsulfinyl or hexylsulfinyl.

Alkylsulfonyl is for example methylsulfonyl, ethylsulfonyl, propylsulfonyl, isopropylsulfonyl, butylsulfonyl, pentylsulfonyl or hexylsulfonyl.

Haloalkylsulfanyl is for example difluoromethylsulfanyl, trifluoromethylsulfanyl, 2, 2,2-trifluoroethylsulfanyl or pentafluoroethylsulfanyl.

Haloalkylsulfinyl is for example difluoromethylsulfinyl, trifluoromethylsulfinyl, 2, 2,2-trifluoroethylsulfinyl or pentafluoroethylsulfinyl.

Haloalkylsulfonyl is for example difluoromethylsulfonyl, trifluoromethylsulfonyl, 2, 2,2-trifluoroethylsulfonyl or pentafluoroethylsulfonyl.

In the context of this invention, examples of "five-membered aromatic ring system linked via a nitrogen atom to the ring which contains the substituent A" are, but are not limited to, pyrazolyl, imidazolyl, pyrrolyl, triazolyl and tetrazolyl. If said five-membered aromatic ring system contains more than one nitrogen atom, then it may be linked via any nitrogen atom to the ring which contains the substituent A.

In the context of this invention, examples of "five- to six-membered aromatic ring system, linked via a carbon atom to the ring which contains the substituent A" are, but are not limited to, phenyl, pyridyl, pyrimidyl, pyrrolyl, pyrazolyl, isoxazolyl, furanyl, thienyl, imidazolyl, oxazolyl, thiazolyl, isothiazolyl, triazolyl, oxadiazolyl, thiadiazolyl, tetrazolyl, furyl, pyrazinyl, pyridazinyl and triazinyl. Said five- to six-membered aromatic ring system may be linked via any carbon atom to the ring which contains the substituent A.

The compounds of formula I according to the invention also include hydrates which may be formed during the salt formation.

Free radicals represents methyl groups.

Preferred are compounds of formula I,
wherein
A is CH or N;
X is S, SO or $SO_2$;
$R_1$ is $C_1$-$C_6$alkyl;
$R_2$ is $C_1$-$C_6$haloalkyl, $C_1$-$C_6$haloalkoxy, $C_1$-$C_4$haloalkylsulfanyl, $C_1$-$C_4$haloalkylsulfinyl or $C_1$-$C_4$haloalkylsulfonyl;
$R_4$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl or $C_2$-$C_6$haloalkynyl; or
$R_4$ is $C_3$-$C_6$cycloalkyl which can be mono- or polysubstituted by substituents selected from the group consisting of halogen, cyano, $C_1$-$C_4$haloalkyl and $C_1$-$C_4$alkyl; or
$R_4$ is $C_1$-$C_4$alkyl mono- or polysubstituted by substituents selected from the group consisting of cyano, $C_3$-$C_6$cycloalkyl, phenyl, pyridine, pyrimidine, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl and $C_1$-$C_4$alkoxy;
$R_3$ and $R_6$ are independently hydrogen, halogen, cyano, $C_1$-$C_6$alkyl, $C_1$-$C_6$haloalkyl, $C_1$-$C_6$alkoxy, $C_1$-$C_6$haloalkoxy, $C_1$-$C_6$alkylsulfanyl, $C_1$-$C_6$haloalkylsulfanyl, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $R_7R_8N$—, hydroxyl, $C_2$-$C_6$alkenyl, $C_2$-$C_6$haloalkenyl, $C_2$-$C_6$alkynyl, $C_2$-$C_6$haloalkynyl, —$SF_5$ or —$N=S(O)_pR_9R_{10}$; or
$R_3$ and $R_6$ are independently $C_3$-$C_6$cycloalkyl which can be mono- or polysubstituted by substituents selected from the group consisting of halogen, $C_1$-$C_4$alkyl, $C_1$-$C_4$haloalkyl and cyano; or
$R_3$ and $R_6$ are independently $C_1$-$C_4$alkyl-$C_3$-$C_6$cycloalkyl which can be mono- or polysubstituted by substituents selected from the group consisting of halogen, $C_1$-$C_4$alkyl, $C_1$-$C_4$haloalkyl and cyano; or
$R_3$ and $R_6$ are $C_1$-$C_4$alkyl mono- or polysubstituted by substistuents selected from the group consisting of cyano, $C_1$-$C_4$alkoxy, $C_1$-$C_4$haloalkoxy, $C_1$-$C_4$ alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $R_7R_8N$— and hydroxyl; or
$R_3$ and $R_6$ are independently phenyl, pyridyl or pyrimidyl, all linked via a carbon atom to the ring which contains the substituent A, said phenyl, pyridyl or pyrimidyl can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —$C(O)C_1$-$C_4$alkyl, $C_1$-$C_4$haloalkylsulfanyl, $C_1$-$C_4$haloalkylsulfinyl, $C_1$-$C_4$haloalkylsulfonyl, $R_7R_8N$-hydroxyl and —$C(O)C_1$-$C_4$haloalkyl; or
$R_3$ and $R_6$ are independently triazolyl or pyrazolyl, both linked via a nitrogen atom to the ring which contains the substituent A, said triazolyl or pyrazolyl can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy $C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —$C(O)C_1$-$C_4$alkyl, $C_1$-$C_4$haloalkylsulfanyl, $C_1$-$C_4$haloalkylsulfinyl, $C_1$-$C_4$haloalkylsulfonyl, $R_7R_8N$-hydroxyl and —$C(O)C_1$-$C_4$haloalkyl;
$R_5$ is $C_1$-$C_6$alkyl;
$R_7$ and $R_8$ are independently hydrogen, cyano, $C_2$-$C_4$ alkenyl, $C_2$-$C_4$haloalkenyl, $C_2$-$C_4$alkynyl, $C_2$-$C_4$haloalkynyl, $C_1$-$C_4$alkoxy-$C_1$-$C_4$alkyl, $C_3$-$C_6$cycloalkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —$C(O)C_1$-$C_4$alkyl, $C_1$-$C_4$haloalkylsulfanyl, $C_1$-$C_4$haloalkylsulfinyl, $C_1$-$C_4$haloalkylsulfonyl or —$C(O)C_1$-$C_4$haloalkyl; or
$R_7$ and $R_8$ are independently —$C(O)C_3$-$C_6$cycloalkyl wherein the $C_3$-$C_6$cycloalkyl group can be mono- to polysubstituted by substituents selected from the group consisting of halogen, cyano, $C_1$-$C_4$haloalkyl and $C_1$-$C_4$alkyl;
$R_9$ and $R_{10}$ are independently $C_1$-$C_4$alkyl or $C_1$-$C_4$haloalkyl; or
$R_9$ and $R_{10}$ are independently $C_3$-$C_6$cycloalkyl which can be mono- or polysubstituted by substituents selected from the group consisting of halogen, cyano, $C_1$-$C_4$haloalkyl and $C_1$-$C_4$alkyl; and
p is 0 or 1.

Further preferred are compounds of formula I,
wherein
A is CH or N;
X is S, SO or $SO_2$;
$R_1$ is $C_1$-$C_6$alkyl;
$R_2$ is $C_1$-$C_6$haloalkyl, $C_1$-$C_4$haloalkylsulfanyl, $C_1$-$C_4$haloalkylsulfinyl, $C_1$-$C_4$haloalkylsulfonyl;
$R_4$ is hydrogen, $C_1$-$C_6$alkyl, $C_1$-$C_6$ haloalkyl, $C_2$-$C_6$alkenyl, $C_2$-$C_6$haloalkenyl, $C_2$-$C_6$alkynyl or $C_2$-$C_6$haloalkynyl; or
$R_4$ is $C_3$-$C_6$cycloalkyl which can be mono- or polysubstituted by substituents selected from the group consisting of halogen, cyano, $C_1$-$C_4$haloalkyl and $C_1$-$C_4$alkyl; or
$R_4$ is $C_1$-$C_4$alkyl mono- or polysubstituted by substituents selected from the group consisting of cyano, $C_3$-$C_6$cycloalkyl, phenyl, pyridyl, pyrimidinyl, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl and $C_1$-$C_4$alkoxy;
$R_3$ and $R_6$ are independently hydrogen, halogen, cyano, $C_1$-$C_6$alkyl, $C_1$-$C_6$haloalkyl, $C_1$-$C_6$alkoxy, $C_1$-$C_6$haloalkoxy, $C_1$-$C_6$alkylsulfanyl, $C_1$-$C_6$haloalkylsulfanyl, $C_1$-$C_6$alkylsulfinyl, $C_1$-$C_6$haloalkylsulfinyl, $C_1$-$C_6$alkylsulfonyl, $C_1$-$C_6$haloalkylsulfonyl, $R_7R_8N$— or —$N=S(O)_pR_9R_{10}$; or
$R_3$ and $R_6$ are independently $C_3$-$C_6$cycloalkyl which can be mono- or polysubstituted by substituents selected from the group consisting of halogen, $C_1$-$C_4$alkyl, $C_1$-$C_4$haloalkyl and cyano; or $R_3$ and $R_6$ are $C_1$-$C_4$alkyl mono- or polysubstituted by substituents selected from the group consisting of cyano, $C_1$-$C_4$alkoxy, $C_1$-$C_4$haloalkoxy, $C_1$-$C_4$ alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $R_7R_8N$— and hydroxyl; or $R_3$ and $R_6$ are independently phenyl, pyridyl or pyrimidyl, all linked via a carbon atom to the ring which contains the substituent A, said phenyl, pyridyl or pyrimidyl can be mono- or polysubstituted by substituents selected from the group consisting of halogen, cyano, $C_1$-$C_4$alkoxy $C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $R_7R_8N$— and hydroxyl; or $R_3$ and $R_6$ are independently triazolyl or pyrazolyl, both linked via a nitrogen atom to the ring which contains the substituent A, said triazolyl or pyrazolyl can be mono- or polysubstituted by substituents selected from the group consisting of halogen, cyano, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $R_7R_8N$— and hydroxyl;

$R_5$ is $C_1$-$C_6$alkyl;

$R_7$ and $R_8$ are independently hydrogen, cyano, $C_1$-$C_4$alkyl, cyclopropyl, $C_1$-$C_4$haloalkyl or $C_1$-$C_4$alkoxy; or $R_7$ and $R_8$ are independently —C(O)cyclopropyl which can be mono- or polysubstituted by substituents selected from the group consisting of halogen, cyano, $C_1$-$C_4$haloalkyl and $C_1$-$C_4$alkyl;

$R_9$ and $R_{10}$ are independently $C_1$-$C_4$alkyl or $C_1$-$C_4$haloalkyl; or $R_9$ and $R_{10}$ are independently cyclopropyl which can be mono- or polysubstituted by substituents selected from the group consisting of halogen, cyano, $C_1$-$C_4$haloalkyl and $C_1$-$C_4$alkyl; and p is 0 or 1.

Further preferred are compounds of formula I, wherein
A is CH or N;
X is S, SO or $SO_2$;
$R_1$ is $C_1$-$C_4$alkyl;
$R_2$ is $C_1$-$C_4$haloalkyl, $C_1$-$C_4$haloalkylsulfanyl, $C_1$-$C_4$haloalkylsulfinyl or $C_1$-$C_4$haloalkylsulfonyl;
$R_4$ is hydrogen, $C_1$-$C_6$alkyl or $C_1$-$C_6$ haloalkyl; or
$R_4$ is cyclopropyl which can be mono- or polysubstituted by substituents selected from the group consisting of halogen, cyano, $C_1$-$C_4$ haloalkyl and $C_0$-$C_4$alkyl; or
$R_4$ is $C_1$-$C_4$alkyl mono- or polysubstituted by substituents selected from the group consisting of cyano, cyclopropyl, phenyl, pyridyl, pyrimidinyl, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl and $C_1$-$C_4$alkoxy;

$R_3$ and $R_6$ are independently hydrogen, halogen, cyano, $C_1$-$C_6$alkyl, $C_1$-$C_6$haloalkyl, $C_1$-$C_6$alkoxy, $C_1$-$C_6$haloalkoxy or $R_7R_8N$—; or $R_3$ and $R_6$ are independently cyclopropyl which can be monosubstituted by cyano; or $R_3$ and $R_6$ are independently $C_1$-$C_4$alkyl which can be monosubstituted by cyano; or $R_3$ and $R_6$ are independently phenyl, pyridyl or pyrimidyl, all linked via a carbon atom to the ring which contains the substituent A, said phenyl, pyridyl or pyrimidyl can be mono- or polysubstituted by substituents selected from the group consisting of halogen, cyano, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $R_7R_8N$— and hydroxyl; or $R_3$ and $R_6$ are independently triazolyl or pyrazolyl, both linked via a nitrogen atom to the ring which contains the substituent A, said triazolyl or pyrazolyl can be mono- or polysubstituted by substituents selected from the group consisting of halogen, cyano, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $R_7R_8N$— and hydroxyl;

$R_5$ is $C_1$-$C_6$alkyl; and $R_7$ and $R_8$ are independently hydrogen, $C_1$-$C_4$alkyl, $C_1$-$C_4$haloalkyl, cyclopropyl, —C(O)cyclopropyl or $C_1$-$C_4$alkoxy.

Even further preferred are compounds of formula I, wherein
A is CH or N;
X is S, SO or $SO_2$;
$R_1$ is $C_1$-$C_4$alkyl;
$R_2$ is $C_1$-$C_4$haloalkyl, $C_1$-$C_4$haloalkylsulfanyl, $C_1$-$C_4$haloalkylsulfinyl or $C_1$-$C_4$haloalkylsulfonyl;
$R_4$ is hydrogen or $C_1$-$C_6$alkyl;
$R_3$ and $R_6$ are independently hydrogen, halogen, cyano, $C_1$-$C_6$alkyl, $C_1$-$C_6$haloalkyl, $C_1$-$C_6$alkoxy, $C_1$-$C_6$haloalkoxy or $R_7R_8N$—; or
$R_3$ and $R_6$ are independently cyclopropyl which can be monosubstituted by cyano; or
$R_3$ and $R_6$ are independently $C_1$-$C_4$alkyl which can be monosubstituted by cyano; or
$R_3$ and $R_6$ are independently phenyl, pyridyl or pyrimidyl, all linked via a carbon atom to the ring which contains the substituent A, said phenyl, pyridyl or pyrimidyl can be mono- or polysubstituted by substituents selected from the group consisting of halogen, cyano, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $R_7R_8N$— and hydroxyl; or
$R_3$ and $R_6$ are independently triazolyl or pyrazolyl, both linked via a nitrogen atom to the ring which contains the substituent A, said triazolyl or pyrazolyl can be mono- or polysubstituted by substituents selected from the group consisting of halogen, cyano, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $R_7R_8N$— and hydroxyl;
$R_5$ is $C_1$-$C_6$alkyl; and
$R_7$ and $R_8$ are independently hydrogen, $C_1$-$C_4$alkyl, $C_1$-$C_4$haloalkyl, cyclopropyl, —C(O)cyclopropyl or $C_1$-$C_4$alkoxy.

Even further preferred are compounds of formula I, wherein
A is CH or N;
X is S, SO or $SO_2$;
$R_1$ is $C_1$-$C_4$alkyl;
$R_2$ is $C_1$-$C_4$haloalkyl;
$R_4$ is hydrogen or $C_1$-$C_6$alkyl;
$R_3$ and $R_6$ are independently hydrogen, halogen, $C_1$-$C_6$haloalkyl or $R_7R_8N$—; or
$R_3$ and $R_6$ are independently cyclopropyl which can be monosubstituted by cyano; or
$R_3$ and $R_6$ are independently $C_1$-$C_4$alkyl which can be monosubstituted by cyano; or
$R_3$ and $R_6$ are independently triazolyl, linked via any nitrogen atom to the ring which contains the substituent A, said triazolyl can be monosubstituted by substituents selected from the group consisting of halogen and cyano;
$R_5$ is $C_1$-$C_6$alkyl; and
$R_7$ and $R_8$ are independently hydrogen, $C_1$-$C_4$alkyl, $C_1$-$C_4$haloalkyl, cyclopropyl, —C(O)cyclopropyl or $C_1$-$C_4$alkoxy.

Especially preferred are compounds of formula I, wherein
A is CH or N;
X is S, SO or $SO_2$, preferably S or $SO_2$;
$R_1$ is $C_1$-$C_4$alkyl, preferably methyl or ethyl;
$R_2$ is $C_1$-$C_4$haloalkyl, preferably trifluoromethyl;
$R_4$ is hydrogen or $C_1$-$C_6$alkyl, preferably hydrogen, methyl or ethyl, more preferably methyl;
$R_3$ and $R_6$ are independently hydrogen, halogen, $C_1$-$C_6$haloalkyl or $R_7R_8N$—; or
$R_3$ and $R_6$ are independently cyclopropyl which can be monosubstituted by cyano; or
$R_3$ and $R_6$ are independently $C_1$-$C_4$alkyl which can be monosubstituted by cyano; or
$R_3$ and $R_6$ are independently unsubstituted triazolyl, linked via any nitrogen atom to the ring which contains the substituent A;
$R_5$ is $C_1$-$C_6$alkyl, preferably methyl; and
$R_7$ and $R_8$ are independently hydrogen or $C_1$-$C_4$alkyl, preferably hydrogen or methyl, more preferably hydrogen;
and agrochemically acceptable salts, stereoisomers, enantiomers, tautomers and N-oxides of said especially preferred are compounds of formula I.

Further preferred are compounds of formula I represented by the compounds of formula I-10,

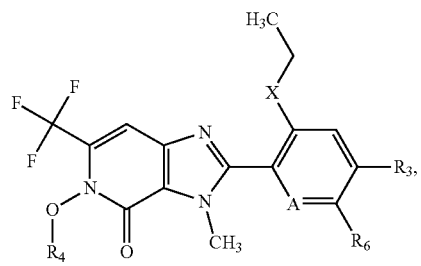

(I-10)

wherein
A is CH or N;
X is S, SO or $SO_2$;
$R_3$ and $R_6$ are independently hydrogen, halogen, cyano, $C_1$-$C_6$alkyl, $C_1$-$C_6$haloalkyl, $C_1$-$C_6$alkoxy or $R_7R_8N$—;
$R_4$ is hydrogen, $C_1$-$C_6$alkyl or $C_1$-$C_6$haloalkyl; or $R_4$ is cyclopropyl which can be mono- or polysubstituted by substituents selected from the group consisting of halogen, cyano, $C_1$-$C_4$haloalkyl and $C_1$-$C_4$alkyl; or
$R_4$ is $C_1$-$C_4$alkyl mono- or polysubstituted by substituents selected from the group consisting of cyano, cyclopropyl, phenyl, pyridyl, pyrimidinyl, $C_1$-$C_4$ alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl and $C_1$-$C_4$alkoxy;
$R_3$ and $R_6$ are independently cyclopropyl which can be monosubstituted by cyano; or
$R_3$ and $R_6$ are independently phenyl, pyridyl or pyrimidyl, all linked via a carbon atom to the ring which contains the substituent A, said phenyl, pyridyl or pyrimidyl can be mono- or polysubstituted by substituents selected from the group consisting of halogen, cyano, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $R_7R_8N$— and hydroxyl; or
$R_3$ and $R_6$ are independently triazolyl or pyrazolyl, both linked via a nitrogen atom to the ring which contains the substituent A, said triazolyl or pyrazolyl can be mono- or polysubstituted by substituents selected from the group consisting of halogen, cyano, $C_1$-$C_4$alkoxy $C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl, $C_1$-$C_4$haloalkylsulfonyl, $R_7R_8N$— and hydroxyl; and
$R_7$ and $R_8$ are independently hydrogen, $C_1$-$C_4$alkyl, $C_1$-$C_4$haloalkyl, cyclopropyl, —C(O)cyclopropyl or $C_1$-$C_4$alkoxy.

Further preferred are compounds of formula I-10, wherein
A is CH or N;
X is S, SO or $SO_2$;
$R_4$ is hydrogen, $C_1$-$C_6$alkyl or $C_1$-$C_6$haloalkyl;
$R_3$ and $R_6$ are independently hydrogen, halogen, cyano, $C_1$-$C_4$alkyl, $C_1$-$C_4$haloalkyl, $C_1$-$C_4$alkoxy or $R_7R_8N$—; or
$R_3$ and $R_6$ are independently cyclopropyl which can be monosubstituted by cyano; or
$R_3$ and $R_6$ are independently phenyl, pyridyl or pyrimidyl, all linked via a carbon atom to the ring which contains the substituent A, said phenyl, pyridyl or pyrimidyl can be mono- or polysubstituted by substituents selected from the group consisting of halogen, cyano, $C_1$-$C_4$alkoxy $C_1$-$C_4$alkyl, $C_1$-$C_4$alkyl, $C_3$-$C_6$cycloalkyl, $C_1$-$C_4$alkyl $C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl and $C_1$-$C_4$haloalkylsulfonyl; or
$R_3$ and $R_6$ are independently triazolyl or pyrazolyl, both linked via a nitrogen atom to the ring which contains the substituent A, said triazolyl or pyrazolyl can be mono- or polysubstituted by substituents selected from the group consisting of halogen, cyano, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, $C_1$-$C_4$haloalkylsulfanyl, $C_1$-$C_4$haloalkylsulfinyl and $C_1$-$C_4$haloalkylsulfonyl; and
$R_7$ and $R_8$ are independently hydrogen, $C_1$-$C_4$alkyl, —C(O)cyclopropyl or cyclopropyl.

Another preferred group of compounds of formula I is represented by the compounds of formula I-1

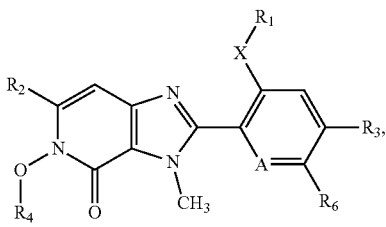

(I-1)

wherein the substituents X, $R_1$, $R_2$, $R_3$, $R_6$, $R_4$ and A are as defined under formula I above.

Further preferred embodiments of the invention are:

EMBODIMENT (A1)

Preferred are compounds of formula I-1, wherein
$R_1$ is $C_1$-$C_6$alkyl or $C_1$-$C_4$alkyl-$C_3$-$C_6$cycloalkyl;
$R_2$ is cyano, $C_1$-$C_6$haloalkyl, $C_1$-$C_6$haloalkoxy, $C_1$-$C_4$haloalkylsulfanyl, $C_1$-$C_4$haloalkylsulfinyl or $C_1$-$C_4$haloalkylsulfonyl; or
$R_2$ is $C_3$-$C_6$cycloalkyl which can be mono- or polysubstituted by substituents selected from the group consisting of halogen, cyano or $C_1$-$C_4$haloalkyl;
$R_4$ is hydrogen, $C_1$-$C_6$alkyl, $C_1$-$C_6$ haloalkyl, $C_2$-$C_6$alkenyl or $C_2$-$C_6$alkynyl; or
$R_4$ is $C_3$-$C_6$cycloalkyl which can be mono- or polysubstituted by substituents selected from the group consisting of halogen, cyano or $C_1$-$C_4$haloalkyl; or
$R_4$ is $C_1$-$C_4$alkyl mono- or polysubstituted by substituents selected from the group consisting of halogen, cyano, $C_3$-$C_6$cycloalkyl, phenyl, pyridyl, $C_1$-$C_4$ alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl and $C_1$-$C_4$alkoxy; and
X, $R_3$, $R_6$ and A are as defined under formula I above.

EMBODIMENT (A2)

Preferred are compounds of formula I-1, wherein
$R_1$ is $C_1$-$C_6$alkyl;
$R_2$ is $C_1$-$C_6$haloalkyl, $C_1$-$C_6$haloalkoxy, $C_1$-$C_4$haloalkylsulfanyl, $C_1$-$C_4$haloalkylsulfinyl or $C_1$-$C_4$haloalkylsulfonyl;
$R_4$ is hydrogen or $C_1$-$C_6$alkyl; and
X, $R_3$, $R_6$ and A are as defined under formula I above.

EMBODIMENT (A3)

Preferred are compounds of formula I-1, wherein
$R_1$ is $C_1$-$C_6$alkyl;
$R_2$ is $C_1$-$C_6$haloalkyl;
$R_4$ is hydrogen or $C_1$-$C_6$alkyl; and
X, $R_3$, $R_6$ and A are as defined under formula I above.

EMBODIMENT (A4)

In compounds of formula I-1 and all of the preferred embodiments of compounds of formula I-1 mentioned above, A is N or CH, X is preferably S or $SO_2$, and
$R_3$ and $R_6$ preferably are independently hydrogen, halogen, $C_1$-$C_6$haloalkyl or $R_7R_8N$—; or
$R_3$ and $R_6$ preferably are independently cyclopropyl which can be monosubstituted by cyano; or
$R_3$ and $R_6$ preferably are independently $C_1$-$C_4$alkyl which can be monosubstituted by cyano; or
$R_3$ and $R_6$ preferably are independently triazolyl or pyrazolyl, which each can be mono-substituted by substituents selected from the group consisting of halogen and cyano; wherein
$R_7$ and $R_8$ are hydrogen.

Another preferred group of compounds of formula I is represented by the compounds of formula I-2

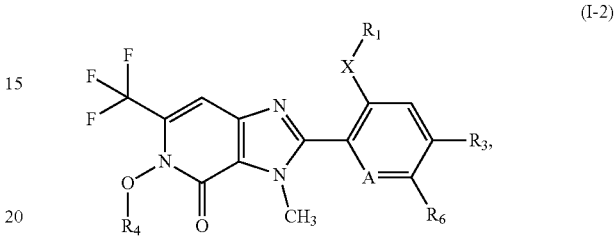

(I-2)

wherein the substituents X, $R_1$, $R_3$, $R_6$, $R_4$ and A are as defined under formula I above.

Further preferred embodiments of the invention are:

EMBODIMENT (A5)

Preferred are compounds of formula I-2, wherein
$R_1$ is $C_1$-$C_6$alkyl or $C_1$-$C_4$alkyl-$C_3$-$C_6$cycloalkyl;
$R_4$ is hydrogen, $C_1$-$C_6$alkyl, $C_1$-$C_6$ haloalkyl, $C_2$-$C_6$alkenyl or $C_2$-$C_6$alkynyl; or
$R_4$ is $C_3$-$C_6$cycloalkyl which can be mono- or polysubstituted by substituents selected from the group consisting of halogen, cyano or $C_0$-$C_4$haloalkyl; or
$R_4$ is $C_1$-$C_4$alkyl mono- or polysubstituted by substituents selected from the group consisting of halogen, cyano, $C_3$-$C_6$cycloalkyl, phenyl, pyridyl, $C_1$-$C_4$ alkylsulfanyl, $C_1$-$C_4$haloalkylsulfanyl, $C_1$-$C_4$alkylsulfinyl, $C_0$-$C_4$haloalkylsulfinyl, $C_1$-$C_4$alkylsulfonyl, $C_1$-$C_4$haloalkylsulfonyl and $C_0$-$C_4$alkoxy; and
X, $R_3$, $R_6$ and A are as defined under formula I above.

EMBODIMENT (A6)

Preferred are compounds of formula I-2, wherein
$R_1$ is $C_1$-$C_6$alkyl;
$R_4$ is hydrogen or $C_1$-$C_6$alkyl; and
X, $R_3$, $R_6$ and A are as defined under formula I above.

EMBODIMENT (A7)

In compounds of formula I-2 and all of the preferred embodiments of compounds of formula I-2 mentioned above, A is N or CH, X is preferably S or $SO_2$, and
$R_3$ and $R_6$ preferably are independently hydrogen, halogen, $C_1$-$C_6$haloalkyl or $R_7R_8N$—; or
$R_3$ and $R_6$ preferably are independently cyclopropyl which can be monosubstituted by cyano; or
$R_3$ and $R_6$ preferably are independently $C_1$-$C_4$alkyl which can be monosubstituted by cyano; or
$R_3$ and $R_6$ preferably are independently triazolyl or pyrazolyl, which each can be mono-substituted by substituents selected from the group consisting of halogen and cyano; wherein
$R_7$ and $R_8$ are hydrogen.

Another preferred group of compounds of formula I is represented by the compounds of formula I-3

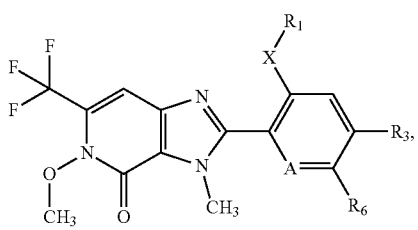

(I-3)

wherein the substituents X, $R_1$, $R_3$, $R_6$ and A are as defined under formula I above.

Further preferred embodiments of the invention are:

EMBODIMENT (A8)

Preferred are compounds of formula I-3, wherein
$R_1$ is $C_1$-$C_6$alkyl or $C_1$-$C_4$alkyl-$C_3$-$C_6$cycloalkyl; and
X, $R_3$, $R_6$ and A are as defined under formula I above.

EMBODIMENT (A9)

Preferred are compounds of formula I-3, wherein
$R_1$ is $C_1$-$C_6$alkyl; and
X, $R_3$, $R_6$ and A are as defined under formula I above.

EMBODIMENT (A10)

In compounds of formula I-3 and all of the preferred embodiments of compounds of formula I-3 mentioned above, A is N or CH, X is preferably S or $SO_2$, and
$R_3$ and $R_6$ preferably are independently hydrogen, halogen, $C_1$-$C_6$haloalkyl or $R_7R_8N$—; or
$R_3$ and $R_6$ preferably are independently cyclopropyl which can be monosubstituted by cyano; or
$R_3$ and $R_6$ preferably are independently $C_1$-$C_4$alkyl which can be monosubstituted by cyano; or
$R_3$ and $R_6$ preferably are independently triazolyl or pyrazolyl, which each can be mono-substituted by substituents selected from the group consisting of halogen and cyano; wherein
$R_7$ and $R_8$ are hydrogen.

Another preferred group of compounds of formula I is represented by the compounds of formula I-4

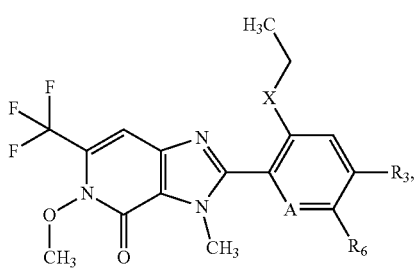

(I-4)

wherein the substituents X, $R_3$, $R_6$ and A are as defined under formula I above.

Further preferred embodiments of the invention are:

EMBODIMENT (A11)

Preferred are compounds of formula I-4, wherein
A is N or CH;
X is S, SO or $SO_2$, preferably S or $SO_2$; and
$R_3$ and $R_6$ are as defined under formula I above.

EMBODIMENT (A12)

Preferred are compounds of formula I-4, wherein
A is N or CH;
X is S, SO or $SO_2$, preferably S or $SO_2$; and
$R_3$ and $R_6$ preferably are independently hydrogen, halogen, $C_1$-$C_6$haloalkyl or $R_7R_8N$—; or
$R_3$ and $R_6$ preferably are independently cyclopropyl which can be monosubstituted by cyano; or
$R_3$ and $R_6$ preferably are independently $C_1$-$C_4$alkyl which can be monosubstituted by cyano; or
$R_3$ and $R_6$ preferably are independently triazolyl or pyrazolyl, which each can be mono-substituted by substituents selected from the group consisting of halogen and cyano; wherein
$R_7$ and $R_8$ are hydrogen;
and agrochemically acceptable salts, stereoisomers, enantiomers, tautomers and N-oxides of said especially preferred are compounds of formula I-4.

EMBODIMENT (A13)

Preferred are compounds of formula I-4, wherein
A is N or CH;
X is S, SO or $SO_2$, preferably S or $SO_2$; and
$R_3$ is halogen, preferably chloro or bromo; and
$R_6$ is $R_7R_8N$—; wherein
$R_7$ and $R_8$ are independently hydrogen, cyano, $C_2$-$C_4$ alkenyl, $C_2$-$C_4$haloalkenyl, $C_2$-$C_4$alkynyl, $C_2$-$C_4$haloalkynyl, $C_1$-$C_4$alkoxy-$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl, —C(O)$C_1$-$C_4$haloalkyl; or
$R_7$ and $R_8$ are independently —C(O)$C_3$-$C_6$cycloalkyl wherein the $C_3$-$C_6$cycloalkyl can be mono- to polysubstituted by substituents selected from the group consisting of halogen, cyano, $C_1$-$C_4$haloalkyl and $C_1$-$C_4$alkyl; or
$R_7$ and $R_8$ are independently $C_3$-$C_6$cycloalkyl which can be mono- to polysubstituted by substituents selected from the group consisting of halogen, cyano, $C_1$-$C_4$ haloalkyl and $C_1$-$C_4$alkyl.

EMBODIMENT (A14)

Preferred are compounds of formula I-4, wherein
A is N or CH;
X is S, SO or $SO_2$, preferably S or $SO_2$; and
$R_3$ is halogen, preferably chloro or bromo; and
$R_6$ is $R_7R_8N$—; wherein $R_7$ and $R_8$ are hydrogen;
and agrochemically acceptable salts, stereoisomers, enantiomers, tautomers and N-oxides of said especially preferred are compounds of formula I-4.

Another preferred group of compounds of formula I is represented by the compounds of formula I-5

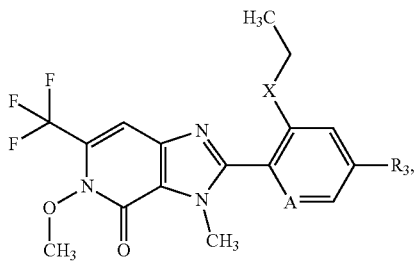
(I-5)

wherein the substituents X, $R_3$ and A are as defined under formula I above.

Further preferred embodiments of the invention are:

EMBODIMENT (B1)

Preferred are compounds of formula I-5, wherein
A is N or CH;
X is S, SO or $SO_2$, preferably S or $SO_2$; and
$R_3$ is as defined under formula I above.

EMBODIMENT (B2)

Preferred are compounds of formula I-5, wherein
A is N or CH;
X is S, SO or $SO_2$, preferably S or $SO_2$; and
$R_3$ is hydrogen, halogen or $C_1$-$C_6$haloalkyl, preferably hydrogen, chloro, bromo or trifluoromethyl; or
$R_3$ is cyclopropyl which can be monosubstituted by cyano; or
$R_3$ is $C_1$-$C_4$alkyl which can be monosubstituted by cyano, preferably isopropyl which can be monosubstituted by cyano; or
$R_3$ is $R_7R_8N$—; or
$R_3$ is a five-membered aromatic ring system linked via a nitrogen atom to the ring which contains the substituent A, said ring system can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl, $R_7R_8N$—, hydroxyl and —C(O)$C_1$-$C_4$haloalkyl; and said ring system contains 1, 2 or 3 heteroatoms selected from the group consisting of nitrogen, oxygen and sulphur, where said ring system may not contain more than one oxygen atom and not more than one sulfur atom; and
$R_7$ and $R_8$ are independently hydrogen, cyano, $C_2$-$C_4$ alkenyl, $C_2$-$C_4$haloalkenyl, $C_2$-$C_4$alkynyl, $C_2$-$C_4$haloalkynyl, $C_1$-$C_4$alkoxy-$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl, —C(O)$C_1$-$C_4$haloalkyl; or
$R_7$ and $R_8$ are independently —C(O)$C_3$-$C_6$cycloalkyl wherein the $C_3$-$C_6$cycloalkyl can be mono- to polysubstituted by substituents selected from the group consisting of halogen, cyano, $C_1$-$C_4$haloalkyl and $C_1$-$C_4$alkyl; or $R_7$ and $R_8$ are independently $C_3$-$C_6$cycloalkyl which can be mono- to polysubstituted by substituents selected from the group consisting of halogen, cyano, $C_1$-$C_4$ haloalkyl and $C_1$-$C_4$alkyl.

EMBODIMENT (B3)

Preferred are compounds of formula I-5, wherein
A is N or CH;
X is S, SO or $SO_2$, preferably S or $SO_2$; and
$R_3$ is hydrogen, halogen or $C_1$-$C_6$haloalkyl, preferably hydrogen, chloro, bromo or trifluoromethyl; or
$R_3$ is cyclopropyl which can be monosubstituted by cyano; or
$R_3$ is $C_1$-$C_4$alkyl which can be monosubstituted by cyano, preferably isopropyl which can be monosubstituted by cyano; or
$R_3$ is $R_7R_8N$—, wherein $R_7$ and $R_8$ are hydrogen; or
$R_3$ is triazolyl or pyrazolyl, which each can be monosubstituted by substituents selected from the group consisting of halogen and cyano.

EMBODIMENT (B4)

Preferred are compounds of formula I-5, wherein
A is N or CH;
X is S, SO or $SO_2$, preferably S or $SO_2$; and
$R_3$ is hydrogen, halogen or $C_1$-$C_6$haloalkyl, preferably hydrogen, chloro, bromo or trifluoromethyl; or
$R_3$ is cyclopropyl which can be monosubstituted by cyano; or
$R_3$ is $C_1$-$C_4$alkyl which can be monosubstituted by cyano, preferably isopropyl which can be monosubstituted by cyano; or
$R_3$ is $R_7R_8N$—, wherein $R_7$ and $R_8$ are hydrogen; or
$R_3$ is unsubstituted triazolyl, linked via any nitrogen atom to the ring which contains the substituent A.

EMBODIMENT (B5)

Preferred are compounds of formula I-5, wherein
A is N or CH;
X is S, SO or $SO_2$, preferably S or $SO_2$; and
$R_3$ is hydrogen, halogen or $C_1$-$C_6$haloalkyl, preferably hydrogen, chloro, bromo or trifluoromethyl; or
$R_3$ is cyclopropyl which can be monosubstituted by cyano; or
$R_3$ is $C_1$-$C_4$alkyl which can be monosubstituted by cyano, preferably isopropyl which can be monosubstituted by cyano;
and agrochemically acceptable salts, stereoisomers, enantiomers, tautomers and N-oxides of said especially preferred are compounds of formula I-5.

Another preferred group of compounds of formula I is represented by the compounds of formula I-6

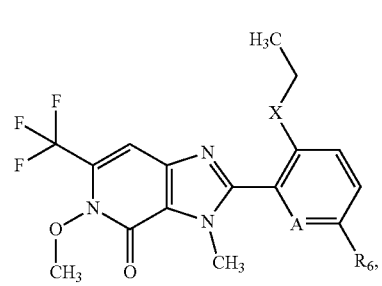
(I-6)

wherein the substituents X, $R_6$ and A are as defined under formula I above.

Further preferred embodiments of the invention are:

EMBODIMENT (C1)

Preferred are compounds of formula I-6, wherein
A is N or CH;
X is S, SO or $SO_2$, preferably S or $SO_2$; and
$R_6$ is as defined under formula I above.

EMBODIMENT (C2)

Preferred are compounds of formula I-6, wherein
A is N or CH;
X is S, SO or $SO_2$, preferably S or $SO_2$;
$R_6$ is hydrogen, halogen or $C_1$-$C_6$haloalkyl, preferably hydrogen, chloro, bromo or trifluoromethyl; or
$R_6$ is cyclopropyl which can be monosubstituted by cyano; or
$R_6$ is $C_1$-$C_4$alkyl which can be monosubstituted by cyano, preferably isopropyl which can be monosubstituted by cyano; or
$R_6$ is $R_7R_8N$—; or
$R_6$ is a five-membered aromatic ring system linked via a nitrogen atom to the ring which contains the substituent A, said ring system can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy-$C_1$-$C_4$alkyl, $C_1$-$C_4$alkyl, $C_3$-$C_6$cycloalkyl, $C_1$-$C_4$alkyl-$C_3$-$C_6$cycloalkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl, $R_7R_8N$—, hydroxyl and —C(O)$C_1$-$C_4$haloalkyl; and said ring system contains 1, 2 or 3 heteroatoms selected from the group consisting of nitrogen, oxygen and sulphur, where said ring system may not contain more than one oxygen atom and not more than one sulfur atom; and
$R_7$ and $R_8$ are independently hydrogen, cyano, $C_2$-$C_4$alkenyl, $C_2$-$C_4$haloalkenyl, $C_2$-$C_4$alkynyl, $C_2$-$C_4$haloalkynyl, $C_1$-$C_4$alkoxy-$C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl, —C(O)$C_1$-$C_4$haloalkyl; or
$R_7$ and $R_8$ are independently —C(O)$C_3$-$C_6$cycloalkyl wherein the $C_3$-$C_6$cycloalkyl can be mono- to polysubstituted by substituents selected from the group consisting of halogen, cyano, $C_1$-$C_4$haloalkyl and $C_1$-$C_4$alkyl; or
$R_7$ and $R_8$ are independently $C_3$-$C_6$cycloalkyl which can be mono- to polysubstituted by substituents selected from the group consisting of halogen, cyano, $C_1$-$C_4$ haloalkyl and $C_1$-$C_4$alkyl.

EMBODIMENT (C3)

Preferred are compounds of formula I-6, wherein
A is N or CH;
X is S, SO or $SO_2$, preferably S or $SO_2$; and
$R_6$ is hydrogen, halogen or $C_1$-$C_6$haloalkyl, preferably hydrogen, chloro, bromo or trifluoromethyl; or
$R_6$ is cyclopropyl which can be monosubstituted by cyano; or
$R_6$ is $C_1$-$C_4$alkyl which can be monosubstituted by cyano, preferably isopropyl which can be monosubstituted by cyano; or
$R_6$ is $R_7R_8N$—, wherein $R_7$ and $R_8$ are hydrogen; or
$R_6$ is triazolyl or pyrazolyl, which each can be monosubstituted by substituents selected from the group consisting of halogen and cyano.

EMBODIMENT (C4)

Preferred are compounds of formula I-6, wherein
A is N or CH;
X is S, SO or $SO_2$, preferably S or $SO_2$; and
$R_6$ is hydrogen or halogen, preferably hydrogen, fluoro, chloro or bromo; or
$R_6$ is $R_7R_8N$—, wherein $R_7$ and $R_8$ are hydrogen; or
$R_6$ is triazolyl or pyrazolyl, which each can be monosubstituted by substituents selected from the group consisting of halogen and cyano.

EMBODIMENT (C5)

Preferred are compounds of formula I-6, wherein
A is N or CH;
X is S, SO or $SO_2$, preferably S or $SO_2$; and
$R_6$ is hydrogen or halogen, preferably hydrogen, fluoro, chloro or bromo; or
$R_6$ is $R_7R_8N$—, wherein $R_7$ and $R_8$ are hydrogen; or
$R_6$ is unsubstituted triazolyl, linked via any nitrogen atom to the ring which contains the substituent A; and agrochemically acceptable salts, stereoisomers, enantiomers, tautomers and N-oxides of said especially preferred are compounds of formula I-5.

An especially preferred embodiment of the invention comprises compounds of formula I represented by the compounds of formula I-7

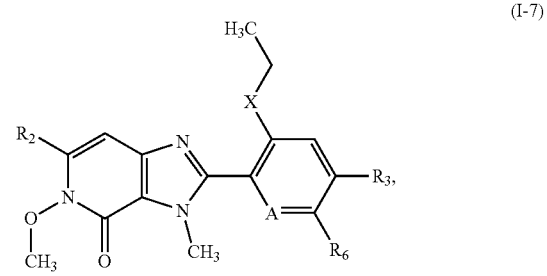

(I-7)

wherein
A is N or CH;
X is S or $SO_2$;
$R_2$ is $C_1$-$C_6$haloalkyl, preferably trifluoromethyl;
$R_4$ is $C_1$-$C_6$alkyl, preferably methyl; and
$R_3$ and $R_6$ are independently hydrogen, halogen, $C_1$-$C_6$haloalkyl or $R_7R_8N$—; or
$R_3$ and $R_6$ are independently cyclopropyl which can be monosubstituted by cyano; or
$R_3$ and $R_6$ are independently $C_1$-$C_4$alkyl which can be monosubstituted by cyano; or
$R_3$ and $R_6$ are independently unsubstituted triazolyl, linked via any nitrogen atom to the ring which contains the substituent A; wherein
$R_7$ and $R_8$ are hydrogen;

and agrochemically acceptable salts, stereoisomers, enantiomers, tautomers and N-oxides of said especially preferred are compounds of formula I-7.

In the especially preferred embodiment of formula I-7 above, $R_3$ is preferably hydrogen, halogen or $C_1$-$C_6$haloalkyl, in particular hydrogen, chloro, bromo or trifluoromethyl; or
$R_3$ is preferably cyclopropyl which can be monosubstituted by cyano; or
$R_3$ is $C_1$-$C_4$alkyl which can be monosubstituted by cyano, in particular isopropyl which can be monosubstituted by cyano;
$R_6$ is preferably hydrogen or halogen, in particular hydrogen, fluoro, chloro or bromo; or
$R_6$ is preferably $R_7R_8N$—, wherein $R_7$ and $R_8$ are hydrogen; or
$R_6$ is preferably unsubstituted triazolyl, linked via any nitrogen atom to the ring which contains the substituent A.

The process according to the invention for preparing compounds of formula (I) is carried out by methods known to those skilled in the art, or described for example in WO 2009/131237, WO 2011/043404, WO 2011/040629, WO 2010/125985, WO 2012/086848, WO 2013/018928, WO 2013/191113, WO 2013/180193, WO 2013/180194, WO 2016/023954 and WO 2016/142326, and involves reaction of a compound of formula II,

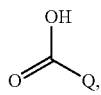
(II)

wherein Q is the group

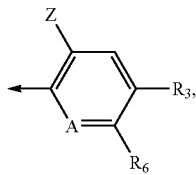
(Q)

wherein Z is X—$R_1$ or a leaving group, for example a halogen (preferably fluoro or chloro), and wherein X, $R_1$, $R_3$, $R_6$ and A are as described under formula I above, and wherein the arrow in the radical Q shows the point of attachment to the carbon atom of the carboxyl group in the compound of formula II, with a compound of formula III,

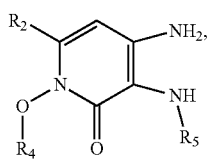
(III)

wherein $R_2$, $R_4$ and $R_5$ are as described under formula I above, in the presence of a dehydrating agent, such as for example polyphosphoric acid at temperature between 150° C. to 250° C., to yield compounds of formula Ia, wherein the substituents are as described above and under formula I.

Such processes are well known and have been described for example in WO 2008/128968 or WO 2006/003440. The process is summarized in scheme 1 for compounds of formula Ia:

Scheme 1

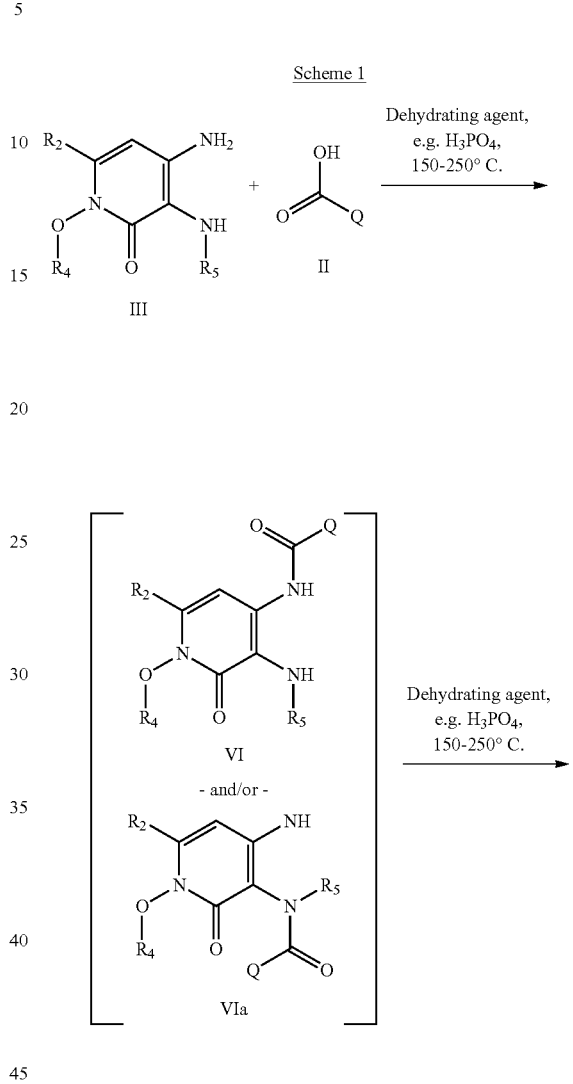

As can be seen in scheme 1, the formation of compounds of formula Ia occurs through the intermediacy of a compound of formula VI (and/or its position isomer VIa). Intermediate VI or intermediate VIa may form as a pure entity, or intermediates VI and VIa may arise as a mixture of regioisomeric acylation products. It is in many cases advantageous to thus prepare compounds of formula (I), respectively (Ia), through such intermediates VI/VIa, which may be isolated and optionally purified. This is illustrated for compounds of formula Ia in scheme 2:

Scheme 2

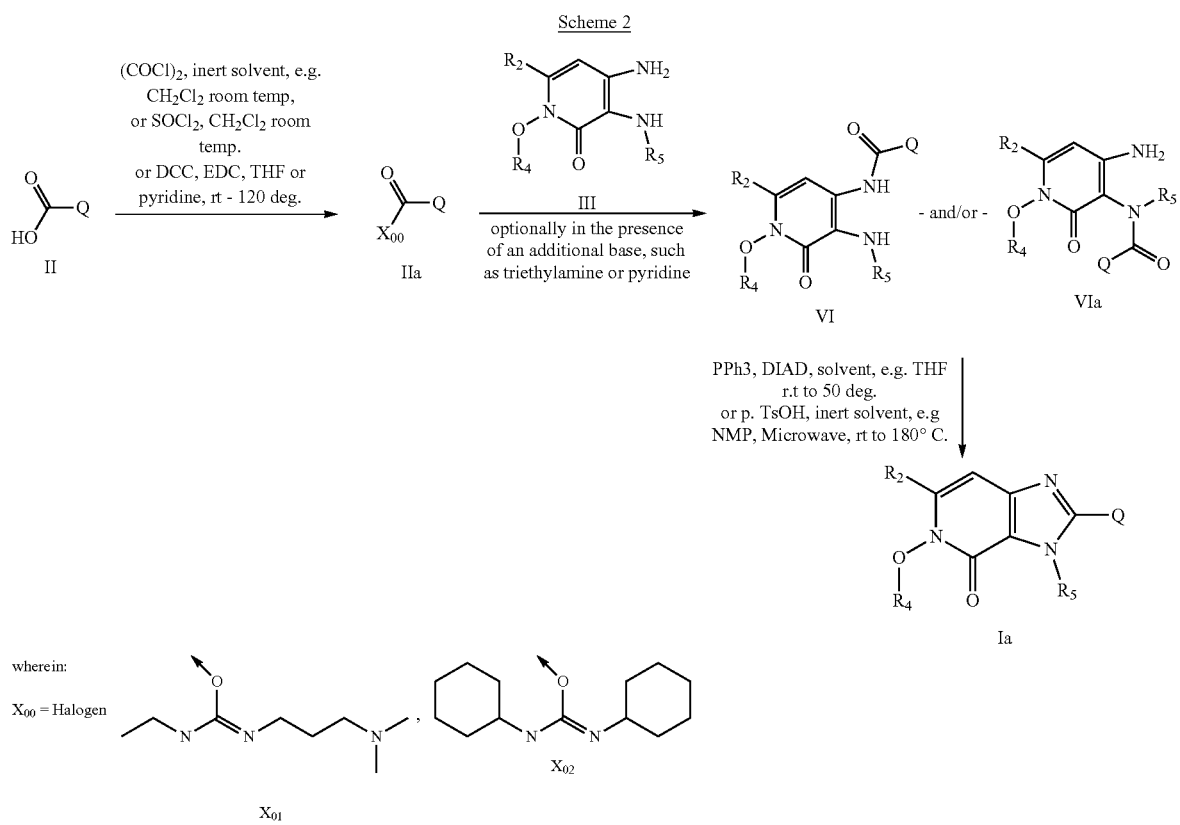

Compounds of the formula VI and/or VIa (or a mixture thereof), or a salt thereof, wherein Q is as defined above, and wherein $R_2$, $R_4$ and $R_5$ are as described under formula I above, may be prepared by i) activation of compound of formula II, wherein Q is as defined above, by methods known to those skilled in the art and described in, for example, Tetrahedron, 2005, 61 (46), 10827-10852, to form an activated species IIa, wherein Q is as defined above and wherein $X_{00}$ is halogen, preferably chlorine. For example, compounds IIa where $X_{00}$ is halogen, preferably chlorine, are formed by treatment of II with, for example, oxalyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula II with, for example, 1-ethyl-3-(3-dimethylaminopropyl)carbodiimide EDC or dicyclohexyl carbodiimide DCC will generate an activated species IIa, wherein $X_{00}$ is $X_{01}$ or $X_{02}$ respectively, in an inert solvent, such as pyridine or tetrahydrofuran THF, optionally in the presence of a base, such as triethylamine, at temperatures between 25-180° C.; followed by ii) treatment of the activated species IIa with a compound of formula III (or a salt thereof), wherein $R_2$, $R_4$ and $R_5$ are as described under formula I above, optionally in the presence of a base, such as triethylamine or pyridine, in an inert solvents such as dichloromethane, tetrahydrofuran, dioxane or toluene, at temperatures between 0 and 80° C., to form the compounds of formula VI and/or Via (or a mixture thereof).

Compounds of formula VI and/or Via (or a mixture thereof) may further be converted into compounds of formula Ia, wherein Q is as defined above, and wherein $R_2$, $R_4$ and $R_5$ are as described under formula I above, by dehydration, eg. by heating the compounds VI and/or Via (or a mixture thereof) in the presence of an acid catalyst, such as for example methane sulfonic acid, or para-toluene sulfonic acid TsOH, in an inert solvent such as toluene, xylene, N,N-dimethylfomamide DMF, or N-methyl pyrrolidine NMP (or mixtures thereof) at temperatures between 25-180° C., preferably 100-170° C., optionally under microwave conditions. Alternatively, heating the compounds VI and/or Via (or a mixture thereof) in solvents such as acetic acid or trifluoroacetic acid, at temperatures up to the boiling point of the reaction mixture, optionally under microwave conditions, will also generate compounds of formula Ia. Such processes have been described previously, for example, in WO 2010/125985.

Compounds of formula Ia, wherein Q is as defined above, and wherein Z is a leaving group, for example halogen, preferably fluorine or chlorine, and wherein $R_2$, $R_4$ and $R_5$ are as described under formula I above, can be reacted with compounds of formula V $$R_1—SH \qquad (V),$$

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ib, in which X is S (a sulfide), and wherein $R_1$ is as described under formula I above, and in which A, $R_2$, $R_3$, $R_4$, $R_5$ and $R_6$ are as described under formula I above.

Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO 2013/018928. Examples of salts of the compound of formula V include compounds of the formula Va $$R_1-S-M \quad (Va),$$

wherein $R_1$ is as defined above and wherein M is, for example, sodium or potassium. This is illustrated for compounds of formula Ib in scheme 3:

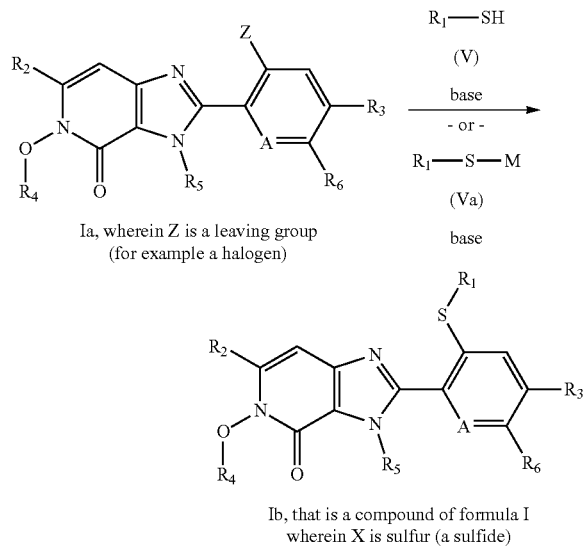

Alternatively, this reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described by Perrio et al. in Tetrahedron 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ib above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of oxidant to be used in the reaction is generally 1 to 3 moles, preferably 1 to 1.2 moles, relative to 1 mole of the sulfide compounds Ib to produce the sulfoxide compounds I (wherein X=SO), and preferably 2 to 2.2 moles of oxidant, relative to 1 mole of of the sulfide compounds Ib to produce the sulfone compounds I (wherein X=$SO_2$). Such oxidation reactions are disclosed, for example, in WO 2013/018928, WO 2016/023954 or WO 2016/142326.

The sequence to prepare compounds of formula III wherein $R_2$, $R_4$ and $R_5$ are as described under formula I above, from compounds of formula VII, may involve (scheme 4): step i. alkylation of compound VII with $R_5$—$X_{LG}$, wherein $R_5$ is as described under formula I above and wherein $X_{LG}$ is a leaving group, such as a halogen, preferably iodine, bromine or chlorine, in presence of a base, such as sodium carbonate, potassium carbonate or cesium carbonate, or sodium hydride, in a appropriate solvent such as for example tetrahydrofuran, N,N-dimethylformamide, N,N-dimethylacetamide or acetonitrile, to generate a compound of formula VIII, wherein $R_4$, $R_5$ and $R_2$ are as described under formula I above; step ii. nitration of compound VIII into compound IX, wherein $R_4$, $R_5$ and $R_2$ are as described under formula I above, under classical conditions described for example in Advanced Organic Chemistry: Reactions, Mechanisms, and Structure, Fourth Edition by Jerry March, 1992 (Publisher Wiley New York, N.Y.) p 523-525; and finally step iii. reduction of compound IX into compound III under classical conditions described for example in Advanced Organic Chemistry: Reactions, Mechanisms, and Structure, Fourth Edition by Jerry March, 1992 (Publisher Wiley New York, N.Y.) p 1216-1217.

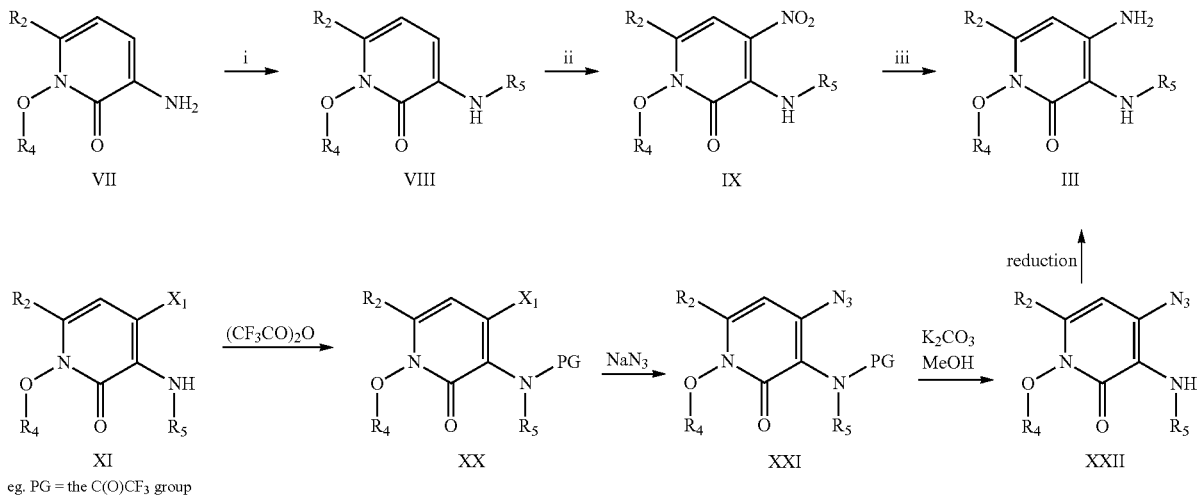

Alternatively, compounds of formula III, wherein $R_2$, $R_4$ and $R_5$ are as described under formula I above, can also be prepared from compounds of formula XI, wherein $R_2$, $R_4$ and $R_5$ are as described under formula I, and in which $X_1$ is halogen, preferably chlorine or bromine (scheme 4). Compounds of formula XX, wherein $R_2$, $R_4$ and $R_5$ are as described under formula I above, and in which $X_1$ is halogen, preferably chlorine or bromine, and wherein PG is a protective group, such as $C_1$-$C_6$alkyl-carbonyl (for example acetyl) or halo$C_1$-$C_6$alkyl-carbonyl (for example trifluoroacetyl), preferably PG is trifluoroacetyl, can be prepared by reacting compounds of formula XI, wherein $R_2$, $R_4$ and $R_5$ are as described under formula I, and in which $X_1$ is halogen, preferably chlorine or bromine, with an anhydride reagent of formula $(R_{PG})_2O$, wherein $R_{PG}$ is $C_1$-$C_6$alkyl-carbonyl (for example $(R_{PG})_2O$ is acetic anhydride) or halo$C_1$-$C_6$alkyl-carbonyl (for example $(R_{PG})_2O$ is trifluoroacetic anhydride), preferably $(R_{PG})_2O$ is trifluoroacetic anhydride $(CF_3CO)_2O$, optionally in presence of a base such as triethylamine, diisopropylethylamine or pyridine, optionally in presence of an acylation catalyst such as 4-dimethylaminopyridine, in solvents such as dichloromethane, tetrahydrofuran or dioxane, at temperatures between 0 and 100° C., preferably between 0° C. and 30° C. Such introduction of specific protecting groups is very known to those skilled in the art, see for example Protective Groups in Organic Synthesis, 3nd Ed Greene TW, Wuts PGM, 1999, pp 518-525.

Compounds of formula XXI, wherein $R_2$, $R_4$ and $R_5$ are as described under formula I above, and wherein PG is a protective group, such as $C_1$-$C_6$alkyl-carbonyl (for example acetyl) or halo$C_1$-$C_6$alkyl-carbonyl (for example trifluoroacetyl), preferably PG is trifluoroacetyl, can be prepared by reacting compounds of formula XX, wherein $R_2$, $R_4$ and $R_5$ are as described under formula I above, and in which $X_1$ is halogen, preferably chlorine or bromine, and wherein PG is a protective group, such as $C_1$-$C_6$alkyl-carbonyl (for example acetyl) or halo$C_1$-$C_6$alkyl-carbonyl (for example trifluoroacetyl), preferably PG is trifluoroacetyl, with for example sodium azide $NaN_3$, optionally in presence of a complexant (such as, for example, 15-crown-5) that could complex various cations, in an inert solvent such as tetrahydrofuran, dioxane, acetonitrile, N,N-dimethylformamide, N,N-dimethylacetamide, N-methyl-2-pyrrolidone or dimethyl sulfoxide (or mixtures thereof), at temperatures between 0 and 180° C., preferably between 20 and 150° C., optionally under microwave irradiation.

Compounds of formula XXII, wherein $R_2$, $R_4$ and $R_5$ are as described under formula I above, can be prepared by reacting compounds of formula XXI, wherein $R_2$, $R_4$ and $R_5$ are as described under formula I above, and wherein PG is a protective group, such as $C_1$-$C_6$alkyl-carbonyl (for example acetyl) or halo$C_1$-$C_6$alkyl-carbonyl (for example trifluoroacetyl), preferably PG is trifluoroacetyl, with a base such as alkali metal carbonates, for example lithium, sodium, potassium or cesium carbonate, in an alcohol solvent such as methanol, ethanol or isopropanol, optionally in presence of water, at temperatures between 0 and 100° C., preferably between 0° C. and 30° C.

Compounds of formula III, wherein $R_2$, $R_4$ and $R_5$ are as described under formula I above, can be prepared by reacting compounds of formula XXII, wherein $R_2$, $R_4$ and $R_5$ are as described under formula I above, with trivalent phosphorous compounds, for example trialkyl- or triarylphosphines, preferably triphenylphosphine, and hydrolyzing in situ the generated iminophosphorane (or aza-ylide, Staudinger reaction) with water, optionally in presence of acid, such as hydrochloric or hydrobromic acid. Overall, azide compounds of formula XXII undergo a formal reduction to form primary amine compounds of formula III in this transformation. This reaction may be performed in an inert solvent such as tetrahydrofuran or dioxane, at temperatures between 0 and 180° C., preferably between 20 and 150° C., optionally under microwave irradiation. Alternatively, azido compounds of formula XXII may be reduced to amino compounds of formula III using molecular hydrogen ($H_2$), optionally under pressure, usually in the presence of a catalyst such as nickel, palladium or platinum, in inert solvents (such as for example ethyl acetate, methanol or ethanol), at temperatures between 0° C. and 120° C., preferably between 30° C. and reflux temperature.

Compounds of formula VII, wherein $R_2$ and $R_4$ are as described under formula I above, may be prepared by methods known to a person skilled in the art. For example via: step 1.) the reaction of compound VIIa, wherein $R_2$ is as described under formula I above, with an appropriate hydroxylamine $H_2NOR_4$, or a salt thereof (such as a hydrohalide salt, preferably a hydrochloride or a hydrobromide salt, or any other equivalent salt), wherein $R_4$ is as described under formula I above (scheme 5); followed by step 2.) cleavage of the benzoyl group by hydrolysis either under acidic (for example aqueous hydrochloric acid) or basic (for example lithium or sodium hydroxide, in an inert solvent such as tetrahydrofuran or dioxane, optionally in presence of water) conditions. Compounds of formula VIIa, wherein $R_2$ is as described under formula I above, may prepared by methods known to a person skilled in the art. See, for example, Synthesis 2005, No. 8, pp 1269-1278 and Synthesis 2011, No. 7, pp 1149-1156.

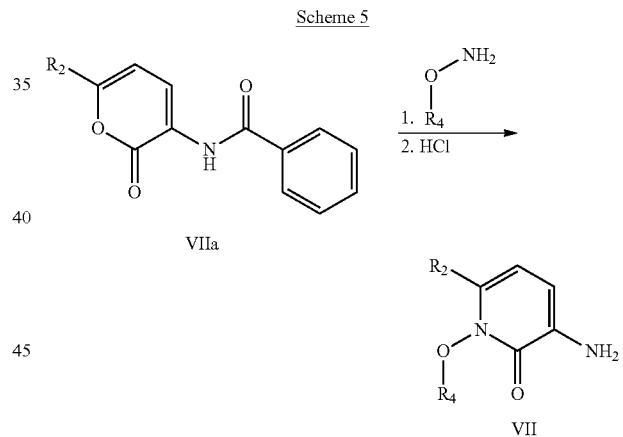

Scheme 5

VIIa

VII

The preparation of compounds of formula XI, wherein $R_2$, $R_4$ and $R_5$ are as described under formula I, and in which $X_1$ is halogen, preferably chlorine or bromine, is detailed below (see scheme 8).

Compounds of formula I-2, wherein Z is X—$R_1$ or a leaving group, for example a halogen (preferably fluoro or chloro), and wherein X, $R_1$, $R_2$, $R_3$, $R_4$, $R_5$, $R_6$ and A are as described under formula I above, may be prepared by reaction between compounds of formula II respectively IIa, wherein Z is X—$R_1$ or a leaving group, for example a halogen (preferably fluoro or chloro), and wherein X, $R_1$, $R_3$, $R_6$ and A are as described under formula I above, and in which $X_{00}$ is as described above, and compounds of formula III, or a salt thereof, wherein $R_4$, $R_5$ and $R_2$ are as described under formula I above, under similar conditions as for the preparation of compounds of formula Ia from compounds of formula II/IIa and III described above (see schemes 1 and 2). This is illustrated in scheme 6.

Scheme 6

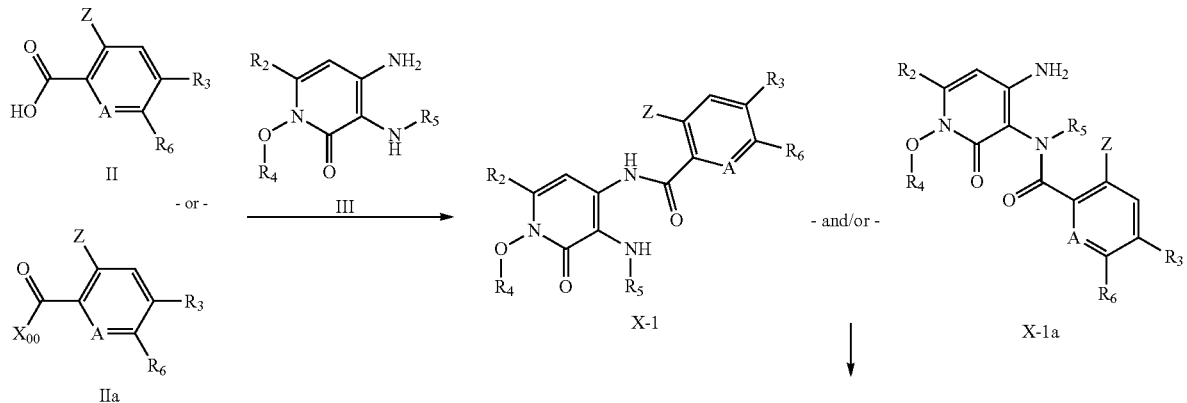

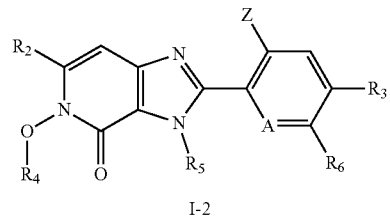

Compounds of formula I can be made by reacting compounds of compounds of formula I-2, wherein Z is a leaving group, for example a halogen (preferably fluoro or chloro) with compounds of formula V or Va as described in scheme 3. All substituents are as defined above.

Alternatively, compounds of formula I-2, wherein Z is $X-R_1$ or a leaving group, for example a halogen (preferably fluoro or chloro), and wherein X, $R_1$, $R_2$, $R_3$, $R_4$, $R_5$, $R_6$ and A are as described under formula I above, can be prepared (scheme 7) by i.) reaction between compounds of formula XI, or a salt thereof, wherein $R_2$, $R_4$ and $R_5$ are as described under formula I above, and in which $X_1$ is a leaving group, such as a halogen, preferably chlorine or bromine, and compounds of formula II or IIa, wherein Z is $X-R_1$ or a leaving group, for example a halogen (preferably fluoro or chloro), and wherein X, $R_1$, $R_3$, $R_6$ and A are as described under formula I above, and in which $X_{00}$ is as described above, under similar conditions as for the preparation of compounds of formula VIa from compounds of formula II/IIa and III described above (see scheme 2). This transformation generates compounds of the formula X-2, wherein Z is $X-R_1$ or a leaving group, for example a halogen (preferably fluoro or chloro), and wherein X, $R_1$, $R_2$, $R_3$, $R_4$, $R_5$, $R_6$ and A are as described under formula I above, and in which $X_1$ is a leaving group, such as a halogen, preferably chlorine or bromine; followed by Scheme 7

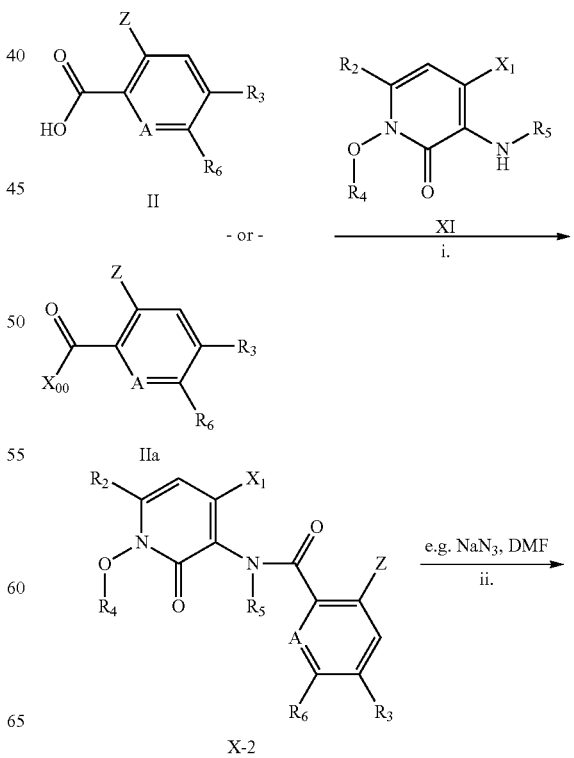

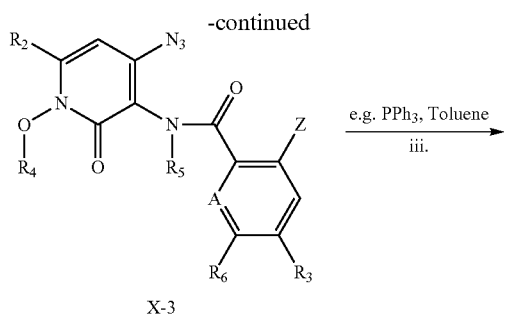

X-3

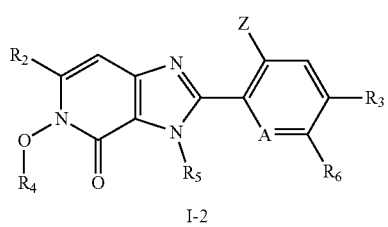

I-2 ii.) substitution of $X_1$, a leaving group, such as a halogen, preferably chlorine or bromine, in compounds of formula X-2 by an azido group to form compounds of formula X-3, wherein Z is X—$R_1$ or a leaving group, for example a halogen (preferably fluoro or chloro), and wherein X, $R_1$, $R_2$, $R_3$, $R_4$, $R_5$, $R_6$ and A are as described under formula I above. This transformation is usually carried out in the presence of an azide salt such as, for example sodium azide $NaN_3$, optionally in presence of a complexant (such as, for example, 15-crown-5) that could complex various cations, in an inert solvent such as tetrahydrofuran, dioxane, acetonitrile, N,N-dimethylformamide, N,N-dimethylacetamide, N-methyl-2-pyrrolidone or dimethyl sulfoxide (or mixtures thereof), at temperatures between 0 and 180° C., preferably between 20 and 150° C., optionally under microwave irradiation; further followed by iii.) formation of compounds of formula I-2, wherein Z is X—$R_1$ or a leaving group, for example a halogen (preferably fluoro or chloro), and wherein X, $R_1$, $R_2$, $R_3$, $R_4$, $R_5$, $R_6$ and A are as described under formula I above, from compounds of formula X-3 via a tandem Staudinger/cyclisation reaction. In this transformation, compounds of formula X-3, wherein Z is X—$R_1$ or a leaving group, for example a halogen (preferably fluoro or chloro), and wherein X, $R_1$, $R_2$, $R_3$, $R_4$, $R_5$, $R_6$ and A are as described under formula I above, are treated with trivalent phosphorous compounds, for example trialkyl- or triarylphosphines, preferably triphenylphosphine, to in situ generate an iminophosphorane (or aza-ylide, Staudinger reaction) intermediate, which cyclises with the amide radical —$NR_5C(O)$— to form compounds of formula I-2. This reaction may be performed in an inert solvent such as tetrahydrofuran, dioxane, toluene or xylene, at temperatures between 0 and 200° C., preferably between 20 and 180° C., optionally under microwave irradiation. The Staudinger reaction is known to those skilled in the art, reaction of its corresponding iminophosphorane (aza-ylide) with groups such as carboxylic acid derivatives or ketones described in, for example, Strategic Applications of Named Reactions in Organic Synthesis by Kurti, Laszlo; Czako, Barbara; Editors; 2005, pp. 428-429. Alternatives are possible, such as conditions described in, for example, Chemistry & Industry (London, United Kingdom) 1984, pp. 222-3.

Compounds of formula XI, wherein $R_2$, $R_4$ and $R_5$ are as described under formula I above, and in which $X_1$ is halogen, preferably chlorine or bromine, can be prepared (scheme 8) by i.) reacting compounds of formula compound VIIa, wherein $R_2$ is as described under formula I above, with an appropriate hydroxylamine $H_2NOR_4$ (such as O-methyl hydroxylamine), or a salt thereof (such as a hydrohalide salt, preferably a hydrochloride or a hydrobromide salt, or any other equivalent salt), wherein $R_4$ is as described under formula I above, under acidic conditions, for example in acetic (AcOH) or trifluoroacetic acid, optionally in presence of a further inert solvent or diluent, such as dichloromethane, toluene, tetrahydrofuran THF or dioxane to form compounds of formula XVII, wherein $R_2$ and $R_4$ are as described under formula I above. The reaction temperature can preferentially range from room temperature to the boiling point of the reaction mixture, or alternatively heating may be performed under microwave irradiation; followed by either iia.) reaction of compounds of formula XVII, wherein $R_2$ and $R_4$ are as described under formula I above, under acidic conditions, for example in hydrochloric or acetic acid, to form compounds of formula XVI, wherein $R_2$ and $R_4$ are as described under formula I above, by dehydration. The reaction temperature can preferentially range from room temperature to the boiling point of the reaction mixture, or alternatively heating may be performed under microwave irradiation. Further, reacting compounds of formula XVI, with, for example, di-tert-butyl dicarbonate (BOC anhydride, $BOC_2O$), in presence of a base, such as triethylamine $NEt_3$, diisopropylethylamine or pyridine, optionally in presence of an acylation catalyst such as 4-dimethylaminopyridine DMAP, in an inert solvent such as dichloromethane DCM, tetrahydrofuran, dioxane or toluene, at temperatures between 0 and 100° C., preferably between 0° C. and 30° C., to form compounds of formula XV, wherein $R_2$ and $R_4$ are as described under formula I above, and in which PG is, for example, the BOC group —C(O)Ot-Bu (t-butyloxycarbonyl). Such introduction of specific protecting groups is very known to those skilled in the art, see for example Protective Groups in Organic Synthesis, 3nd Ed Greene TW, Wuts PGM, 1999, pp 518-525; or alternatively Scheme 8

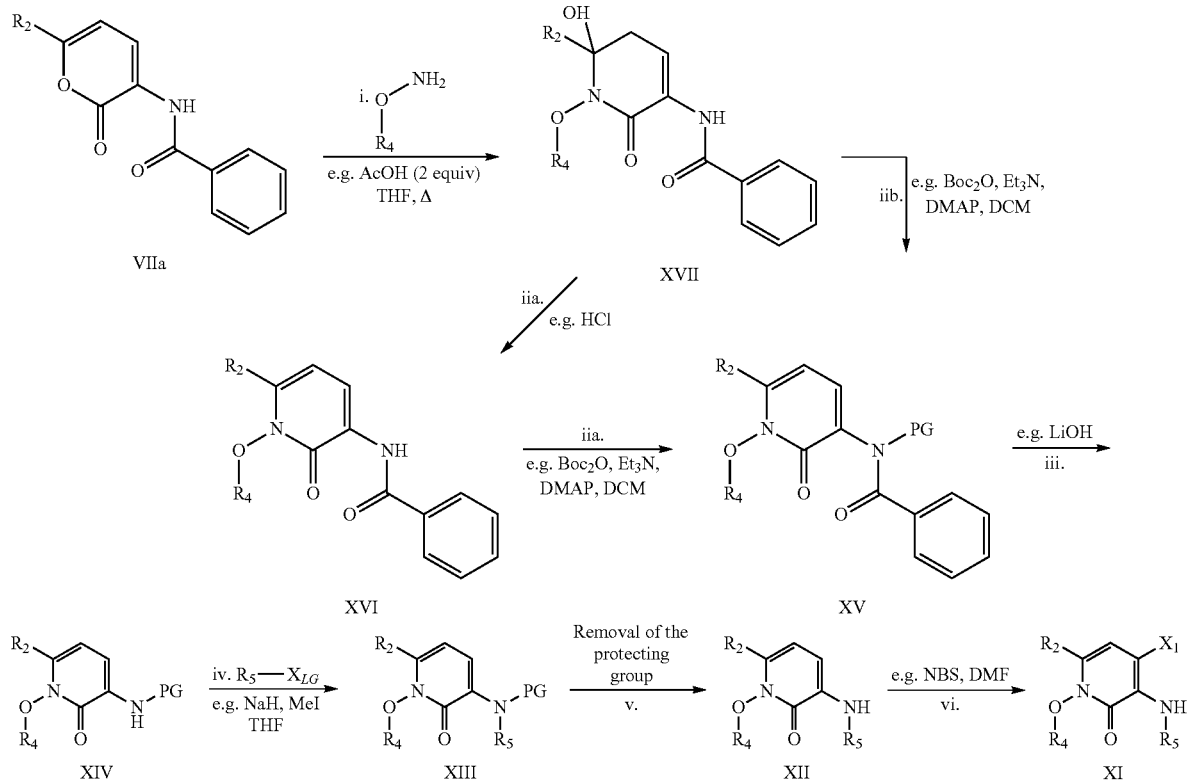

iib.) reaction of compounds of formula XVII, wherein $R_2$ and $R_4$ are as described under formula I above, with, for example, di-tert-butyl dicarbonate (BOC anhydride, $BOC_2O$), preferably at least two equivalents, in presence of a base, such as triethylamine $NEt_3$, diisopropylethylamine or pyridine, preferably at least two equivalents, optionally in presence of an acylation catalyst such as 4-dimethylaminopyridine DMAP, in an inert solvent such as dichloromethane DCM, tetrahydrofuran, dioxane or toluene, at temperatures between 0 and 100° C., preferably between 0° C. and 30° C., to directly form compounds of formula XV, wherein $R_2$ and $R_4$ are as described under formula I above, and in which PG is, for example, the BOC group —C(O)Ot-Bu (t-butyloxycarbonyl) via tandem formal dehydration/BOC group introduction; followed by iii.) cleavage of the benzoyl group in compounds of formula XV by hydrolysis either under acidic (for example aqueous hydrochloric acid) or basic (for example lithium or sodium hydroxide, in an inert solvent such as tetrahydrofuran or dioxane, optionally in presence of water) conditions, at temperatures between 0 and 100° C., preferably between 0° C. and 50° C., to form compounds of formula XIV, wherein $R_2$ and $R_4$ are as described under formula I above, and in which PG is, for example, the BOC group —C(O)Ot-Bu (t-butyloxycarbonyl); followed by iv.) alkylation of compounds of formula XIV, wherein $R_2$ and $R_4$ are as described under formula I above, and in which PG is, for example, the BOC group —C(O)Ot-Bu (t-butyloxycarbonyl), with a reagent $R_5$—$X_{LG}$, wherein $R_5$ is as described under formula I above and wherein $X_{LG}$ is a leaving group, such as halogen, preferably iodine, bromine or chlorine (for example is $R_5$—$X_{LG}$ is methyl iodide MeI), in presence of a base, such as sodium carbonate, potassium carbonate or cesium carbonate, or sodium hydride NaH, in a appropriate solvent such as for example tetrahydrofuran THF, N,N-dimethylformamide, N,N-dimethylacetamide or acetonitrile, at temperatures between −20 and 100° C., preferably between 0° C. and 80° C., to form compounds of formula XIII, wherein $R_4$, $R_5$ and $R_2$ are as described under formula I above, and in which PG is, for example, the BOC group —C(O)Ot-Bu (t-butyloxycarbonyl); followed by v.) cleavage of the protective group PG, for example the BOC group —C(O)Ot-Bu (t-butyloxycarbonyl), in compounds of formula XIII, usually by hydrolysis either under acidic (for example aqueous hydrochloric acid) or basic (for example lithium or sodium hydroxide, in an inert solvent such as tetrahydrofuran or dioxane, optionally in presence of water) conditions, or by acidic treatment (for example with trifluoroacetic acid, or acetic acid in hydrobromic acid, or a solution of hydrochloric or hydrobromic acid in an inert solvent, such as tetrahydrofuran, dioxane or methanol), at temperatures between 0 and 100° C., preferably between 0 and 80° C., to form compounds of formula XII, wherein $R_2$, $R_4$ and $R_5$ are as described under formula I above. Such conditions are known to a person skilled in the art. When the protective group is preferably BOC, then the cleavage conditions are preferably, optionally aqueous, hydrogen chloride, or trifluoroacetic acid, optionally in the presence of a solvent, such as 1,4-dioxane, tetrahydrofuran or dichloromethane, at reaction temperatures ranging preferentially from 0° C. to the boiling point of the reaction mixture, or the reaction may be performed under microwave irradiation; followed by vi.) reaction of compounds of formula XII, wherein $R_2$, $R_4$ and $R_5$ are as described under formula I above, with a halogenating agent such as N-chlorosuccinimide (NCS) or N-bromosuccinimide (NBS), or alternatively chlorine or bromine. Such halogenation reactions are carried out in an inert solvent, such as chloroform, carbon tetrachloride, 1,2-dichloroethane, acetic acid, ethers, acetonitrile or N,N-dimethylformamide DMF, at temperatures between 20-200° C., preferably room temperature to 100° C., to form compounds of formula XI, wherein $R_2$, $R_4$ and $R_5$ are as described under formula I above, and in which $X_1$ is halogen, preferably chlorine or bromine. Such reactions are well known to those skilled in the art, and have been described in, for example, Advanced Organic Chemistry: Reactions, Mechanisms, and Structure, Fourth Edition by Jerry March, 1992 (Publisher Wiley New York, N.Y.) p 704-707.

The subgroup of compounds of the formula I-2, wherein Z is X—$R_1$, and wherein X, $R_1$, $R_2$, $R_4$, $R_5$, $R_6$ and A are as described under formula I above, and in which $R_3$ is a leaving group LG, for example a halogen or a sulfonate, preferably chlorine, bromine, iodine or trifluoromethanesulfonate, may be represented by the formula I-2a (scheme 9).

Compounds of formula I, wherein X is SO or $SO_2$, and in which $R_1$, $R_2$, $R_3$, $R_4$, $R_5$, $R_6$ and A are as described under formula I above, can also be prepared by by a Suzuki reaction (scheme 9), which involves for example, reacting compounds of formula I-2a, wherein X is SO or $SO_2$, and in which $R_1$, $R_2$, $R_4$, $R_5$, $R_6$ and A are as described under formula I above, and in which LG is a leaving group, for example a halogen or a sulfonate, preferably chlorine, bromine, iodine or trifluoromethanesulfonate, with compounds of formula XVIII, wherein $R_3$ is as defined above, and wherein $Y_{b1}$ can be a boron-derived functional group, such as for example $B(OH)_2$ or $B(OR_{b1})_2$ wherein $R_{b1}$ can be a $C_1$-$C_4$alkyl group or the two groups $OR_{b1}$ can form together with the boron atom a five or six-membered ring, as for example a pinacol boronic ester. The reaction may be catalyzed by a palladium based catalyst, for example tetrakis(triphenylphosphine)-palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)]palladium (III) (XPhos palladacycle), in presence of a base, like sodium carbonate, tripotassium phosphate or cesium fluoride, in a solvent or a solvent mixture, like, for example dioxane, acetonitrile, N,N-dimethylformamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in *J. Orgmet. Chem.* 576, 1999, 147-168.

Alternatively, compounds of formula I, wherein X is SO or $SO_2$, may be prepared by a Stille reaction between compounds of formula XVIIIa, wherein $R_3$ is as defined above, and wherein $Y_{b2}$ is a trialkyl tin derivative, preferably tri-n-butyl tin or tri-methyl tin, and compounds of formula I-2a, wherein X is SO or $SO_2$, and in which $R_1$, $R_2$, $R_4$, $R_5$, $R_6$ and A are as described under formula I above, and in which LG is a leaving group, for example a halogen or a sulfonate, preferably chlorine, bromine, iodine or trifluoromethanesulfonate. Such Stille reactions are usually carried out in the presence of a palladium catalyst, for example tetrakis(triphenylphosphine)palladium(0), or bis(triphenylphosphine) palladium(II) dichloride, in an inert solvent such as N,N-dimethylformamide, acetonitrile, toluene or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

Scheme 9

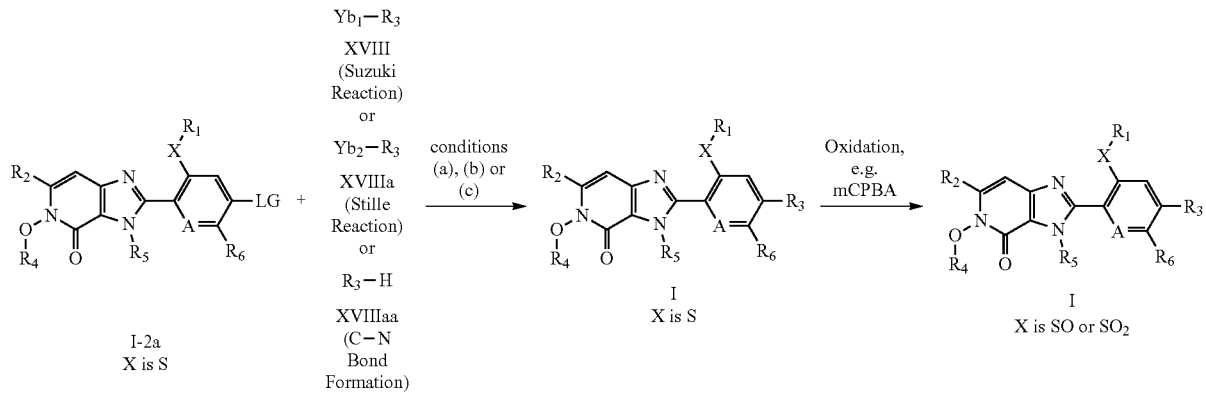

-continued

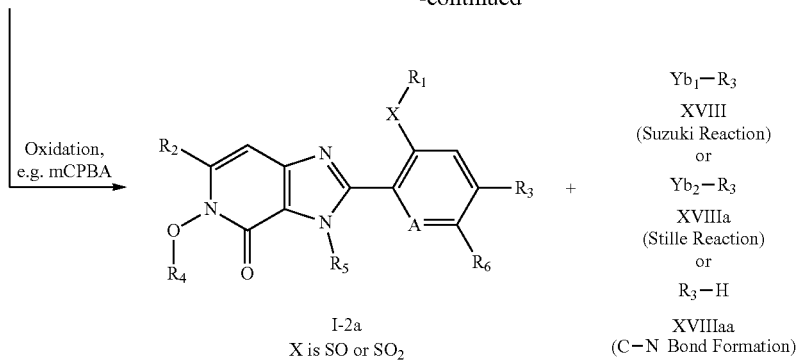

I-2a
X is SO or SO$_2$

XVIII
(Suzuki Reaction)
or
Yb$_2$—R$_3$
XVIIIa
(Stille Reaction)
or
R$_3$—H
XVIIIaa
(C—N Bond Formation)

conditions
(a), (b) or (c)

(a) Suzuki reaction: Pd cat. (e.g. Pd(PPh$_3$)$_4$ or Pd(dppf)Cl$_2$), base (e.g. Na$_2$CO$_3$), solvent (e.g. 1,2-dimethoxyethane/water), 25-180° C.
(b) Stille reaction: Pd cat. (e.g. Pd(PPh$_3$)$_4$ or Pd(PPh$_3$)Cl$_2$), solvent (e.g. toluene), 25-180° C.
(c) C—N bond formation: Base (e.g. K$_2$CO$_3$ or Cs$_2$CO$_3$), optional presence of CuI, optional additive (such as N,N'-dimethylethylenediamine), solvent (e.g. N,N-dimethylformamide DMF or N-methylpyrrolidone NMP), 25-180° C.

When R$_3$ is a five-membered aromatic ring system linked via a nitrogen atom to the ring which contains the group A, then compounds of formula I, wherein X is SO or SO$_2$, may be prepared from compounds of formula I-2a, wherein X is SO or SO$_2$, and in which R$_1$, R$_2$, R$_4$, R$_5$, R$_6$ and A are as described under formula I above, and in which LG is a leaving group, for example a halogen or a sulfonate, preferably chlorine, bromine, iodine or trifluoromethanesulfonate, by reaction with a heterocycle R$_3$—H (which contains an appropriate NH functionality) XVIIIaa (for example XVIIIaa is 1H-1,2,4-triazole), wherein R$_3$ is as defined above, in the presence of a base, such as potassium carbonate K$_2$CO$_3$ or cesium carbonate Cs$_2$CO$_3$, optionally in the presence of a copper catalyst, for example copper(I) iodide, with or without an additive such as L-proline, N,N'-dimethylcyclohexane-1,2-diamine or N,N'-dimethylethylenediamine, in an inert solvent such as N-methylpyrrolidone NMP or N,N-dimethylformamide DMF at temperatures between 30-150° C., optionally under microwave irradiation.

Oxidation of compounds of formula I-2a, wherein X is (sulfide), and in which R$_1$, R$_2$, R$_4$, R$_5$, R$_6$ and A are as described under formula I above, and in which LG is a leaving group, for example a halogen or a sulfonate, preferably chlorine, bromine, iodine or trifluoromethanesulfonate, with a suitable oxidizing agent, into compounds of formula I-2a, wherein X is SO or SO$_2$, may be achieved under conditions already described above.

A large number of compounds of the formula XVIII, XVIIIa and XVIIIaa are commercially available or can be prepared by those skilled in the art.

Alternatively, compounds of formula I, wherein X is SO or SO$_2$, may be prepared from compounds of formula I-2a, wherein X is S (sulfide) by involving the same chemistry as described above, but by changing the order of the steps (i.e. by running the sequence I-2a (X is S) to I (X is S) via Suzuki, Stille or C—N bond formation, followed by an oxidation step to form I (X is SO or SO$_2$).

The subgroup of compounds of the formula I-2, wherein Z is X—R$_1$, and wherein X, R$_1$, R$_2$, R$_4$, R$_5$, R$_3$ and A are as described under formula I above, and in which R$_6$ is a leaving group LG, for example a halogen or a sulfonate, preferably chlorine, bromine, iodine or trifluoromethanesulfonate, may be represented by the formula I-2b (scheme 10).

Scheme 10

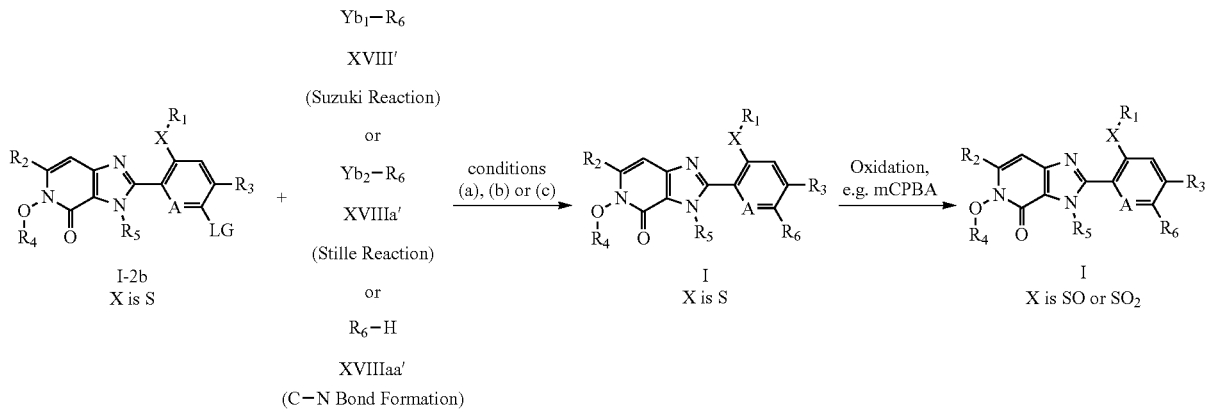

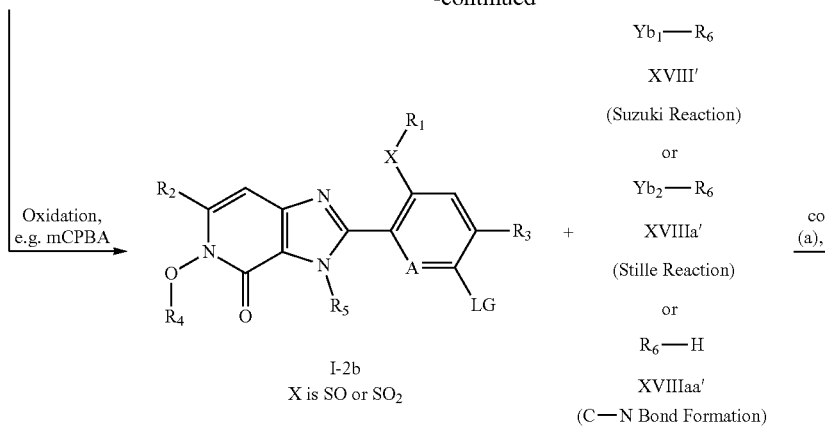

I-2b
X is SO or SO₂

(a) Suzuki reaction: Pd cat. (e.g. Pd(PPh₃)₄ or Pd(dppf)Cl₂), base (e.g. Na₂CO₃), solvent (e.g. 1,2-dimethoxyethane/water), 25 - 180° C.
(b) Stille reaction: Pd cat. (e.g. Pd(PPh₃)₄ or Pd(PPh₃)Cl₂), solvent (e.g. toluene), 25 - 180° C.
(c) C—N bond formation: Base (e.g. K₂CO₃ or Cs₂CO₃), optional presence of CuI, optional additive (such as N, N'-dimethylethylenediamine), solvent (e.g. N, N-dimethylformamide DMF or N-methylpyrrolidone NMP), 25 - 180° C.

The chemistry described previously in scheme 9 can be applied analogously for the preparation of compounds of formula I, wherein X is S, SO or SO₂, and in which $R_1$, $R_2$, $R_3$, $R_4$, $R_5$, $R_6$ and A are as described under formula I above, by starting from compounds of the formula I-2b, wherein X is S, SO or SO₂, and in which $R_1$, $R_2$, $R_4$, $R_5$, $R_3$ and A are as described under formula I above, and in which LG is a leaving group, for example a halogen or a sulfonate, preferably chlorine, bromine, iodine or trifluoromethanesulfonate (scheme 10). Substituent definitions mentioned previously in scheme 9 are also valid for the compounds/reagents shown in scheme 10.

Compounds of formula I-2a and I-2b, wherein the substituents are as defined above, may be prepared (scheme 10a) by reaction between compounds of formula II, respectively IIa, wherein the substituents are as defined above with the particular situation that either $R_3$ or $R_6$ are replaced with LG, which is as defined above, and in which $X_{00}$ is as described above ($X_{00}$ typically is chlorine), and compounds of formula III, or a salt thereof, wherein $R_4$, $R_5$ and $R_2$ are as described under formula I above, under similar conditions as for the preparation of compounds of formula Ia from compounds of formula II/IIa and III described above (see schemes 1 and 2; see also scheme 6).

Scheme 10a

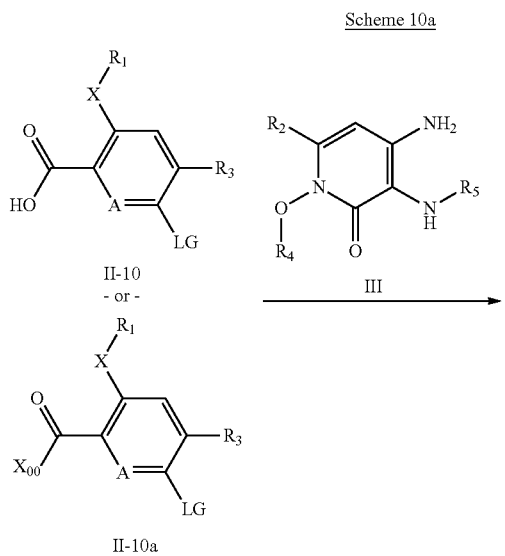

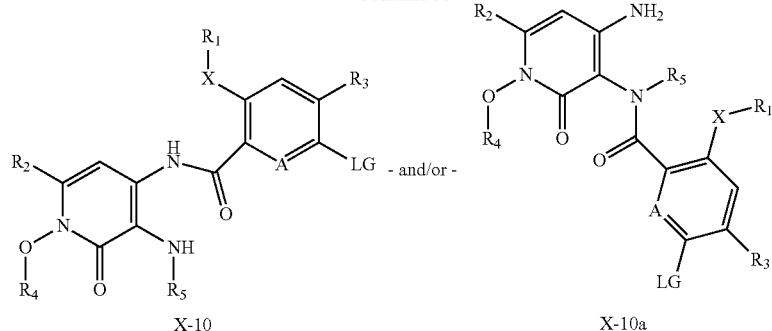

X-10    -and/or-    X-10a

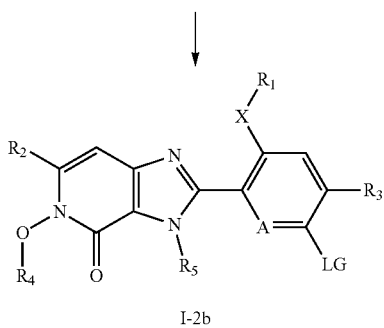

I-2b

This is exemplified in scheme 10a for the synthesis of compounds of formula I-2b, wherein X, $R_1$, $R_2$, $R_4$, $R_5$, $R_3$ and A are as described under formula I above, and in which LG is a leaving group, for example a halogen or a sulfonate, preferably chlorine, bromine, iodine or trifluoromethanesulfonate, that may be prepared by reaction between compounds of formula II-10, respectively their activated form II-10a, wherein X, $R_1$, $R_3$ and A are as described under formula I above, and in which LG is a leaving group, for example a halogen or a sulfonate, preferably chlorine, bromine, iodine or trifluoromethanesulfonate, and in which $X_{00}$ is as described above ($X_{00}$ typically is chlorine), and compounds of formula III, or a salt thereof, wherein $R_4$, $R_5$ and $R_2$ are as described under formula I above, via compounds of formula X-10 and X-10a.

The subgroup of compounds of the formula I-2b, wherein A is N, and wherein X, $R_1$, $R_2$, $R_4$, $R_5$ and $R_3$ are as described under formula I above, and in which $R_6$ is a leaving group LG, for example a halogen, preferably chlorine or bromine, may be represented by the formula I-2b' (scheme 10b). Compounds of the formula I-2b' can also be prepared as illustrated:

Scheme 10b

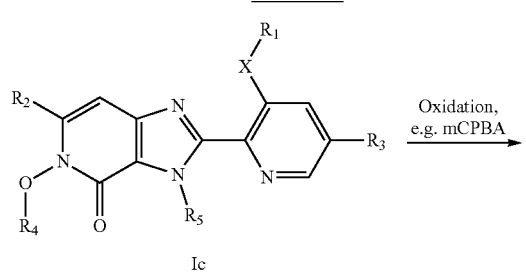

Ic

→ Oxidation, e.g. mCPBA

-continued

Id
N-oxide of Ic

→ Halogenation, e.g. POCl₃

I-2b'

Compounds of the formula I, wherein A is N, and in which $R_6$ is hydrogen, and wherein X, $R_1$, $R_2$, $R_3$, $R_4$ and $R_5$ are as described under formula I above (represented by the formula Ic), can be oxidized to their corresponding N-oxides Id under standard conditions already detailed above (for example, m-chloroperoxybenzoic acid (mCPBA) in dichloromethane at temperatures between room temperature and refluxing conditions), or alternatively by using a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 00/15615. Compounds of the formula I-2b', wherein X, $R_1$, $R_2$, $R_4$, $R_5$ and $R_3$ are as described under formula I above, and in which LG is a leaving group, for example a halogen, preferably chlorine or bromine, can be prepared by reacting N-oxide compounds of the formula Id, wherein X, $R_1$, $R_2$, $R_3$, $R_4$ and $R_5$ are as described under formula I above, with reagents such as, for example, phosphorus oxychloride or phosphorus trichloride, under conditions known to a person skilled in the art, and described in, for example, Scriven, E. F. V. (1984). "Pyridines and their Benzo Derivatives: (ii) Reactivity at Ring Atoms". In Katritzky, Alan R.; Rees, Charles Wayne; Meth-Cohn, Otto. Comprehensive Heterocyclic Chemistry: The Structure, Reactions, Synthesis and Uses of Heterocyclic Compounds. 2. Pergamon Press. pp. 165-314.

The subgroup of compounds of the formula I, wherein X, $R_1$, $R_2$, $R_4$, $R_5$, $R_6$ and A are as described under formula I above, and in which $R_3$ is $C_3$-$C_6$cycloalkyl which can be mono- or polysubstituted by substituents selected from the group consisting of halogen, $C_1$-$C_4$alkyl, $C_1$-$C_4$haloalkyl, cyano and $C_1$-$C_4$alkoxy, may be prepared by methods described above (in particular, compounds of formula I wherein $R_3$ is cyclopropyl may be prepared from compounds of formula I-2a, wherein LG is for example bromine, by a Suzuki reaction involving cyclopropylboronic acid according to descriptions made in scheme 9). For the special case of compounds of formula I wherein $R_3$ is $C_3$-$C_6$cycloalkyl substituted by cyano (represented by compounds of formula I-2e), the compounds can be prepared by the methods shown in scheme 11.

Scheme 11

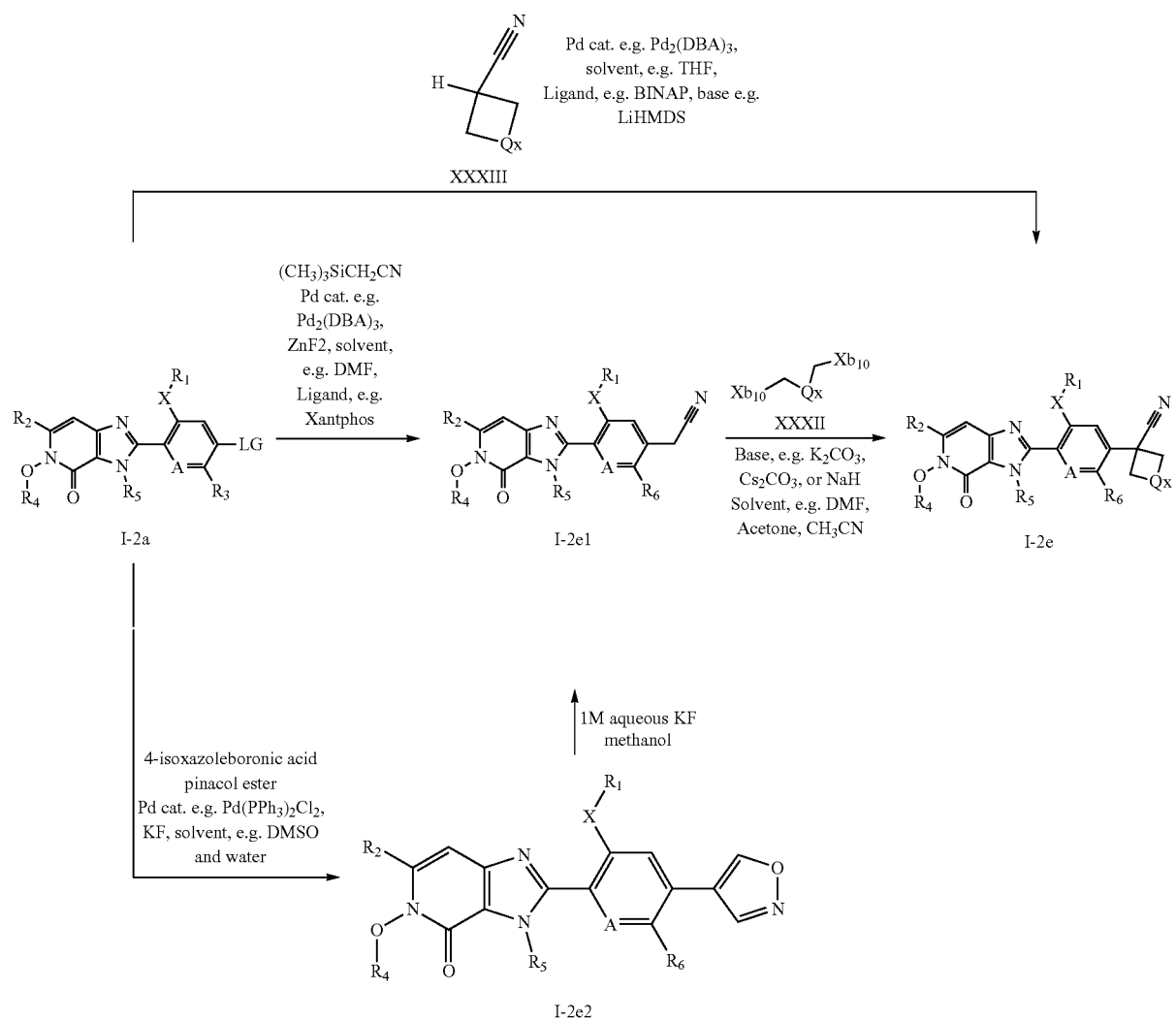

Treatment of compounds of formula I-2a, wherein X, $R_1$, $R_2$, $R_4$, $R_5$, $R_6$ and A are as described under formula I above, and in which LG is a leaving group, for example a halogen or a sulfonate, preferably chlorine, bromine, iodine or trifluoromethanesulfonate, with trimethylsilyl-acetonitrile TMSCN, in the presence of zinc(II)fluoride $ZnF_2$, and a palladium(0)catalyst such as tris(dibenzylideneacetone)dipalladium(0)-chloroform adduct ($Pd_2(dba)_3$), with a ligand, for example Xantphos, in an inert solvent, such as N,N-dimethylformamide DMF at temperatures between 100-180° C., optionally under microwave heating, may lead to compounds of formula I-2e1, wherein X, $R_1$, $R_2$, $R_4$, $R_5$, $R_6$ and A are as described under formula I above. Such chemistry has been described in the literature, e.g. in *Org. Lett.* 16(24), 6314-6317, 2014. Alternatively, reaction of compounds of formula I-2a, wherein X, $R_1$, $R_2$, $R_4$, $R_5$, $R_6$ and A are as described under formula I above, and in which LG is a leaving group, for example a halogen or a sulfonate, preferably chlorine, bromine, iodine or trifluoromethanesulfonate, with 4-isoxazoleboronic acid or 4-isoxazoleboronic acid pinacol ester, in the presence of potassium fluoride KF, and a palladium catalyst such as bis(triphenylphosphine)palladium(II) dichloride Pd(PPh$_3$)$_2$Cl$_2$, in an inert solvent, such as dimethylsulfoxide DMSO, optionally in mixture with water, at temperatures between 40-150° C., optionally under microwave heating, may lead to compounds of formula I-2e2, wherein X, R$_1$, R$_2$, R$_4$, R$_5$, R$_6$ and A are as described under formula I above. Reaction of compounds of formula I-2e2, wherein X, R$_1$, R$_2$, R$_4$, R$_5$, R$_6$ and A are as described under formula I above, with aqueous potassium fluoride KF (concentration between 0.5 and 3M, preferably 1M), in an inert solvent, such as dimethylsulfoxide DMSO or methanol, at temperatures between 20-150° C., optionally under microwave heating, may also lead to compounds of formula I-2e1, wherein X, R$_1$, R$_2$, R$_4$, R$_5$, R$_6$ and A are as described under formula I above. Such chemistry has been described in the literature, e.g. in J Am Chem Soc 2011, 133, 6948-6951.

Compounds of formula I-2e1, wherein X, R$_1$, R$_2$, R$_4$, R$_5$, R$_6$ and A are as described under formula I above, can be further treated with compounds of formula XXXII, wherein Qx is a direct bond or is (CH$_2$)$_n$ and n is 1, 2 or 3, and in which Xb$_{10}$ is a leaving group such as a halogen (preferably chlorine, bromine or iodine), in the presence of a base such as sodium hydride, sodium carbonate, potassium carbonate K$_2$CO$_3$, or cesium carbonate Cs$_2$CO$_3$, in an inert solvent such as N,N-dimethylformamide DMF, acetone, or acetonitrile, at temperatures between 0-120° C., to give compounds of formula I-2e, wherein X, R$_1$, R$_2$, R$_4$, R$_5$, R$_6$ and A are as described under formula I above, and in which Qx is a direct bond or is (CH$_2$)$_n$ and n is 1, 2 or 3. Alternatively, compounds of formula I-2e can be prepared directly from compounds of formula I-2a by treatment with compounds of formula XXXIII, wherein Qx is as described in XXXII, in presence of a catalyst such as Pd$_2$(dba)$_3$, with a ligand, such as BINAP, a strong base such as lithium hexamethyldisilazane LiHMDS, in an inert solvent such as tetrahydrofuran THF, at temperatures between 30-80° C. Such chemistry has been described in, for example, *J. Am. Chem. Soc.* 127(45), 15824-15832, 2005.

Yet another method to prepare compounds of formula I-2e1 from compounds of formula I-2a is shown below (scheme 12). Reaction of compounds of formula I-2a, wherein X, R$_1$, R$_2$, R$_4$, R$_5$, R$_6$ and A are as described under formula I above, and in which LG is a leaving group, for example a halogen or a sulfonate, preferably chlorine, bromine, iodine or trifluoromethanesulfonate, with reagents of the formula XXXIV, wherein Rx is C$_1$-C$_6$alkyl, in the presence of a base, such as sodium carbonate, potassium carbonate or cesium carbonate, or sodium hydride, sodium methoxide or ethoxide, potassium tert-butoxide, optionally under palladium (for example involving Pd(PPh$_3$)$_2$Cl$_2$) or copper (for example involving CuI) catalysis, in a appropriate solvent such as for example toluene, dioxane, tetrahydrofuran, acetonitrile, N,N-dimethylformamide, N,N-dimethylacetamide, N-methyl-2-pyrrolidone NMP or dimethylsulfoxide DMSO, optionally in presence of a phase transfer catalyst PTC, such as for example tetrabutyl ammonium bromide or triethyl benzyl ammonium chloride TEBAC, at temperatures between room temperature and 180° C., may lead to compounds of formula I-2e3, wherein X, R$_1$, R$_2$, R$_4$, R$_5$, R$_6$ and A are as described under formula I above, and in which Rx is C$_1$-C$_6$alkyl. Similar chemistry has been described in, for example, Synthesis 2010, No. 19, 3332-3338.

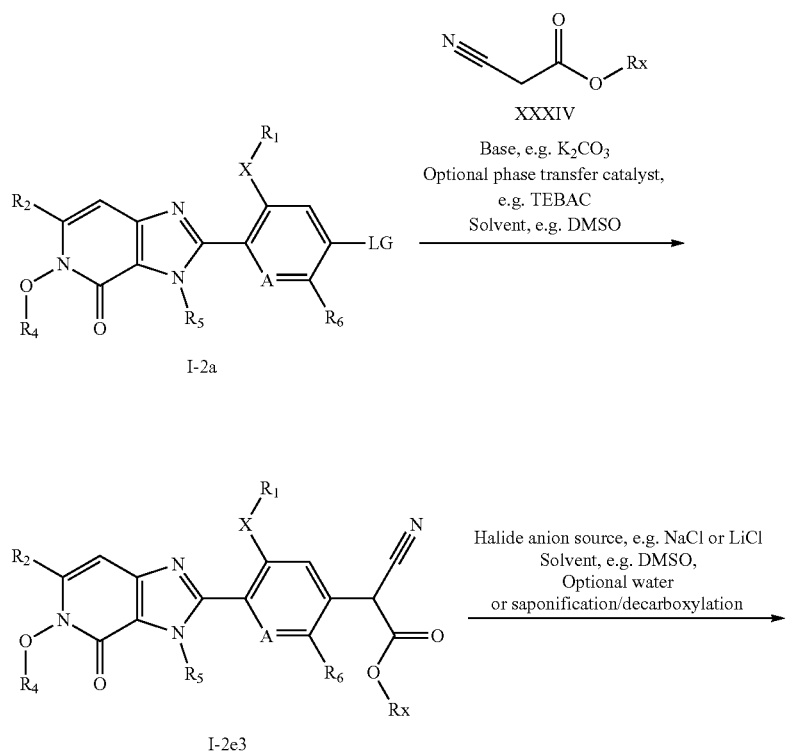

Scheme 12

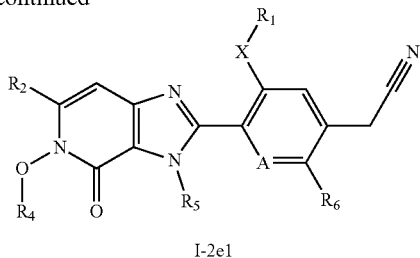

I-2e1

Compounds of formula I-2e1, wherein X, $R_1$, $R_2$, $R_4$, $R_5$, $R_6$ and A are as described under formula I above, may be prepared by saponification/decarboxylation of the compounds of formula I-2e3, wherein X, $R_1$, $R_2$, $R_4$, $R_5$, $R_6$ and A are as described under formula I above, and in which Rx is $C_1$-$C_6$alkyl, under conditions known to a person skilled in the art (using for example conditions such as: aqueous sodium, potassium or lithium hydroxide in methanol, ethanol, tetrahydrofuran or dioxane at room temperature, or up to refluxing conditions; followed by acificationi of the reaction mixture under standard aqueous acid conditions). Alternatively, treating compounds of formula I-2e3 with halide anions, preferably chloride anions, originating from, for example, lithium chloride or sodium chloride, in solvents such as N,N-dimethylformamide, N,N-dimethylacetamide, N-methyl-2-pyrrolidone or dimethylsulfoxide DMSO, optionally in presence of additional water, may also generate the compounds of formula I-2e1. The reaction temperature for such a transformation (Krapcho O-dealkyla-tion/decarboxylation) range preferentially from 20° C. to the boiling point of the reaction mixture, or the reaction may be performed under microwave irradiation. Similar chemistry has been described in, for example, Synthesis 2010, No. 19, 3332-3338.

Alternatively compounds of formula I-2e, wherein X, $R_1$, $R_2$, $R_4$, $R_5$, $R_6$ and A are as described under formula I above, and in which Qx is a direct bond or is $(CH_2)_n$ and n is 1, 2 or 3, can also be prepared as shown in schemes 13 and 14.

Compounds of formula II-4, wherein X, $R_1$, $R_6$ and A are as described under formula I above, and in which Qx is a direct bond or is $(CH_2)_n$ and n is 1, 2 or 3, and wherein $Rx_1$ is $C_1$-$C_6$alkyl, can be prepared (scheme 13) from compounds of formula II-1, wherein X, $R_1$, $R_6$ and A are as described under formula I above, and in which LG is a leaving group, for example a halogen or a sulfonate, preferably chlorine, bromine, iodine or trifluoromethane-sulfonate, and wherein $Rx_1$ is $C_1$-$C_6$alkyl, in analogy to chemistry described and discussed in schemes 11 and 12, via intermediates II-2, II-3, II-5, or directly, and involving said reaction conditions and reagents of formula XXXII or XXXIII.

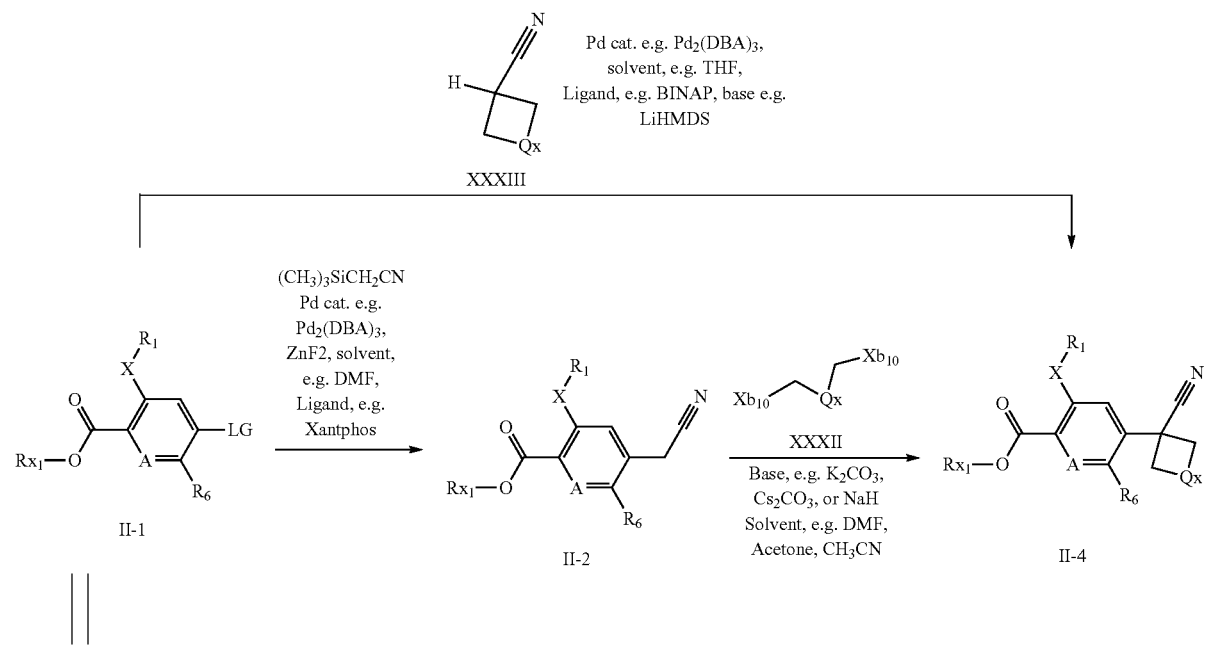

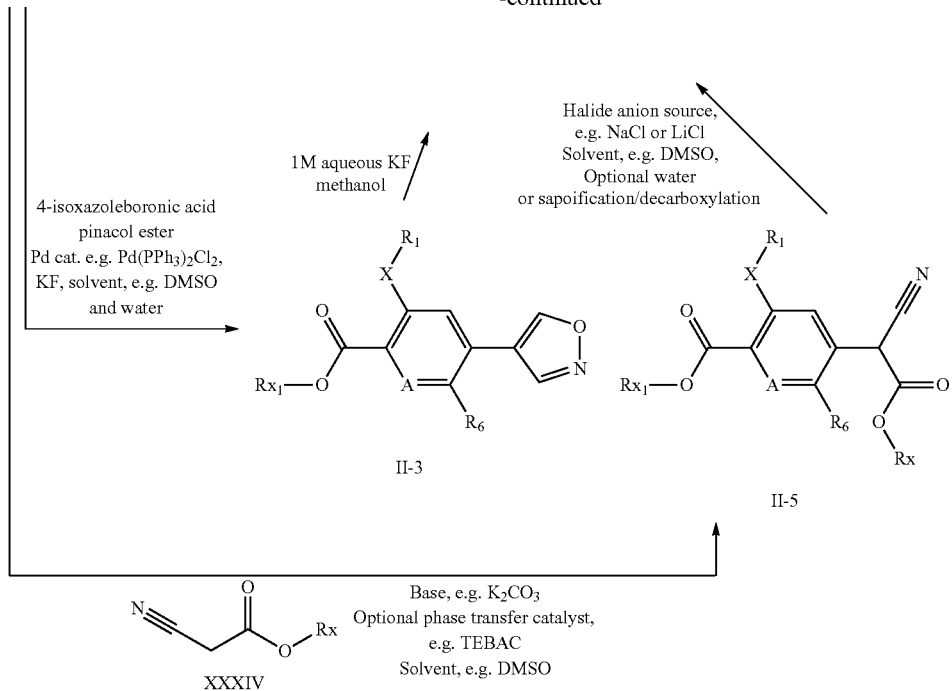

Compounds of formula II-6, wherein X, $R_1$, $R_6$ and A are as described under formula I above, and in which Qx is a direct bond or is $(CH_2)_n$ and n is 1, 2 or 3, can be prepared (scheme 14) by saponification of the compounds of formula II-4, wherein X, $R_1$, $R_6$ and A are as described under formula I above, and in which Qx is a direct bond or is $(CH_2)_n$ and n is 1, 2 or 3, and wherein $Rx_1$ is $C_1$-$C_6$alkyl, under conditions known to a person skilled in the art (using for example conditions such as: sodium, potassium or lithium hydroxide in methanol, ethanol, tetrahydrofuran or dioxane, optionally in presence of water, at room temperature, or up to refluxing conditions).

Scheme 14

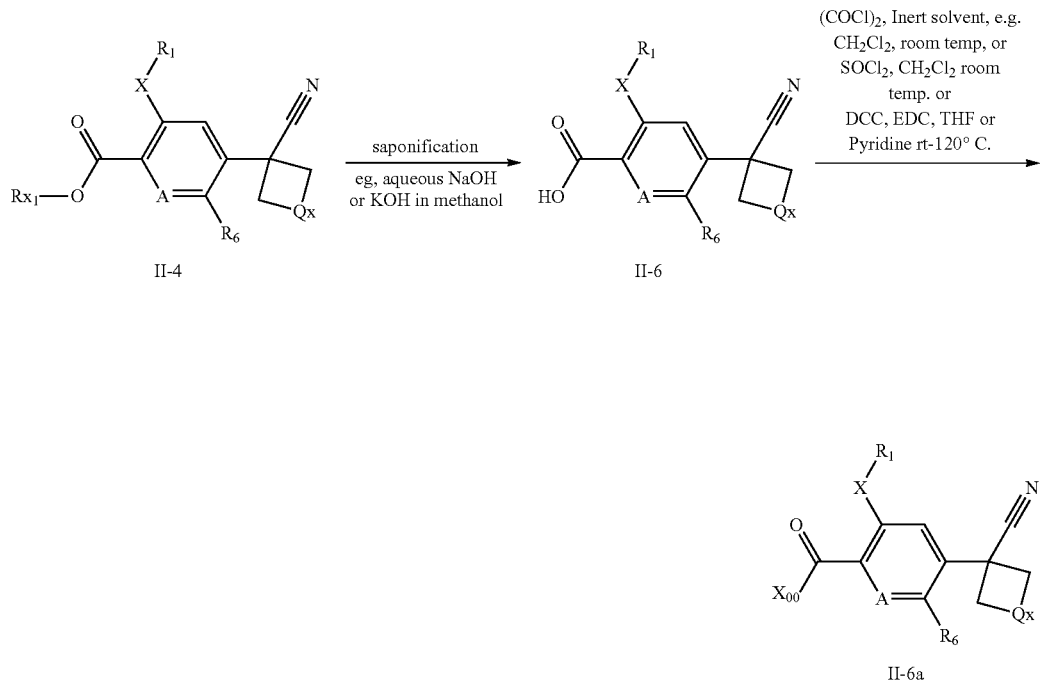

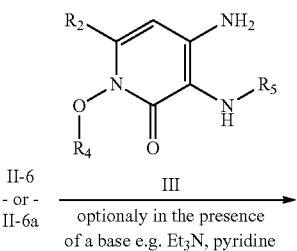

II-6
- or -
II-6a

III optionaly in the presence
of a base e.g. Et$_3$N, pyridine

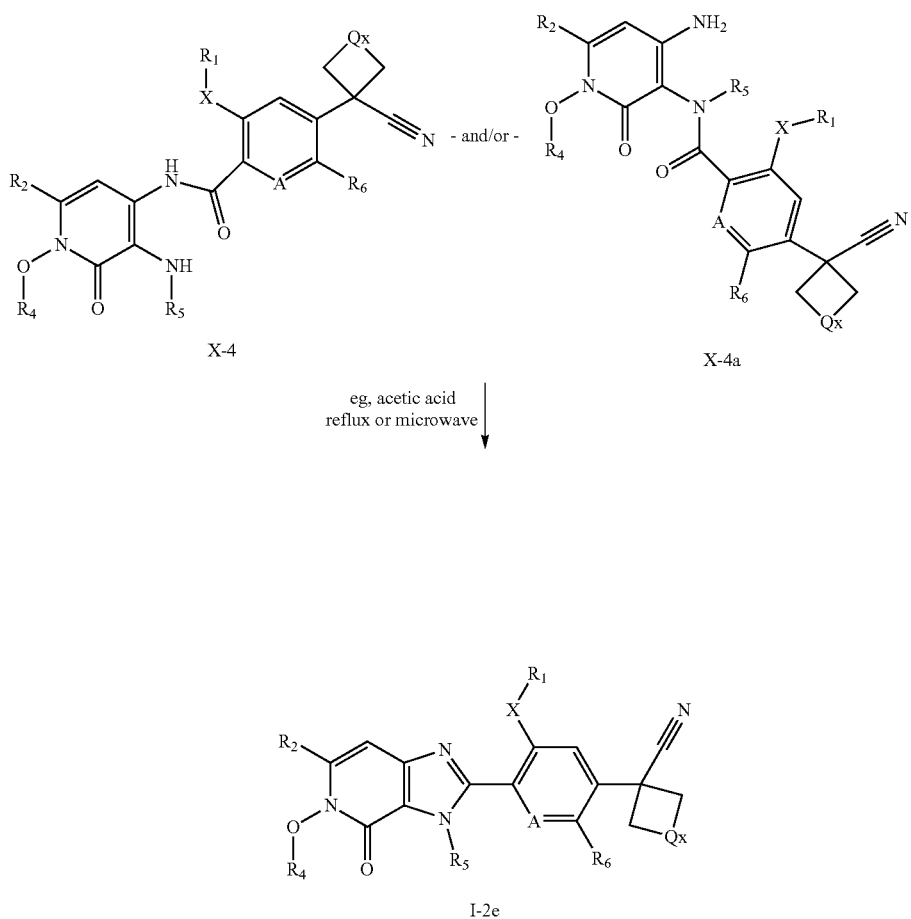

Compounds of formula I-2e, wherein X, R$_1$, R$_2$, R$_4$, R$_5$, R$_6$ and A are as described under formula I above, and in which Qx is a direct bond or is (CH$_2$)$_n$ and n is 1, 2 or 3, can be prepared (scheme 14) by reaction between compounds of formula II-6, respectively their activated form II-6a, wherein X, R$_1$, R$_6$ and A are as described under formula I above, and in which Qx is a direct bond or is (CH$_2$)$_n$ and n is 1, 2 or 3, and in which X$_{00}$ is as described above (X$_{00}$ typically is chlorine), and compounds of formula III, or a salt thereof, wherein R$_4$, R$_5$ and R$_2$ are as described under formula I above, under similar conditions as for the preparation of compounds of formula Ia from compounds of formula II/IIa and III described above (see schemes 1 and 2; see also scheme 6), and via compounds of formula X-4 and X-4a.

The subgroup of compounds of the formula I, wherein X, R$_1$, R$_2$, R$_4$, R$_5$, R$_6$ and A are as described under formula I above, and in which R$_3$ is C$_1$-C$_4$alkyl, may be prepared by methods described above (for example, compounds of formula I wherein R$_3$ is isopropyl may be prepared from compounds of formula I-2a, wherein LG is for example bromine, by a Suzuki reaction involving isopropylboronic acid pinacol ester according to descriptions made in scheme 9). For the special case of compounds of formula I wherein R$_3$ is C$_1$-C$_4$alkyl monosubstituted by cyano, preferably isopropyl monosubstituted by cyano (represented by compounds of formula I-2f), the compounds can be prepared by the methods shown in scheme 15.

Scheme 15

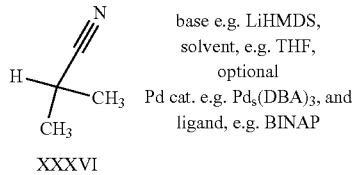

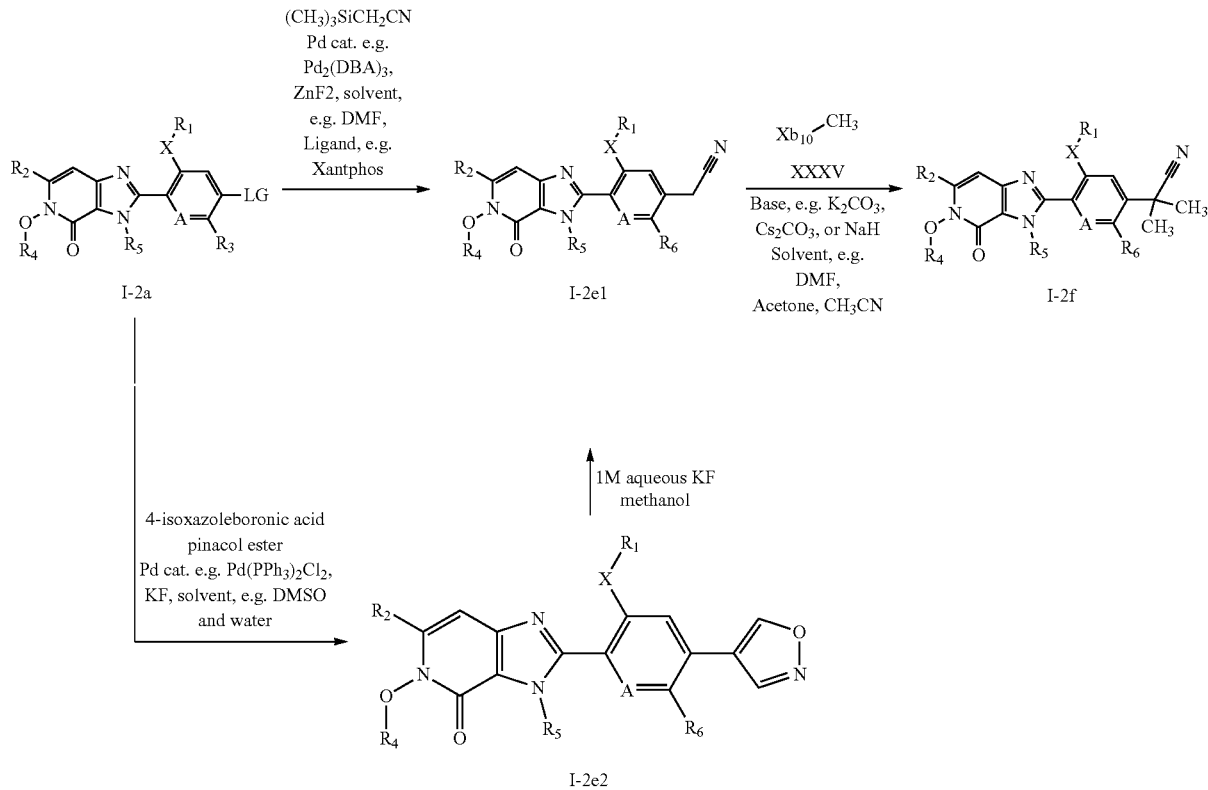

Compounds of formula I-2f, wherein X, $R_1$, $R_2$, $R_4$, $R_5$, $R_6$ and A are as described under formula I above, may be prepared by reacting compounds of formula I-2e1, wherein X, $R_1$, $R_2$, $R_4$, $R_5$, $R_6$ and A are as described under formula I above, with reagents of formula XXXV, wherein $Xb_{10}$ is a leaving group such as a halogen (preferably chlorine, bromine or iodine), alternatively with dimethylsulfate, in the presence of a base such as sodium hydride, sodium carbonate, potassium carbonate $K_2CO_3$, or cesium carbonate $Cs_2CO_3$, in an inert solvent such as N,N-dimethylformamide DMF, acetone, or acetonitrile, at temperatures between 0-120° C. Alternatively, compounds of formula I-2f may be prepared directly from compounds of formula I-2a by treatment with compounds of formula XXXVI, optionally in presence of a catalyst such as $Pd_2(dba)_3$, with a ligand, such as BINAP, and a strong base such as lithium hexamethyldisilazane LiHMDS, in an inert solvent such as tetrahydrofuran THF, dioxane or 1,2-dimethoxyethane, at temperatures between −30° C. to 80° C. Such chemistry has been described in, for example, *J. Am. Chem. Soc.* 127(45), 15824-15832, 2005. Options to prepare compounds of formula I-2e1 from compounds I-2a, possibly via intermediates of formula I-2e2 or I-2e3, have been detailed above in schemes 11 and 12.

Alternatively, compounds of formula I-2f, wherein X, $R_1$, $R_2$, $R_4$, $R_5$, $R_6$ and A are as described under formula I above, can also be prepared as shown in schemes 16 and 17.

Compounds of formula II-7, wherein X, $R_1$, $R_6$ and A are as described under formula I above, and wherein $Rx_1$ is $C_1$-$C_6$alkyl, can be prepared (scheme 16) by reacting compounds of formula II-2, wherein X, $R_1$, $R_6$ and A are as described under formula I above, and in which $Rx_1$ is $C_1$-$C_6$alkyl, with reagents of formula XXXV, wherein $Xb_{10}$ is a leaving group such as a halogen (preferably chlorine, bromine or iodine), alternatively with dimethylsulfate, in the presence of a base such as sodium hydride, sodium carbonate, potassium carbonate $K_2CO_3$, or cesium carbonate $Cs_2CO_3$, in an inert solvent such as N,N-dimethylformamide DMF, acetone, or acetonitrile, at temperatures between 0-120° C. Alternatively, compounds of formula II-7 may be prepared directly from compounds of formula II-1 by treatment with compounds of formula XXXVI, optionally in presence of a catalyst such as $Pd_2(dba)_3$, with a ligand, such as BINAP, and a strong base such as lithium hexamethyldisilazane LiHMDS, in an inert solvent such as tetrahydrofuran THF, dioxane or 1,2-dimethoxyethane, at temperatures between −30° C. to 80° C. Such chemistry has been described in, for example, *J. Am. Chem. Soc.* 127(45), 15824-15832, 2005. Options to prepare compounds of formula II-2 from compounds II-1, possibly via intermediates of formula II-3 or II-5, have been detailed above in scheme 13 (see also conditions described in schemes 11 and 12).

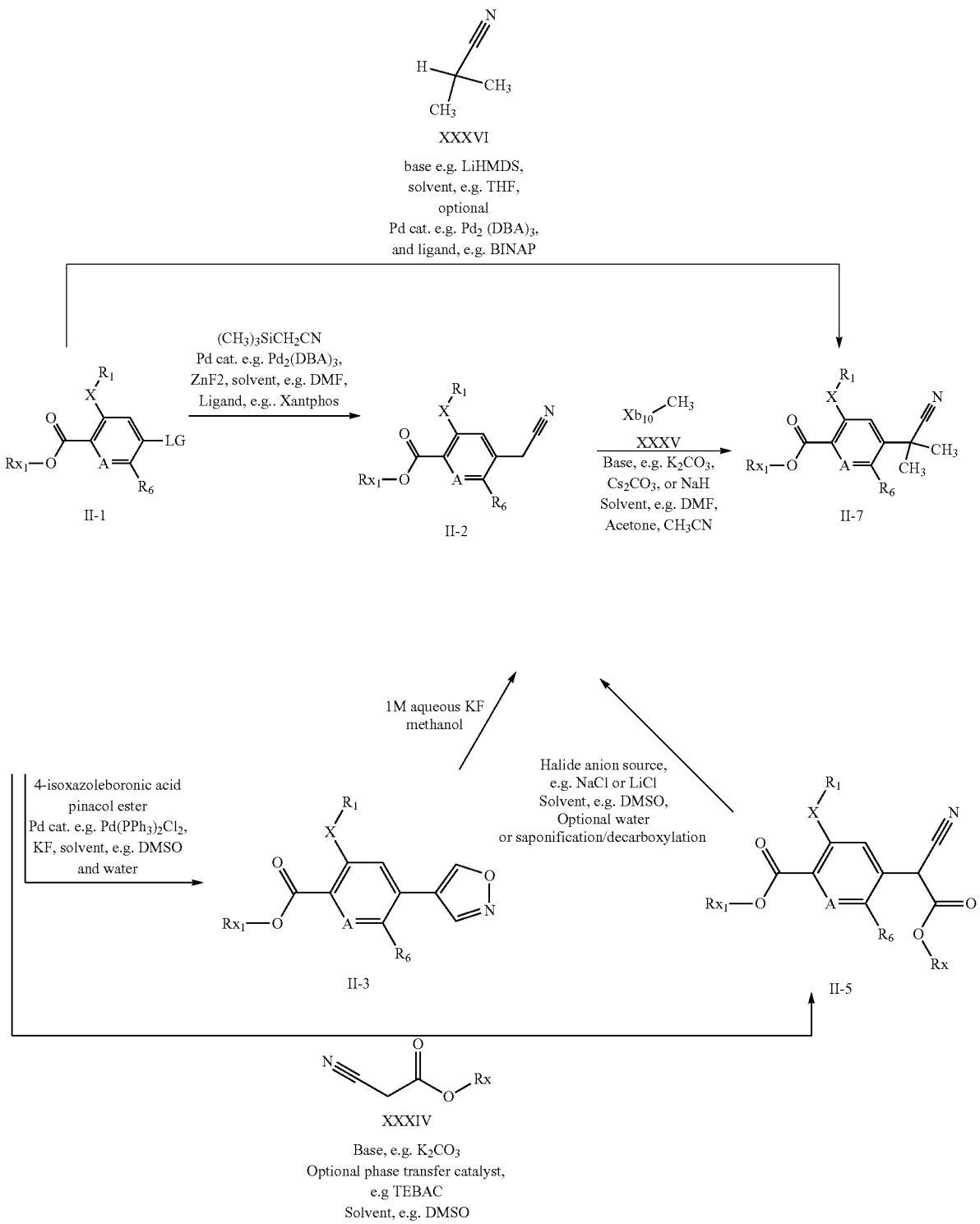

Compounds of formula II-8, wherein X, $R_1$, $R_6$ and A are as described under formula I above, can be prepared (scheme 17) by saponification of the compounds of formula II-7, wherein X, $R_1$, $R_6$ and A are as described under formula I above, and wherein $Rx_1$ is $C_1$-$C_6$alkyl, under conditions known to a person skilled in the art (using for example conditions such as: sodium, potassium or lithium hydroxide in methanol, ethanol, tetrahydrofuran or dioxane, optionally in presence of water, at room temperature, or up to refluxing conditions).

Scheme 17

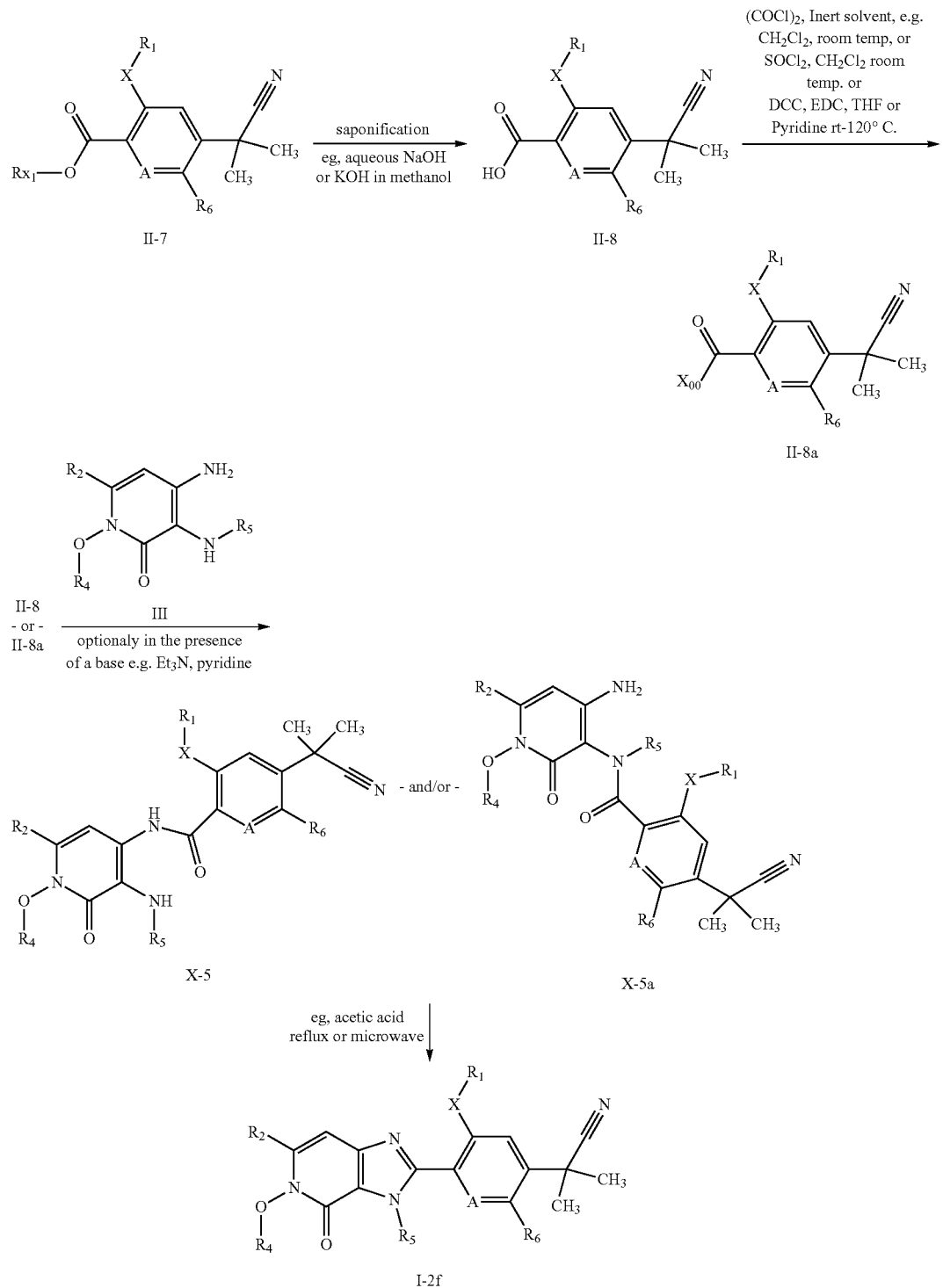

Compounds of formula I-2f, wherein X, $R_1$, $R_2$, $R_4$, $R_5$, $R_6$ and A are as described under formula I above, can be prepared (scheme 17) by reaction between compounds of formula II-8, respectively their activated form II-8a, wherein X, $R_1$, $R_6$ and A are as described under formula I above, and in which $X_{00}$ is as described above ($X_{00}$ typically is chlorine), and compounds of formula III, or a salt thereof, wherein $R_4$, $R_5$ and $R_2$ are as described under formula I above, under similar conditions as for the preparation of compounds of formula Ia from compounds of formula II/IIa and III described above (see schemes 1 and 2; see also schemes 6 and 14), and via compounds of formula X-5 and X-5a.

Compounds of formula I, wherein $R_6$ is labeled as $R_{6(amino)}$, define the particular subgroup of compounds of formula I, wherein $R_6$ is $NR_7R_8$, and in which $R_7$ and $R_8$ are independently hydrogen, $C_1$-$C_4$alkyl or $C_3$-$C_6$cycloalkyl, preferably hydrogen, methyl, ethyl or cyclopropyl. Compounds of formula I-2g, or a salt thereof, wherein $R_6$ is $R_{6(amino)}$, and wherein X, $R_1$, $R_2$, $R_4$, $R_5$, $R_3$ and A are as described under formula I above, suitable solvents (or diluents) such as alcohols, amides, esters, ethers, nitriles and water, particularly preferred are methanol, ethanol, 2,2,2-trifluoroethanol, propanol, iso-propanol, N,N-dimethylformamide, N,N-dimethylacetamide, dioxane, tetrahydrofuran, dimethoxyethane, acetonitrile, ethyl acetate, water or mixtures thereof, optionally in presence of a base, at temperatures between 0-150° C., preferably at temperatures ranging from room temperature to the boiling point of the reaction mixture, optionally under microwave irradiation and optionally in a pressurized vessel.

Compounds of formula I-2h, wherein $R_6$ is $R_{6(amino)}$ as defined above, and in which $R_3$ is halogen (preferably chlorine, bromine or iodine), and wherein X, $R_1$, $R_2$, $R_4$, $R_5$ and A are as described under formula I above, can be prepared (scheme 18) by a halogenation reaction, which involves for example, reacting compounds of formula I-2g, wherein $R_6$ is $R_{6(amino)}$ as defined above, and in which $R_3$ is hydrogen, and wherein X, $R_1$, $R_2$, $R_4$, $R_5$ and A are as described under formula I above, with halogenating reagents

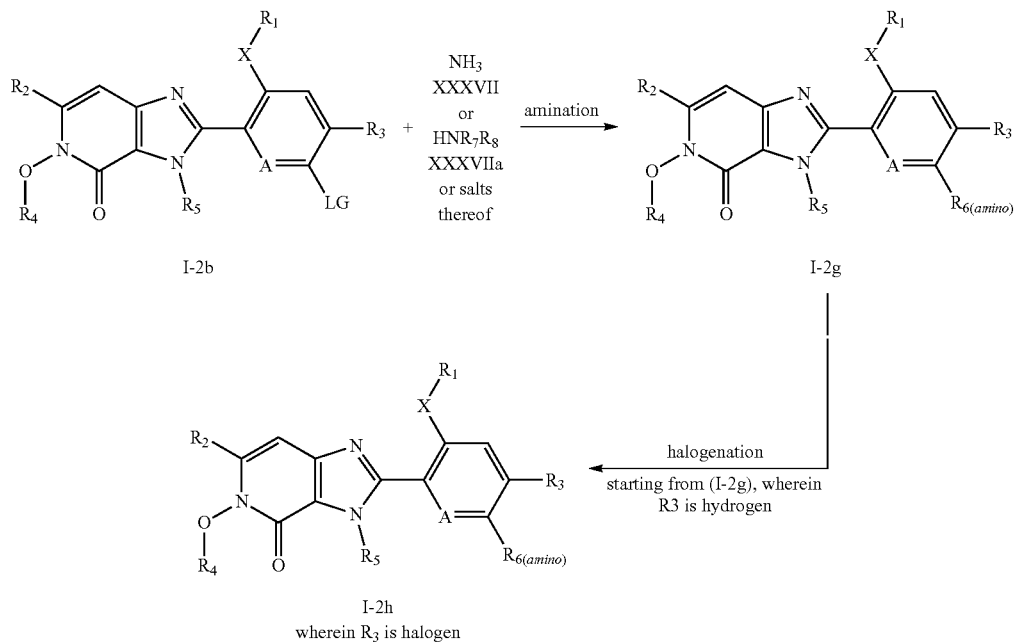

Scheme 18 can be prepared (scheme 18) by an amination reaction, which involves for example, reacting compounds of formula I-2b (see scheme 10), wherein X, $R_1$, $R_2$, $R_4$, $R_5$, $R_3$ and A are as described under formula I above, and in which LG is a leaving group, for example a halogen or a sulfonate, preferably chlorine, bromine, iodine or trifluoromethanesulfonate, with amino reagents of formula XXXVII (ammonia) or formula XXXVIIIa (e.g. methylamine as a representative of $C_1$-$C_4$(cyclo)alkylamines $H_2NR_7$ [$R_8$ is hydrogen)], or dimethylamine as a representative of $C_1$-$C_4$di(cyclo)alkylamines $HNR_7R_8$), or corresponding salts thereof (such as a hydrohalide salt, preferably a hydrochloride or a hydrobromide salt, or any other equivalent salt). The source for the reagent XXXVII may be ammonia $NH_3$ or an ammonia equivalent such as for example ammonium hydroxide $NH_4OH$, ammonium chloride $NH_4Cl$, ammonium acetate $NH_4OAc$, ammonium carbonate $(NH_4)_2CO_3$, and other $NH_3$ surrogates. This transformation is preferably performed in such as N-chlorosuccinimide (NCS), N-bromosuccinimide (NBS) or N-iodosuccinimide (NIS), or alternatively chlorine, bromine or iodine. Such halogenation reactions are carried out in an inert solvent, such as chloroform, carbon tetrachloride, 1,2-dichloroethane, acetic acid, ethers, acetonitrile or N,N-dimethylformamide, at temperatures between 20-200° C., preferably room temperature to 100° C.

Hydroxylamine compounds of formula $H_2NOR_4$ (such as O-methyl hydroxylamine), or a salt thereof (such as a hydrohalide salt, preferably a hydrochloride or a hydrobromide salt, or any other equivalent salt), wherein $R_4$ is as described under formula I above, are either known, commercially available or may be made by methods known to a person skilled in the art.

A large number of compounds of the formula XVIII, XVIIIa, XVIII', XVIIIa', XVIIIaa', XXXII, XXXIII, XXXIV, XXXV, XXXVI and XXXVIIIa are either known, commercially available or may be made by methods known to a person skilled in the art.

Compounds of formula II

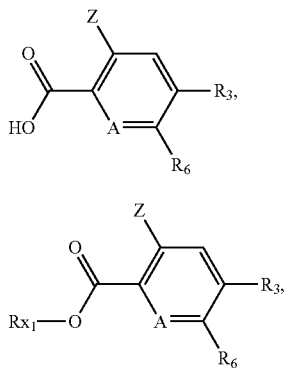

wherein Z is X—$R_1$ or a leaving group, for example a halogen (preferably fluoro or chloro), and wherein X, $R_1$, $R_3$, $R_6$ and A are as described under formula I above, as well as obvious close analogues such as ester derivatives of compounds II (e.g. a methyl or ethyl ester), represented by the formula IIb, wherein $Rx_1$ is $C_1$-$C_6$alkyl, are either known, commercially available (for example 3-ethylsulfanyl-pyridine-2-carboxylic acid) or may be made under conditions known to a person skilled in the art. In particular, $C_1$-$C_6$alkyl esters IIb of acid compounds of the formula II may be obtained by treating said acids II with the appropriate alcohols $Rx_1$-OH, in presence of a catalytic amount of acid (e.g. sulfuric acid), under standard conditions. Respectively, saponification under standard conditions (scheme 14) of esters of formula IIb will generate the acid of formula II.

Similar considerations apply to the compounds of formula II-1, respectively II-1'

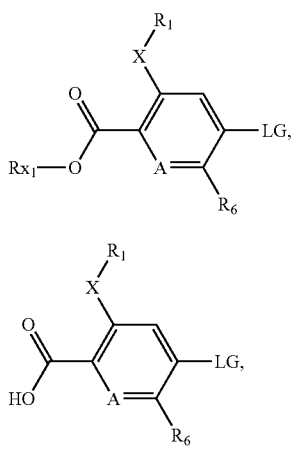

wherein X, $R_1$, $R_6$ and A are as described under formula I above, and in which $Rx_1$ is $C_1$-$C_6$alkyl, and wherein LG is a leaving group, for example a halogen or a sulfonate, preferably chlorine, bromine, iodine or trifluoromethanesulfonate. For example, 5-bromo-3-ethylsulfanyl-pyridine-2-carboxylic acid is known from WO 2016/005263, or methyl 4-bromo-2-ethylsulfanyl-benzoate from WO 2016/023954.

Similar considerations apply also to the compounds of formula II-10, respectively II-10'

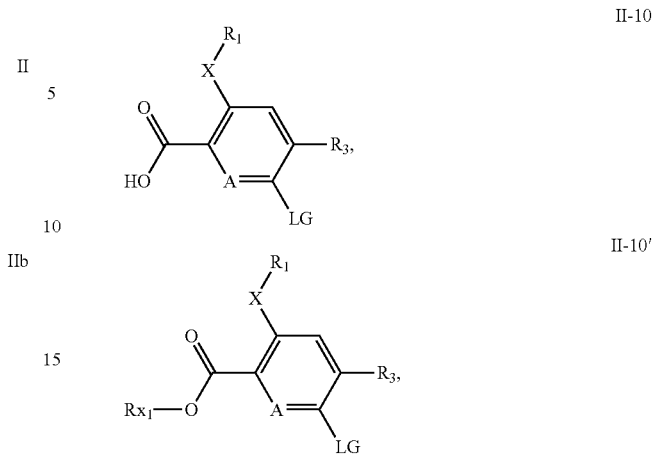

wherein X, $R_1$, $R_3$ and A are as described under formula I above, and in which $Rx_1$ is $C_1$-$C_6$alkyl, and wherein LG is a leaving group, for example a halogen or a sulfonate, preferably chlorine, bromine, iodine or trifluoromethanesulfonate. For example, 6-chloro-3-ethylsulfanyl-pyridine-2-carboxylic acid is known from WO 2017/001314, or methyl 5-chloro-2-ethylsulfanyl-benzoate from Synthesis 2011, (21), 3429-3434.

Compounds of the formula Z-1

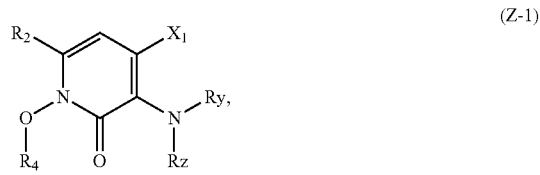

wherein $R_2$, and $R_4$ are as defined under formula I above; $X_1$ is halogen or azido; Ry is hydrogen or Boc (di-tert-butyldicarbonate) and Rz is $C_1$-$C_4$alkyl; are novel and especially prepared for the preparation of the compounds of formula I and therefore constitute a further object of this invention. The preferred embodiments of the substituents $R_2$ and $R_4$ as described under formula I above are also valid for the compounds of formula Z-1.

For preparing all further compounds of the formula (I) functionalized according to the definitions of formula II and Q, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Table 1 below can be prepared according to the methods described above. The examples which follow are intended to illustrate the invention and show preferred compounds of formula I. "Ph" represents the phenyl group.

Table 1: This table discloses the 48 compounds of the formula I-2c:

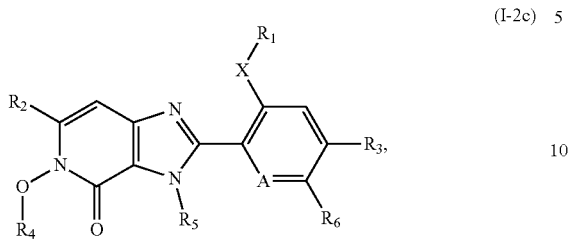

TABLE 1

| Comp. No. | X | $R_1$ | $R_3$ | $R_6$ | A | $R_2$ | $R_4$ | $R_5$ |
|---|---|---|---|---|---|---|---|---|
| 1.001 | S | —$CH_2CH_3$ | H | H | N | $CF_3$ | $CH_3$ | $CH_3$ |
| 1.002 | $SO_2$ | —$CH_2CH_3$ | H | H | N | $CF_3$ | $CH_3$ | $CH_3$ |
| 1.003 | S | —$CH_2CH_3$ | H | ![triazole] | N | $CF_3$ | $CH_3$ | $CH_3$ |
| 1.004 | $SO_2$ | —$CH_2CH_3$ | H | ![triazole] | N | $CF_3$ | $CH_3$ | $CH_3$ |
| 1.005 | S | —$CH_2CH_3$ | ![triazole] | H | N | $CF_3$ | $CH_3$ | $CH_3$ |
| 1.006 | $SO_2$ | —$CH_2CH_3$ | ![triazole] | H | N | $CF_3$ | $CH_3$ | $CH_3$ |
| 1.007 | S | —$CH_2CH_3$ | H | ![Cl-triazole] | N | $CF_3$ | $CH_3$ | $CH_3$ |
| 1.008 | $SO_2$ | —$CH_2CH_3$ | H | ![Cl-triazole] | N | $CF_3$ | $CH_3$ | $CH_3$ |
| 1.009 | S | —$CH_2CH_3$ | ![Cl-triazole] | H | N | $CF_3$ | $CH_3$ | $CH_3$ |

TABLE 1-continued

| Comp. No. | X | R₁ | R₃ | R₆ | A | R₂ | R₄ | R₅ |
|---|---|---|---|---|---|---|---|---|
| 1.010 | SO₂ | —CH₂CH₃ | 3-chloro-1,2,4-triazol-1-yl | H | N | CF₃ | CH₃ | CH₃ |
| 1.011 | S | —CH₂CH₃ | H | pyrazol-1-yl | N | CF₃ | CH₃ | CH₃ |
| 1.012 | SO₂ | —CH₂CH₃ | H | pyrazol-1-yl | N | CF₃ | CH₃ | CH₃ |
| 1.013 | S | —CH₂CH₃ | pyrazol-1-yl | H | N | CF₃ | CH₃ | CH₃ |
| 1.014 | SO₂ | —CH₂CH₃ | pyrazol-1-yl | H | N | CF₃ | CH₃ | CH₃ |
| 1.015 | S | —CH₂CH₃ | H | 1-cyanocyclopropyl | N | CF₃ | CH₃ | CH₃ |
| 1.016 | SO₂ | —CH₂CH₃ | H | 1-cyanocyclopropyl | N | CF₃ | CH₃ | CH₃ |
| 1.017 | S | —CH₂CH₃ | 1-cyanocyclopropyl | H | N | CF₃ | CH₃ | CH₃ |
| 1.018 | SO₂ | —CH₂CH₃ | 1-cyanocyclopropyl | H | N | CF₃ | CH₃ | CH₃ |
| 1.019 | S | —CH₂CH₃ | H | NH₂ | N | CF₃ | CH₃ | CH₃ |
| 1.020 | SO₂ | —CH₂CH₃ | H | NH₂ | N | CF₃ | CH₃ | CH₃ |
| 1.021 | S | —CH₂CH₃ | NH₂ | H | N | CF₃ | CH₃ | CH₃ |
| 1.022 | SO₂ | —CH₂CH₃ | NH₂ | H | N | CF₃ | CH₃ | CH₃ |
| 1.023 | S | —CH₂CH₃ | Cl | NH₂ | N | CF₃ | CH₃ | CH₃ |
| 1.024 | SO₂ | —CH₂CH₃ | Cl | NH₂ | N | CF₃ | CH₃ | CH₃ |
| 1.025 | S | —CH₂CH₃ | NH₂ | Cl | N | CF₃ | CH₃ | CH₃ |
| 1.026 | SO₂ | —CH₂CH₃ | NH₂ | Cl | N | CF₃ | CH₃ | CH₃ |

TABLE 1-continued
| Comp. No. | X | R₁ | R₃ | R₆ | A | R₂ | R₄ | R₅ |
|---|---|---|---|---|---|---|---|---|
| 1.027 | S | —CH₂CH₃ | H | 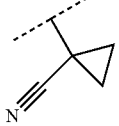 | C | CF₃ | CH₃ | CH₃ |
| 1.028 | SO₂ | —CH₂CH₃ | H | 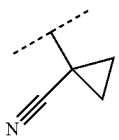 | C | CF₃ | CH₃ | CH₃ |
| 1.029 | S | —CH₂CH₃ | 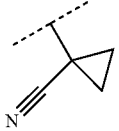 | H | C | CF₃ | CH₃ | CH₃ |
| 1.03 | SO₂ | —CH₂CH₃ | 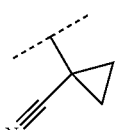 | H | C | CF₃ | CH₃ | CH₃ |
| 1.031 | S | —CH₂CH₃ | H | H | C | CF₃ | CH₃ | CH₃ |
| 1.032 | SO₂ | —CH₂CH₃ | H | H | C | CF₃ | CH₃ | CH₃ |
| 1.033 | SO | —CH₂CH₃ | H | H | N | CF₃ | CH₃ | CH₃ |
| 1.034 | SO | —CH₂CH₃ | H | 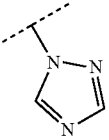 | N | CF₃ | CH₃ | CH₃ |
| 1.035 | SO | —CH₂CH₃ | 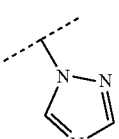 | H | N | CF₃ | CH₃ | CH₃ |
| 1.036 | SO | —CH₂CH₃ | H | 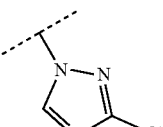 | N | CF₃ | CH₃ | CH₃ |
| 1.037 | SO | —CH₂CH₃ | 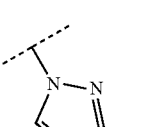 | H | N | CF₃ | CH₃ | CH₃ |
| 1.038 | SO | —CH₂CH₃ | H | 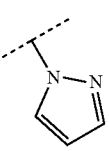 | N | CF₃ | CH₃ | CH₃ |
| 1.039 | SO | —CH₂CH₃ | 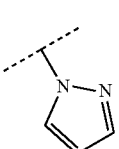 | H | N | CF₃ | CH₃ | CH₃ |

TABLE 1-continued

| Comp. No. | X | $R_1$ | $R_3$ | $R_6$ | A | $R_2$ | $R_4$ | $R_5$ |
|---|---|---|---|---|---|---|---|---|
| 1.040 | SO | —CH$_2$CH$_3$ | H | 1-cyanocyclopropyl | N | CF$_3$ | CH$_3$ | CH$_3$ |
| 1.041 | SO | —CH$_2$CH$_3$ | 1-cyanocyclopropyl | H | N | CF$_3$ | CH$_3$ | CH$_3$ |
| 1.042 | SO | —CH$_2$CH$_3$ | H | NH$_2$ | N | CF$_3$ | CH$_3$ | CH$_3$ |
| 1.043 | SO | —CH$_2$CH$_3$ | NH$_2$ | H | N | CF$_3$ | CH$_3$ | CH$_3$ |
| 1.044 | SO | —CH$_2$CH$_3$ | Cl | NH$_2$ | N | CF$_3$ | CH$_3$ | CH$_3$ |
| 1.045 | SO | —CH$_2$CH$_3$ | NH$_2$ | Cl | N | CF$_3$ | CH$_3$ | CH$_3$ |
| 1.046 | SO | —CH$_2$CH$_3$ | H | 1-cyanocyclopropyl | C | CF$_3$ | CH$_3$ | CH$_3$ |
| 1.047 | SO | —CH$_2$CH$_3$ | 1-cyanocyclopropyl | H | C | CF$_3$ | CH$_3$ | CH$_3$ |
| 1.048 | SO | —CH$_2$CH$_3$ | H | H | C | CF$_3$ | CH$_3$ | CH$_3$ | and the N-oxides of the compounds of Table 1.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:
from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;
from the order Anoplura, for example,

*Haematopinus* spp., *Linognathus* spp., *Pediculus* spp., *Pemphigus* spp. and *Phylloxera* spp.; from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.; from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;
from the order Hemiptera, for example,

*Acanthocoris scabrator*, *Acrosternum* spp, *Adelphocoris lineolatus*, *Amblypelta nitida*, *Bathycoeliai thalassina*, *Blis-* sus spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens; Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplo-campa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp., *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Gra-pholita* spp., *Hedya nubiferana, Heliothis* spp., *Hellula undalis, Herpetogramma* spp., *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypi-ela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Arion (*A. ater*, *A. circumscriptus*, *A. hortensis*, *A. rufus*); Bradybaenidae (*Bradybaena fruticum*); Cepaea (*C. hortensis*, *C. Nemoralis*); ochlodina; Deroceras (*D. agrestis*, *D. empiricorum*, *D. laeve*, *D. reticulatum*); Discus (*D. rotundatus*); Euomphalia; Galba (*G. trunculata*); Helicelia (*H. itala*, *H. obvia*); Helicidae Helicigona arbustorum); Helicodiscus; Helix (*H. aperta*); Limax (*L. cinereoniger*, *L. flavus*, *L. marginatus*, *L. maximus*, *L. tenellus*); Lymnaea; Milax (*M. gagates*, *M. marginatus*, *M. sowerbyi*); Opeas; Pomacea (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens*, *Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de I'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de I'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de I'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF—YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 03/034823, U.S. Pat. No. 5,631,072, WO 2005/64072, WO 2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
| --- | --- | --- |
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
| --- | --- | --- |
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, *Viburnum*, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, *Eucalyptus*, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, *Mimosa*, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |

TABLE B-continued

Examples of native woodborers of economic importance.

| Family | Species | Host or Crop Infested |
| --- | --- | --- |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as Cyclocephala spp. (e.g. masked chafer, C. lurida), Rhizotrogus spp. (e.g. European chafer, R. majalis), Cotinus spp. (e.g. Green June beetle, C. nitida), Popillia spp. (e.g. Japanese beetle, P. japonica), Phyllophaga spp. (e.g. May/June beetle), Ataenius spp. (e.g. Black turfgrass ataenius, A. spretulus), Maladera spp. (e.g. Asiatic garden beetle, M. castanea) and Tomarus spp.), ground pearls (Margarodes spp.), mole crickets (tawny, southern, and short-winged; Scapteriscus spp., Gryllotalpa africana) and leatherjackets (European crane fly, Tipula spp.).

The present invention may also be used to control insect pests of turfgrass that are thatch dwelling, including armyworms (such as fall armyworm Spodoptera frugiperda, and common armyworm Pseudaletia unipuncta), cutworms, billbugs (Sphenophorus spp., such as S. venatus verstitus and S. parvulus), and sod webworms (such as Crambus spp. and the tropical sod webworm, Herpetogramma phaeopteralis).

The present invention may also be used to control insect pests of turfgrass that live above the ground and feed on the turfgrass leaves, including chinch bugs (such as southern chinch bugs, Blissus insularis), Bermudagrass mite (Eriophyes cynodoniensis), rhodesgrass mealybug (Antonina graminis), two-lined spittlebug (Propsapia bicincta), leafhoppers, cutworms (Noctuidae family), and greenbugs.

The present invention may also be used to control other pests of turfgrass such as red imported fire ants (Solenopsis invicta) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:
Of the order Anoplurida: Haematopinus spp., Linognathus spp., Pediculus spp. and Phtirus spp., Solenopotes spp.
Of the order Mallophagida: Trimenopon spp., Menopon spp., Trinoton spp., Bovicola spp., Werneckiella spp., Lepikentron spp., Damalina spp., Trichodectes spp. and Felicola spp.

Of the order Diptera and the suborders Nematocerina and Brachycerina, for example Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

Of the order Siphonapterida, for example Pulex spp., Ctenocephalides spp., Xenopsylla spp., Ceratophyllus spp.

Of the order Heteropterida, for example Cimex spp., Triatoma spp., Rhodnius spp., Panstrongylus spp.

Of the order Blattarida, for example Blatta orientalis, Periplaneta americana, Blattelagermanica and Supella spp.

Of the subclass Acaria (Acarida) and the orders Meta- and Meso-stigmata, for example Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

Of the orders Actinedida (Prostigmata) and Acaridida (Astigmata), for example Acarapis spp., Cheyletiella spp., Ornithocheyletia spp., Myobia spp., Psorergatesspp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus spec., Tryptodendron spec., Apate monachus, Bostrychus capucins, Heterobostrychus brunneus, Sinoxylon spec. and Dinoderus minutus, and also hymenopterans such as Sirex juvencus, Urocerus gigas, Urocerus gigas taignus and Urocerus augur, and termites such as Kalotermes flavicollis, Cryptotermes brevis, Heterotermes

*indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether ethylene (7-8 mol of oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
| --- | --- |
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent.

The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

Preparatory Examples

"Mp" means melting point in ° C. Free radicals represent methyl groups. $^1$H and $^{19}$F NMR measurements were recorded on Brucker 400 MHz or 300 MHz spectrometers, chemical shifts are given in ppm relevant to a TMS standard. Spectra measured in deuterated solvents as indicated. Either one of the LCMS methods below was used to characterize the compounds. The characteristic LCMS values obtained for each compound were the retention time ("Rt", recorded in minutes) and the measured molecular ion $(M+H)^+$ and/or $(M-H)^-$.

LCMS Methods:

Method A—Standard: (SQD-ZDQ-ZCQ)

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Method B—Standard Long: (SQD-ZDQ-ZCQ)

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85.

Method C—Unpolar: (SQD-ZDQ-ZCQ)

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 40% B, 60% A; 1.2-1.5 min 100% B; Flow (ml/min) 0.85.

Method D

Spectra were recorded on a Mass Spectrometer from Agilent Technologies (6410 Triple Quadruple Mass Spectrometer) equipped with an electrospray source (Polarity: Positive and Negative Polarity Switch, Capillary: 4.00 kV, Fragmentor: 100.00 V, Gas Temperature: 350° C., Gas Flow: 11 L/min, Nebulizer Gas: 45 psi, Mass range: 110-1000 Da, DAD Wavelength range: 210-400 nm). Column: KINETEX EVO C18, length 50 mm, diameter 4.6 mm, particle size 2.6 μm. Column oven temperature 40° C. Solvent gradient: A=Water with 0.1% formic acid: Acetonitrile (95:5 v/v). B=Acetonitrile with 0.1% formic acid. Gradient=0 min 90% A, 10% B; 0.9-1.8 min 0% A, 100% B, 2.2-2.5 min 90% A, 10% B. Flow rate 1.8 mL/min.

Method E

Spectra were recorded on a Mass Spectrometer from Waters (Acquity SDS Mass Spectrometer) equipped with an electrospray source (Polarity: Positive and Negative Polarity Switch, Capillary: 3.00 kV, Cone Voltage: 41.00 V, Source temperature: 150° C., Desolvation Gas Flow: 1000 L/Hr, Desolvation temperature: 500° C., Gas Flow @Cone: 50 L/hr, Mass range: 110-800 Da, PDA wavelength range: 210-400 nm.Column: Acquity UPLC HSS T3 C18, length 30 mm, diameter 2.1 mm, particle size 1.8 μm. Column oven temperature 40° C. Solvent gradient: A=Water with 0.1% formic acid: Acetonitrile (95:5 v/v). B=Acetonitrile with 0.05% formic acid. Gradient=0 min 90% A, 10% B; 0.2 min 50% A, 50% B; 0.7-1.3 min 0% A, 100% B; 1.4-1.6 min 90% A, 10% B. Flow rate 0.8 mL/min.

a) Synthesis of Intermediates

Example I1: Preparation of 4-bromo-1-methoxy-3-(methylamino)-6-(trifluoromethyl)pyridin-2-one

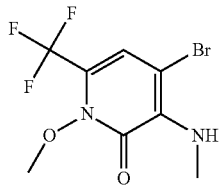

Step I1-A: Synthesis of N-[2-hydroxy-1-methoxy-6-oxo-2-(trifluoromethyl)-3H-pyridin-5-yl]benzamide

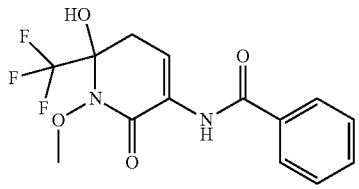 [SMILES: CON1C(=O)C(NC(=O)c2ccccc2)=CCC1(O)C(F)(F)F]

To a solution of N-[2-oxo-6-(trifluoromethyl)pyran-3-yl]benzamide (28 mmol, 8.0 g) in tetrahydrofuran (80 mL) was added O-methylhydroxylamine (42 mmol, 2.0 g) and acetic acid (56 mmol, 3.4 g, 3.2 mL). The reaction was refluxed for 4-5 hours. After the reaction was completed, the mixture was diluted with water (50 ml) and ethyl acetate (100 ml). The organic and aqueous phases were separated and the aqueous layer was extracted with ethyl acetate (3×50 ml). Combined organic layer was dried over sodium sulfate, filtered and concentrated under reduced pressure. The crude product was purified by combiflash (silica gel, 30% ethyl acetate-cyclohexane) to afford N-[2-hydroxy-1-methoxy-6-oxo-2-(trifluoromethyl)-3H-pyridin-5-yl]benzamide (18 mmol, 6.0 g). $^1$H NMR (400 MHz, CDCl$_3$) δ 8.68 (br s, 1H), 7.87-7.82 (m, 2H), 7.59-7.47 (m, 4H), 4.35 (s, 1H), 3.95 (s, 3H), 3.11 (m, 1H), 2.98 (m, 1H).

Step I1-B: Synthesis of tert-butyl-N-benzoyl-N-[1-methoxy-2-oxo-6-(trifluoromethyl)-3-pyridyl]carbamate

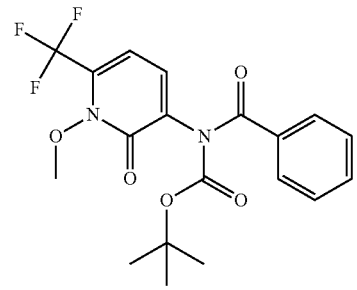 [SMILES: COn1c(C(F)(F)F)ccc(N(C(=O)OC(C)(C)C)C(=O)c2ccccc2)c1=O]

To a 0° C. cooled solution of N-[2-hydroxy-1-methoxy-6-oxo-2-(trifluoromethyl)-3H-pyridin-5-yl]benzamide (prepared in step I1-A, 9.1 mmol, 3.0 g) in dichloromethane (30 mL) was added N,N-diethylethanamine (18 mmol, 1.8 g, 2.5 mL) and N,N-dimethylpyridin-4-amine (1.8 mmol, 0.22 g). To this solution was added tert-butoxycarbonyl tert-butyl carbonate (23 mmol, 5.0 g). The reaction was stirred for 18 hours at ambient temperature. The mixture was diluted with water (20 ml) and extracted with dichloromethane (2×30 ml). Combined organic layer was dried over sodium sulfate, filtered and concentrated under reduced pressure. The crude product was purified by combiflash (silica gel, 30% ethyl acetate-cyclohexane) to afford tert-butyl N-benzoyl-N-[1-methoxy-2-oxo-6-(trifluoromethyl)-3-pyridyl]carbamate (6.5 mmol, 2.7 g). $^1$H NMR (400 MHz, CDCl$_3$) δ 7.87-7.75 (m, 2H), 7.58-7.50 (m, 1H), 7.50-7.40 (m, 3H), 6.64 (d, 1H), 4.16 (s, 3H), 1.22 (s, 9H).

Step I1-C: Synthesis of tert-butyl-N-[1-methoxy-2-oxo-6-(trifluoromethyl)-3-pyridyl]carbamate

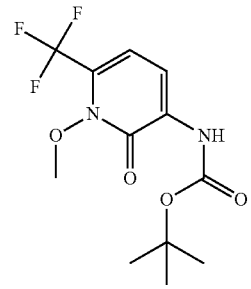 [SMILES: COn1c(C(F)(F)F)ccc(NC(=O)OC(C)(C)C)c1=O]

To a solution tert-butyl-N-benzoyl-N-[1-methoxy-2-oxo-6-(trifluoromethyl)-3-pyridyl]carbamate (1.212 mmol, 0.5 g) in tetrahydrofuran (5.0 mL) was added a solution lithium hydroxide hydrate (1.819 mmol, 0.07631 g) in water (1.0 mL). The reaction was stirred at ambient temperature for 4 hours. Then, the reaction was quenched with water (10 ml) and extracted with ethyl acetate (3×30 ml). Combined organic layer was dried over sodium sulfate, filtered and concentrated under reduced pressure. The crude product was purified by combiflash (silica gel, 30% ethyl acetate-cyclohexane) to afford tert-butyl N-[1-methoxy-2-oxo-6-(trifluoromethyl)-3-pyridyl]carbamate (1.071 mmol, 0.33 g). $^1$H NMR (400 MHz, CDCl$_3$) δ 7.96 (d, 1H), 7.76 (br s, 1H), 6.65 (d, 1H), 4.15 (s, 3H), 1.52 (s, 9H).

Step I1-D: Synthesis of tert-butyl N-[1-methoxy-2-oxo-6-(trifluoromethyl)-3-pyridyl]-N-methyl-carbamate

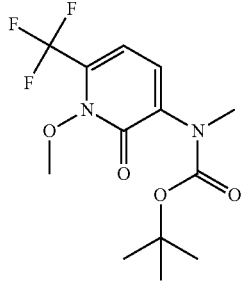

To a 0° C. cooled solution of tert-butyl-N-[1-methoxy-2-oxo-6-(trifluoromethyl)-3-pyridyl]carbamate (6.2 mmol, 1.9 g) in tetrahydrofuran (20 mL) was added sodium hydride (9.2 mmol, 0.37 g). The reaction was stirred at same temperature for 30 minutes. To this mixture was then added iodomethane (18 mmol, 2.6 g, 1.2 mL). The reaction was allowed to warm up to ambient temperature over 1-2 hours. Then, the reaction was diluted with water (15 ml), extracted with ethyl acetate (3×20 ml). Combined organic layer was dried over sodium sulfate, filtered and concentrated under reduced pressure. The crude product was purified by combiflash (silica gel, 30% ethyl acetate-cyclohexane) to afford tert-butyl-N—[1-methoxy-2-oxo-6-(trifluoromethyl)-3-pyridyl]-N-methyl-carbamate (5.6 mmol, 1.8 g). $^1$H NMR (400 MHz, CDCl$_3$) δ 7.30 (d, 1H), 6.55 (d, 1H), 4.16 (s, 3H), 3.18 (s, 3H), 1.46 (s, 9H).

Step I1-E: Synthesis of 1-methoxy-3-(methylamino)-6-(trifluoromethyl)pyridin-2-one

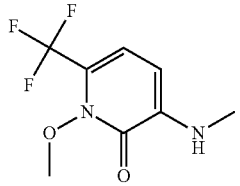

To a solution of tert-butyl-N-[1-methoxy-2-oxo-6-(trifluoromethyl)-3-pyridyl]-N-methyl-carbamate (5.3 mmol, 1.7 g) in dichloromethane (20 mL) was added 2,2,2-trifluoroacetic acid (26 mmol, 3.0 g, 2.0 mL). The reaction was stirred at ambient temperature for 18 hours. The reaction was diluted with water (15 ml), neutralised with sodium bicarbonate solution, extracted with dichloromethane (3×20 ml). Combined organic layer was dried over sodium sulfate, filtered and concentrated under reduced pressure. The crude product was purified by combiflash (silica gel, 30% ethyl acetate-cyclohexane) to afford 1-methoxy-3-(methylamino)-6-(trifluoromethyl)pyridin-2-one (5.0 mmol, 1.1 g). $^1$H NMR (400 MHz, CDCl$_3$) δ 6.61 (d, 1H), 6.02 (d, 1H), 4.13 (s, 3H), 2.89 (s, 3H).

Step I1-F: Synthesis of 4-bromo-1-methoxy-3-(methylamino)-6-(trifluoromethyl)pyridin-2-one

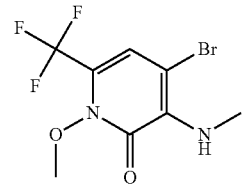 [SMILES: CNc1c(Br)cc(C(F)(F)F)n(OC)c1=O]

To a 0° C. cooled solution of 1-methoxy-3-(methylamino)-6-(trifluoromethyl)pyridin-2-one (5.0 mmol, 1.1 g) in N,N-dimethylformamide (12 mL) was added N-bromosuccinimide (7.4 mmol, 1.3 g). The reaction was stirred for 1 hour. Then, the reaction was diluted with water (50 ml), extracted with ethyl acetate (3×30 ml). Combined organic layer was dried over sodium sulfate, filtered and concentrated under reduced pressure. The crude product was purified by combiflash (silica gel, 20% ethyl acetate-cyclohexane) to afford 4-bromo-1-methoxy-3-(methylamino)-6-(trifluoromethyl)pyridin-2-one (0.6643 mmol, 0.2 g). $^1$H NMR (400 MHz, CDCl$_3$) δ 6.70 (s, 1H), 4.11 (s, 3H), 3.29 (s, 3H).

Example I2: Preparation of 4-(1-cyanocyclopropyl)-2-ethylsulfanyl-benzoic acid (B4)

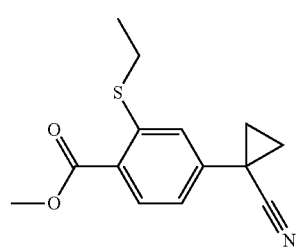

(B4)

Step I2-A: Synthesis of methyl 2-ethylsulfanyl-4-isoxazol-4-yl-benzoate

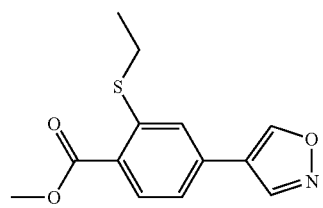 [SMILES: CCSc1cc(-c2cnoc2)ccc1C(=O)OC]

To a solution of methyl 4-bromo-2-ethylsulfanyl-benzoate (WO 2016/023954) (250 mg, 0.91 mmol) in dimethyl sulfoxide (8 mL) under argon were added water (4 mL), 4-isoxazoleboronic acid pinacol ester (213 mg, 1.09 mmol) and potassium fluoride (158 mg, 2.73 mmol). The thick reaction mixture was purged with argon for 5 minutes, then bis(triphenylphosphine)palladium(II) dichloride (6.4 mg, 0.009 mmol) was added. The vial was sealed and the mixture stirred in the microwave at 90° C. for 40 minutes. The reaction mixture was poured into iced-water, the resulting yellowish suspension filtered and washed with cold water. This solid was dissolved in dichlormethane, the solution dried over sodium sulfate and reduced to dryness under vacuum to afford methyl 2-ethylsulfanyl-4-isoxazol-4-yl-benzoate as a yellowish solid. This material was used in the next step without further purification. LCMS (method A): 262 (M−H)—, retention time 0.88 min.

Step I2-B: Synthesis of methyl 4-(cyanomethyl)-2-ethylsulfanyl-benzoate

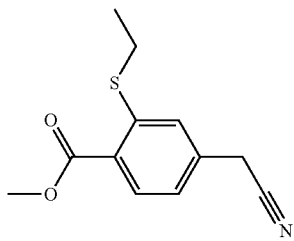 [SMILES: CCSc1cc(CC#N)ccc1C(=O)OC]

To a solution of methyl 2-ethylsulfanyl-4-isoxazol-4-yl-benzoate (760 mg, 2.89 mmol) in methanol (15 mL) was added a 1M potassium fluoride solution in water (8.66 mL, 8.66 mmol). The reaction mixture was stirred at reflux for 3 hours. After cooling, the suspension was filtered and the filtrate concentrated to dryness in vacuo. The residue was purified by Combiflash over silicagel to afford methyl 4-(cyano-methyl)-2-ethylsulfanyl-benzoate as a gum. LCMS (method A): 236 (M+H)$^+$, retention time 0.90 min. $^1$H NMR (400 MHz, CDCl$_3$) δ ppm 1.42 (t, 3H), 2.99 (q, 2H), 3.80 (s, 2H), 3.93 (s, 3H), 7.10 (dd, 1H), 7.28 (d, 1H), 7.99 (d, 1H).

Step I2-C: Synthesis of methyl 4-(1-cyanocyclopropyl)-2-ethylsulfanyl-benzoate (B3)

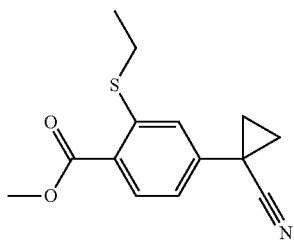

To a solution of methyl 4-(cyano-methyl)-2-ethylsulfa-nyl-benzoate (300 mg, 1.275 mmol) in acetonitrile (15 mL) were added cesium carbonate (1.24 g, 3.825 mmol) and 1,2-dibromoethane (719 mg, 3.825 mmol). The reaction mixture was stirred at reflux for 90 minutes. After cooling, the suspension was filtered and the filtrate concentrated to dryness in vacuo. The residue was purified by Combiflash over silicagel to afford methyl 4-(cyano-methyl)-2-ethylsul-fanyl-benzoate as an oil. LCMS (method A): 262 (M+H)$^+$, retention time 0.98 min. $^1$H NMR (400 MHz, CDCl$_3$) δ ppm 1.43 (t, 3H), 1.48 (m, 2H), 1.82 (m, 2H), 3.01 (q, 2H), 3.92 (s, 3H), 6.88 (dd, 1H), 7.35 (d, 1H), 7.94 (d, 1H).

Step I2-D: Synthesis of 4-(1-cyanocyclopropyl)-2-ethylsulfanyl-benzoate (B4)

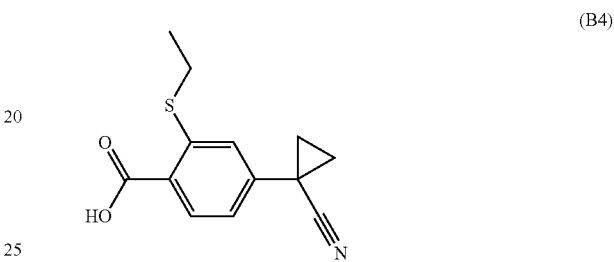

To a solution of methyl 4-(1-cyanocyclopropyl)-2-ethyl-sulfanyl-benzoate (198 mg, 0.758 mmol) in a mixture of tetrahydrofuran (9 mL) and water (3 mL) at 0-5° C. was added lithium hydroxide (1.5 eq., 1.137 mmol) and the reaction mixture was stirred at room temperature overnight. The solution was concentrated in vacuo, the residue diluted with t-butyl methyl ether (10 mL) and acidified with a 1M aqueous hydrochloric acid solution (10 mL). The organic layer was separated, the aqueous layer extracted with t-butyl methyl ether, the combined organic layers washed with water and brine, dried over sodium sulfate, filtered and concentrated under reduced pressure to afford 4-(1-cyano-cyclopropyl)-2-ethylsulfanyl-benzoate as a solid. This material was used in the next step without further purification. LCMS (method A): 246 (M−H)—, retention time 0.83 min. $^1$H NMR (400 MHz, CDCl$_3$) δ ppm 1.44 (t, 3H), 1.51 (m, 2H), 1.85 (m, 2H), 3.03 (q, 2H), 6.90 (dd, 1H), 7.41 (d, 1H), 8.10 (d, 1H).

Example I3: Preparation of 5-(1-cyano-1-methyl-ethyl)-3-ethylsulfanyl-pyridine-2-carboxylic acid (B6)

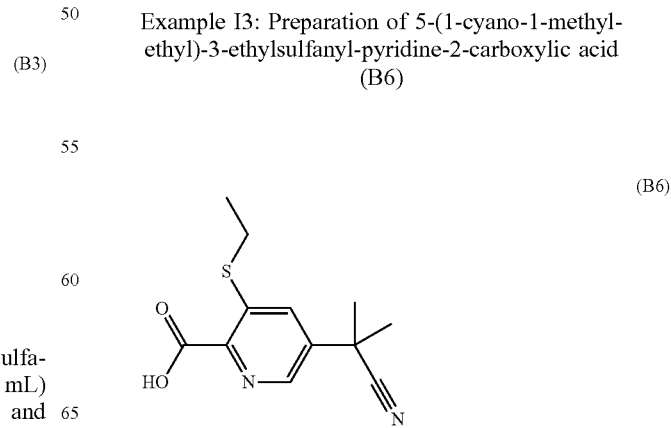

Step I3-A: Synthesis of methyl 5-(1-cyano-1-methyl-ethyl)-3-ethylsulfanyl-pyridine-2-carboxylate (B5)

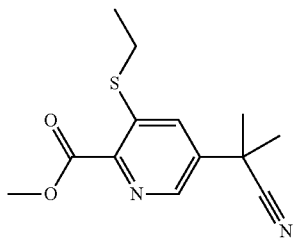

(B5)

To a solution of methyl 5-(cyanomethyl)-3-ethylsulfanyl-pyridine-2-carboxylate (4.0 g, 16.93 mmol) in acetonitrile (135 mL) were added cesium carbonate (16.55 g, 50.78 mmol) and methyl iodide (4.805 g, 33.86 mmol). The reaction mixture was stirred at 80° C. for 3 hours. After cooling, the mixture was diluted with water (15 mL) and the product extracted with ethyl acetate (3×10 mL). The combined organic layers were washed with brine, dried over sodium sulfate, filtered and concentrated under reduced pressure. The crude product was purified by combiflash (silica gel, 20% ethyl acetate-cyclohexane) to afford methyl 5-(1-cyano-1-methyl-ethyl)-3-ethylsulfanyl-pyridine-2-carboxylate (B5) (2.3 g, 8.70 mmol). LCMS (method E): 265 (M+H)$^+$, retention time 0.91 min. $^1$H NMR (400 MHz, CDCl$_3$) δ ppm 1.44 (t, 3H), 1.81 (s, 6H), 3.02 (q, 2H), 4.03 (s, 3H), 7.87 (d, 1H), 8.52 (d, 1H).

Step I3-B: Synthesis of 5-(1-cyano-1-methyl-ethyl)-3-ethylsulfanyl-pyridine-2-carboxylic acid (B6)

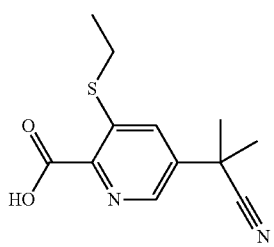

(B6)

To a solution of methyl 5-(1-cyano-1-methyl-ethyl)-3-ethylsulfanyl-pyridine-2-carboxylate (B5) (2.25 g, 8.51 mmol) in tetrahydrofuran (15 mL) were added lithiun hydroxide monohydrate (714 mg, 17.0 mmol) and water (5 mL) and the reaction mixture was stirred at room temperature for 5 hours. The solution was concentrated in vacuo, the residue diluted with water (20 mL) and acidified with a 2M aqueous hydrochloric acid solution (5 mL). The aqueous layer was extracted with ethyl acetate (7×20 mL), the combined organic layers washed with brine, dried over sodium sulfate, filtered and concentrated under reduced pressure to afford 5-(1-cyano-1-methyl-ethyl)-3-ethylsulfanyl-pyridine-2-carboxylic acid (B6) as a solid. This material was used in the next step without further purification. LCMS (method E): 251 (M+H)$^+$, retention time 0.78 min. $^1$H NMR (400 MHz, d6-DMSO) δ ppm 1.26 (t, 3H), 1.77 (s, 6H), 3.04 (q, 2H), 7.84 (d, 1H), 8.53 (d, 1H).

Example I4: Preparation of 4-(1-cyano-1-methyl-ethyl)-2-ethylsulfanyl-benzoic acid (B8)

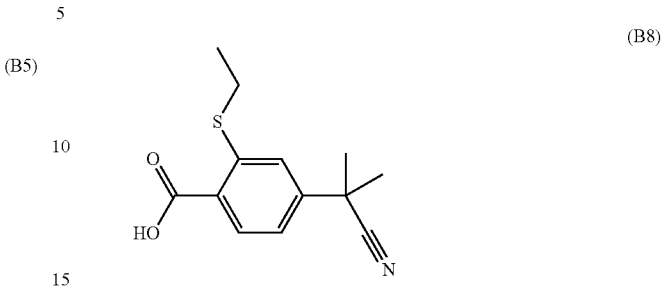

(B8)

Step I4-A: Synthesis of methyl 4-(1-cyano-1-methyl-ethyl)-2-ethylsulfanyl-benzoate (B7)

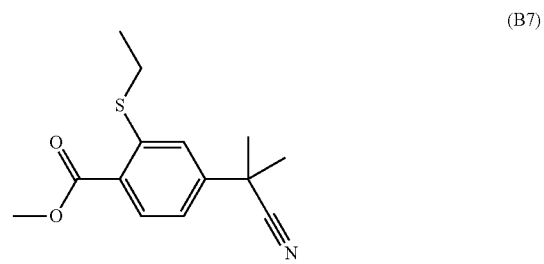 [SMILES: CCSc1cc(C(C)(C)C#N)ccc1C(=O)OC]

(B7)

To a solution of methyl 4-(cyanomethyl)-2-ethylsulfanyl-benzoate (120 mg, 0.510 mmol) in N,N-dimethylformamide (4 mL) at 0° C. was added sodium hydride (49 mg, 1.224 mmol, 60%) and the mixture was stirred for 30 minutes. Methyl iodide (76.2 µL, 173.7 mg, 1.224 mmol) was further added and stirring continued at room temperature for 2 hours. After cooling, the mixture was diluted with water (10 mL) and the product extracted with ethyl acetate (3×20 mL). The combined organic layers were washed with brine, dried over sodium sulfate, filtered and concentrated under reduced pressure. The crude product was co-evaporated with toluene (2-3 times) to afford methyl 4-(1-cyano-1-methyl-ethyl)-2-ethylsulfanyl-benzoate (B7). $^1$H NMR (400 MHz, CDCl$_3$) δ=1.43 (t, 3H), 1.75 (s, 6H), 3.02 (q, 2H), 3.93 (s, 3H), 7.20 (dd, 1H), 7.46 (d, 1H), 7.99 (m, 1H).

Step I4-B: Synthesis of 4-(1-cyano-1-methyl-ethyl)-2-ethylsulfanyl-benzoic acid (B8)

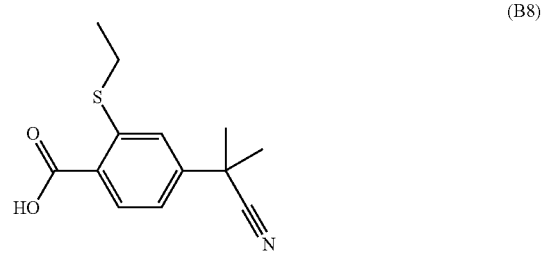 [SMILES: CCSc1cc(C(C)(C)C#N)ccc1C(=O)O]

(B8)

Obtained from methyl 4-(1-cyano-1-methyl-ethyl)-2-ethylsulfanyl-benzoate (B7) (760 mg, 2.77 mmol), lithium hydroxide monohydrate (4.15 mmol) in tetrahydrofuran (20 mL) and water (6 mL) according to procedure Example I3, step I3-B. The mixture was stirred at room temperature for two hours, then concentrated under reduced pressure. The crude material obtained after extractive workup was thoroughly dried in vacuo to afford 4-(1-cyano-1-methyl-ethyl)-2-ethylsulfanyl-benzoic acid (B8) as a solid. This material was used in the next step without further purification. LCMS (method E): 250 (M+H)$^+$, retention time 0.76 min.

b) Synthesis of Examples of Compounds of Formula (I)

Example P1: Preparation of 2-(3-ethylsulfonyl-2-pyridyl)-5-methoxy-3-methyl-6-(trifluoromethyl) imidazo[4,5-c]pyridin-4-one (compound A2)

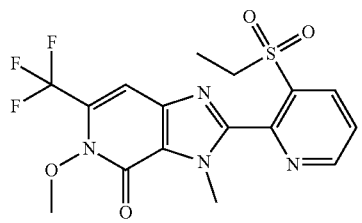

(A2)

Step P1-A: Synthesis of N-[4-bromo-1-methoxy-2-oxo-6-(trifluoromethyl)-3-pyridyl]-3-ethylsulfanyl-N-methyl-pyridine-2-carboxamide

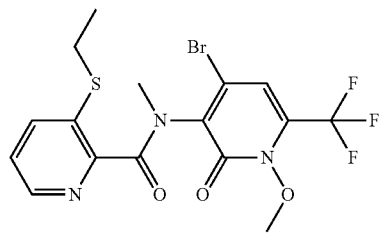 [SMILES: CCSc1cccnc1C(=O)N(C)c1c(Br)cc(C(F)(F)F)n(OC)c1=O]

To a 0° C. cooled solution of 3-ethylsulfanylpyridine-2-carboxylic acid (commercially available, CAS 14440-97-2, 2.183 mmol, 0.4 g) in dichloromethane (78 mmol, 6.6 g, 5.0 mL) and DMF (1 drop) was added oxalyl dichloride (3.93 mmol, 0.4988 g, 0.34 mL). The reaction was stirred for 2-3 hours and was concentrated under reduced pressure to remove all volatiles. Dichloromethane (5 mL) was added to this acid chloride. In an flask was taken 4-bromo-1-methoxy-3-(methylamino)-6-(trifluoromethyl) pyridin-2-one (1.587 mmol, 0.4777 g), N,N-diethylethanamine (5.95 mmol, 0.6021 g, 0.82 mL) in dichloromethane (5.0 mL) and cooled to 0° C. Then, to this mixture was added the solution of 3-ethylsulfanylpyridine-2-carbonyl chloride (1.983 mmol, 0.4 g) in dichloromethane (5 ml) prepared before. The reaction mass was stirred at ambient temperature for 2 hours. Then the reaction was diluted with water (15 ml), extracted with dichloromethane (3×20 ml). Combined organic layer was dried over sodium sulfate, filtered and concentrated under reduced pressure. The crude was purified by combiflash (silica gel, 30% ethyl acetate-cyclohexane) to afford N-[4-bromo-1-methoxy-2-oxo-6-(trifluoromethyl)-3-pyridyl]-3-ethylsulfanyl-N-methyl-pyridine-2-carboxamide (0.5361 mmol, 0.25 g). $^1$H NMR (400 MHz, CDCl$_3$) δ 7.93 (m, 1H), 7.62 (d, 1H), 7.16 (m, 1H), 6.58 (s, 1H), 4.09 (s, 3H), 3.37 (s, 3H), 2.94 (m, 2H), 1.37 (t, 3H).

Step P1-B: Synthesis of N-[4-azido-1-methoxy-2-oxo-6-(trifluoromethyl)-3-pyridyl]-3-ethylsulfanyl-N-methyl-pyridine-2-carboxamide

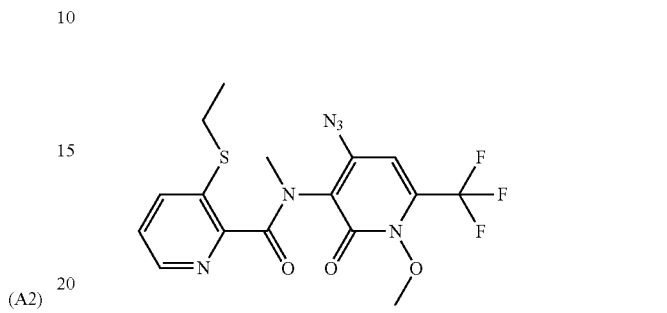

To a solution of N-[4-bromo-1-methoxy-2-oxo-6-(trifluoromethyl)-3-pyridyl]-3-ethylsulfanyl-N-methyl-pyridine-2-carboxamide (0.5361 mmol, 0.25 g) in N,N-dimethylformamide (3.0 mL) was added sodium azide (1.608 mmol, 0.1046 g). The reaction was heated at 90° C. for 3 hours. Then, the mixture was diluted with water (15 ml), extracted with ethyl acetate (3×30 ml). Combined organic layer was dried over sodium sulfate, filtered and concentrated under reduced pressure. The crude product was purified by combiflash (silica gel, 30% ethyl acetate-cyclohexane) to afford N-[4-azido-1-methoxy-2-oxo-6-(trifluoromethyl)-3-pyridyl]-3-ethylsulfanyl-N-methyl-pyridine-2-carboxamide (0.2556 mmol, 0.11 g). $^1$H NMR (400 MHz, CDCl$_3$) δ 8.03 (m, 1H), 7.63 (d, 1H), 7.16 (m, 1H), 6.14 (s, 1H), 3.98 (s, 3H), 3.35 (s, 3H), 2.96 (m, 2H), 1.37 (t, 3H).

Step P1-C: Synthesis of 2-(3-ethylsulfanyl-2-pyridyl)-5-methoxy-3-methyl-6-(trifluoromethyl) imidazo[4,5-c]pyridin-4-one (compound A1)

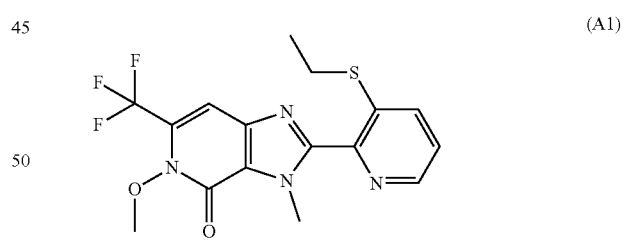

(A1)

To a microwave vial charged with N-[4-azido-1-methoxy-2-oxo-6-(trifluoromethyl)-3-pyridyl]-3-ethylsulfanyl-N-methyl-pyridine-2-carboxamide (0.233 mmol, 0.1 g) in dry toluene (2.0 mL) was added triphenylphosphane (0.233 mmol, 0.0612 g). The reaction mixture was stirred at ambient temperature for 2 hours, then subjected to microwave heating at 150° C. for 2 hours. The reaction was diluted with water (10 ml), extracted with ethyl acetate (3×20 ml). Combined organic layer was dried over sodium sulfate, filtered and concentrated under reduced pressure. The crude product was purified by combiflash (silica gel, 30% ethyl acetate-cyclohexane) to afford 2-(3-ethylsulfanyl-2-pyridyl)-5-methoxy-3-methyl-6-(trifluoromethyl) imidazo

[4,5-c]pyridin-4-one (0.1041 mmol, 0.04 g). $^1$H NMR (400 MHz, CDCl$_3$) δ 8.52 (br d, 1H), 7.78 (d, 1H), 7.40 (dd, 1H), 7.20 (s, 1H), 4.20 (m, 6H), 2.95 (q, 2H), 1.34 (t, 3H).

Step P1-D: Synthesis of 2-(3-ethylsulfonyl-2-pyridyl)-5-methoxy-3-methyl-6-(trifluoromethyl)imidazo[4,5-c]pyridin-4-one (compound A2)

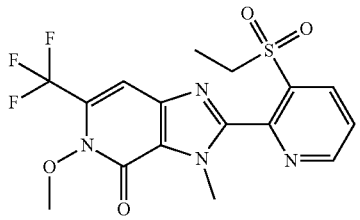

(A2)

To a solution of 2-(3-ethylsulfanyl-2-pyridyl)-5-methoxy-3-methyl-6-(trifluoromethyl)imidazo[4,5-c]pyridin-4-one (0.0780 mmol, 0.03 g) in dichloromethane (2.0 mL) was added meta-chloroperoxybenzoic acid (0.172 mmol, 0.0423 g). The reaction was stirred at ambient temperature for 18 hours. The reaction mass was quenched with an aqueous sodium bicarbonate solution (20 ml), extracted with dichloromethane (3×20 ml). The combined organic layer was dried over sodium sulfate, filtered and concentrated under reduced pressure. The crude product was purified by combiflash (silica gel, 30% ethyl acetate-cyclohexane) to afford 2-(3-ethylsulfonyl-2-pyridyl)-5-methoxy-3-methyl-6-(trifluoromethyl) imidazo[4,5-c]pyridin-4-one (0.0480 mmol, 0.02 g). $^1$H NMR (400 MHz, CDCl$_3$) δ 9.00 (d, 1H), 8.52 (d, 1H), 7.73 (m, 1H), 7.09 (s, 1H), 4.21 (s, 3H), 4.08 (s, 3H), 3.74 (q, 2H), 1.35 (t, 3H).

Example P2: Preparation of 2-[3-ethylsulfonyl-6-(1,2,4-triazol-1-yl)-2-pyridyl]-5-methoxy-3-methyl-6-(trifluoromethyl)imidazo[4,5-c]pyridin-4-one (compound A3)

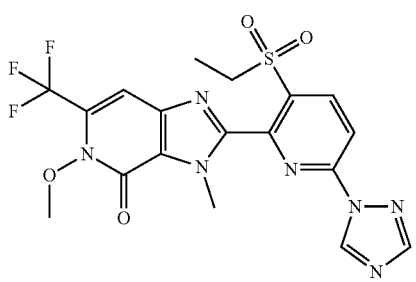

(A3)

Step P2-A: Synthesis of 2-(3-ethylsulfonyl-1-oxido-pyridin-1-ium-2-yl)-5-methoxy-3-methyl-6-(trifluoromethyl)imidazo[4,5-c]pyridin-4-one (compound A10)

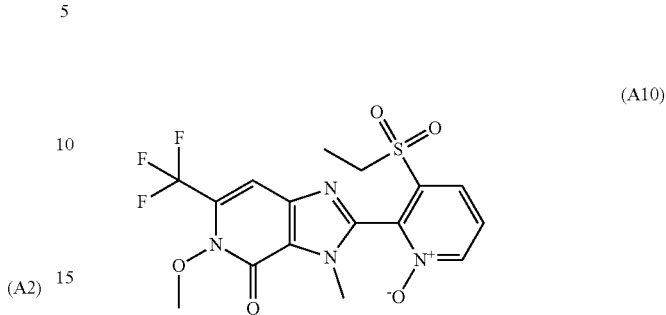

(A10)

To a solution of 2-(3-ethylsulfanyl-2-pyridyl)-5-methoxy-3-methyl-6-(trifluoromethyl) imidazo[4,5-c]pyridin-4-one (compound A1) (600 mg, 1.56 mmol) in dichloromethane (30 mL) was added meta-chloroperoxybenzoic acid (1.92 g, 7.80 mmol), and the mixture was heated at reflux overnight. The reaction mixture was quenched with an aqueous sodium bicarbonate solution (20 ml) and extracted with dichloromethane (3×20 ml). The combined organic layers were dried over sodium sulfate, filtered and concentrated under reduced pressure. The crude product was purified by combiflash (silica gel, 80% ethyl acetate-cyclohexane) to afford 2-(3-ethylsulfonyl-1-oxido-pyridin-1-ium-2-yl)-5-methoxy-3-methyl-6-(trifluoromethyl)imidazo[4,5-c]pyridin-4-one (compound A10) as a solid (0.925 mmol, 400 mg). LCMS (method D): 433 (M+H)$^+$, retention time 1.29 min. $^1$H NMR (400 MHz, CDCl$_3$) δ ppm 1.37 (t, 3H), 3.45 (m, 1H), 3.72 (m, 1H), 4.04 (s, 3H), 4.20 (s, 3H), 7.11 (s, 1H), 7.68 (t, 1H), 7.97 (d, 1H), 8.53 (d, 1H).

Step P2-B: Synthesis of 2-(6-chloro-3-ethylsulfonyl-2-pyridyl)-5-methoxy-3-methyl-6-(trifluoromethyl)imidazo[4,5-c]pyridin-4-one (compound A11)

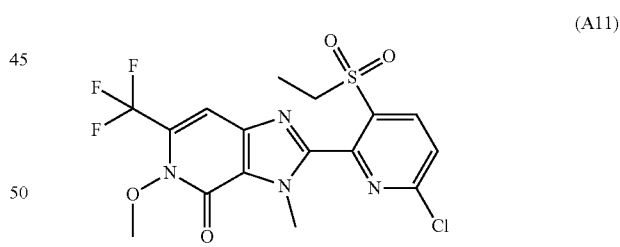

(A11)

A solution of 2-(3-ethylsulfonyl-1-oxido-pyridin-1-ium-2-yl)-5-methoxy-3-methyl-6-(trifluoromethyl) imidazo[4,5-c]pyridin-4-one (compound A10) (800 mg, 1.85 mmol) in phosphorus oxychloride (8 mL) was heated at 110° C. for 45 minutes. The reaction mixture was poured into crushed ice (10 g) and neutralised with solid sodium bicarbonate. The aqueous layer was extracted with dichloromethane (3×10 ml), the combined organic layers dried over sodium sulfate, filtered and concentrated under reduced pressure. The crude product was purified by combiflash (silica gel, 30% ethyl acetate-cyclohexane) to afford 2-(6-chloro-3-ethylsulfonyl-2-pyridyl)-5-methoxy-3-methyl-6-(trifluoromethyl)imidazo [4,5-c]pyridin-4-one (compound A11) as a solid (1.24 mmol, 0.56 g). LCMS (method D): 451/453 (M+H)$^+$, retention time 1.49 min. $^1$H NMR (400 MHz, CDCl$_3$) δ ppm 1.36 (t, 3H), 3.76 (q, 2H), 4.12 (s, 3H), 4.20 (s, 3H), 7.09 (s, 1H), 7.72 (d, 1H), 8.45 (d, 1H).

Step P2-C: Synthesis of 2-[3-ethylsulfonyl-6-(1,2,4-triazol-1-yl)-2-pyridyl]-5-methoxy-3-methyl-6-(trifluoromethyl)imidazo[4,5-c]pyridin-4-one (compound A3)

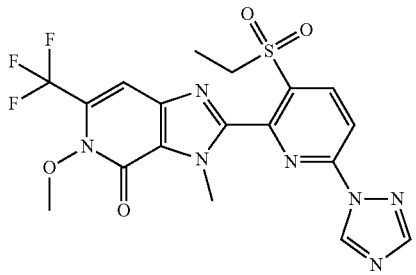

(A3)

To a solution of 2-(6-chloro-3-ethylsulfonyl-2-pyridyl)-5-methoxy-3-methyl-6-(trifluoromethyl) imidazo[4,5-c] pyridin-4-one (compound A11) (500 mg, 1.11 mmol) in N,N-dimethylformamide (20 mL) was added potassium carbonate (155.5 mg, 1.11 mmol), followed by 1H-1,2,4-triazole (76.6 mg, 1.11 mmol) and the mixture was stirred at room temperature for 3 hours. The reaction mixture was diluted with water (30 ml), extracted with ethyl acetate (3×50 ml), the combined organic layers dried over sodium sulfate, filtered and concentrated under reduced pressure. The crude product was purified by combiflash (silica gel, 40% ethyl acetate-cyclohexane) to afford 2-[3-ethylsulfonyl-6-(1,2,4-triazol-1-yl)-2-pyridyl]-5-methoxy-3-methyl-6-(trifluoromethyl)imidazo[4,5-c]pyridin-4-one (compound A3) as a solid (0.81 mmol, 390 mg), mp 227-229° C. LCMS (method D): 484 (M+H)$^+$, retention time 1.42 min. $^1$H NMR (400 MHz, CDCl$_3$) δ ppm 1.37 (t, 3H), 3.73 (q, 2H), 4.12 (s, 3H), 4.22 (s, 3H), 7.12 (s, 1H), 8.20 (s, 1H), 8.30 (d, 1H), 8.69 (d, 1H), 9.15 (s, 1H).

Example P3: Preparation of 2-(6-amino-5-chloro-3-ethylsulfonyl-2-pyridyl)-5-methoxy-3-methyl-6-(trifluoromethyl)imidazo[4,5-c]pyridin-4-one (compound A14)

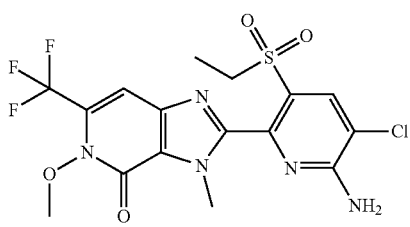

(A14)

Step P3-A: Synthesis of 2-(6-amino-3-ethylsulfonyl-2-pyridyl)-5-methoxy-3-methyl-6-(trifluoromethyl)imidazo[4,5-c]pyridin-4-one (compound A13)

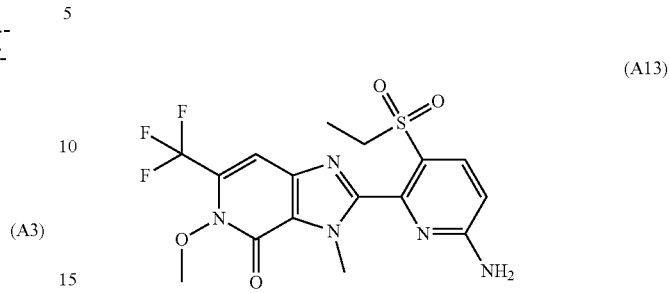

(A13)

A pressure vessel was charged with a solution of 2-(6-chloro-3-ethylsulfonyl-2-pyridyl)-5-methoxy-3-methyl-6-(trifluoromethyl)imidazo[4,5-c]pyridin-4-one (compound A11) (460 mg, 1.02 mmol) in tetrahydrofuran (7 mL). A 30% aqueous solution of ammonium hydroxide (8 mL, 62.3 mmol, 30%) was added, the vessel sealed and heated to 100° C. for 3 hours. The reaction mixture was concentrated in vacuo, the residue diluted with water and the product extracted with dichloromethane. The combined organic layers were washed with water and brine, dried over sodium sulfate, filtered and concentrated under reduced pressure. The crude product was purified by combiflash (silica gel, 40% ethyl acetate-cyclohexane) to afford 2-(6-amino-3-ethylsulfonyl-2-pyridyl)-5-methoxy-3-methyl-6-(trifluoromethyl) imidazo[4,5-c]pyridin-4-one (compound A13) as a solid (0.60 mmol, 257 mg), mp 210-212° C. LCMS (method E): 432 (M+H)$^+$, retention time 0.76 min. $^1$H NMR (400 MHz, CDCl$_3$) δ ppm 1.23 (t, 3H), 3.44 (q, 2H), 3.97 (s, 3H), 4.12 (s, 3H), 5.12 (br s, 2H), 6.64 (d, J=8.80 Hz, 1H), 7.00 (s, 1H), 8.04 (d, J=8.80 Hz, 1H).

Step P3-B: Synthesis of 2-(6-amino-5-chloro-3-ethylsulfonyl-2-pyridyl)-5-methoxy-3-methyl-6-(trifluoromethyl)imidazo[4,5-c]pyridin-4-one (compound A14)

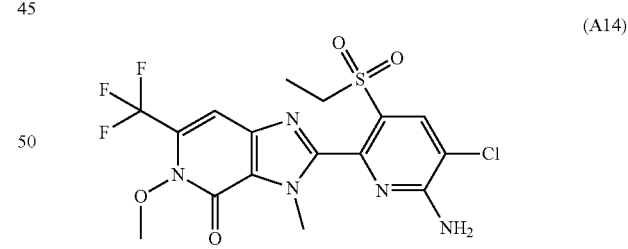

(A14)

To a solution of 2-(6-amino-3-ethylsulfonyl-2-pyridyl)-5-methoxy-3-methyl-6-(trifluoromethyl) imidazo[4,5-c]pyridin-4-one (compound A13) (100 mg, 0.232 mmol) in dry N,N-dimethylformamide (3 mL) was added N-chlorosuccinimide (0.9 eq., 0.209 mmol) and reaction mixture was stirred at 45° C. for 3 hours. The reaction mixture was diluted with water, extracted with ethyl acetate, the combined organic layers washed with water and brine, dried over sodium sulfate, filtered and concentrated under reduced pressure. The crude product was purified by combiflash (silica gel, 30% ethyl acetate-cyclohexane) to afford 2-(6-amino-5-chloro-3-ethylsulfonyl-2-pyridyl)-5-methoxy-3- methyl-6-(trifluoro-methyl)imidazo[4,5-c]pyridin-4-one (title compound A14) as a solid (0.118 mmol, 55 mg), mp 211-213° C. LCMS (method E): 466/468 (M+H)+, retention time 0.96 min. $^1$H NMR (400 MHz, CDCl$_3$) δ ppm 1.25 (t, 3H), 3.50 (q, 2H), 3.97 (s, 3H), 4.11 (s, 3H), 5.53 (br s, 2H), 7.00 (s, 1H), 8.14 (s, 1H).

Example P4: Preparation of 1-[5-ethylsulfonyl-6-[5-methoxy-3-methyl-4-oxo-6-(trifluoromethyl) imidazo[4,5-c]pyridin-2-yl]-3-pyridyl]cyclopropanecarbonitrile (compound A8)

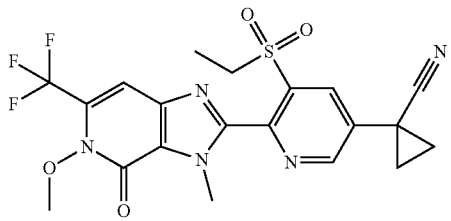

(A8)

Step P4-A: Preparation of methyl 5-(1-cyano-2-ethoxy-2-oxo-ethyl)-3-ethylsulfanyl-pyridine-2-carboxylate

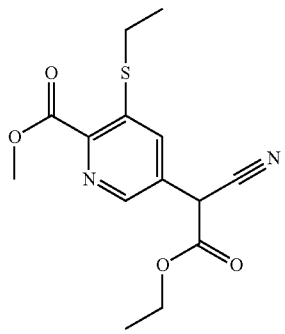 [SMILES: CCOC(=O)C(C#N)c1cnc(C(=O)OC)c(SCC)c1]

Methyl 5-bromo-3-ethylsulfanyl-pyridine-2-carboxylate (1 g, 3.62 mmol) was dissolved in dry dimethyl sulfoxide (10 mL). Dipotassium carbonate (1.25 g, 9.05 mmol) and benzyl(triethyl)ammonium chloride (8 mg, 0.036 mmol) were added to the stirred solution, followed by the slow addition of ethyl 2-cyanoacetate (0.614 g, 5.43 mmol). The resulting mixture was heated to 90° C. for 3 hours. The reaction mixture was cooled to room temperature, diluted with ethyl acetate (20 mL) and slowly treated with an aqueous 2 M hydrochloric acid solution (5 mL) and water (20 mL). The aqueous layer was extracted with ethyl acetate (2×20 mL). The combined organic layers were dried (Na$_2$SO$_4$), filtered, and concentrated under reduced pressure. The crude compound was purified by chromatography over silica gel (80% ethyl acetate in cyclohexane). The resulting material was dried under a high vacuum for several hours to afford the desired methyl 5-(1-cyano-2-ethoxy-2-oxo-ethyl)-3-ethylsulfanyl-pyridine-2-carboxylate (705 mg). LCMS (method E): 309 (M+H)+, retention time 0.93 min. $^1$H NMR (400 MHz, CDCl$_3$) δ ppm 1.32 (t, 3H), 1.43 (t, 3H), 3.00 (q, 2H), 4.03 (s, 3H), 4.30 (q, 2H), 7.83 (d, 1H), 8.49 (d, 1H).

Step P4-B: Preparation of methyl 5-(cyanomethyl)-3-ethylsulfanyl-pyridine-2-carboxylate

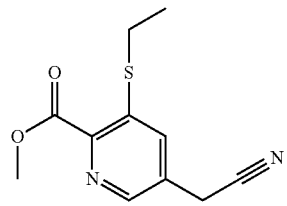 [SMILES: CCSc1cc(CC#N)cnc1C(=O)OC]

Methyl 5-(1-cyano-2-ethoxy-2-oxo-ethyl)-3-ethylsulfanyl-pyridine-2-carboxylate (0.700 g, 2.27 mmol) was dissolved in dimethyl sulfoxide (10 mL) and sodium chloride (1.32 g, 22.70 mmol) which was dissolved in a minimum amount of water (5 mL) was added to this solution. The resulting orange reaction mixture was heated to 120-130° C. After 5 hours, the mixture was cooled to 25° C., diluted with ethyl acetate (20 mL), and washed successively with water (20 mL) and brine (10 mL). The combined organic layer was dried (Na$_2$SO$_4$), filtered, and concentrated under reduced pressure. The crude was purified by chromatography over silica gel (50% ethyl acetate in cyclohexane) to afford methyl 5-(cyanomethyl)-3-ethylsulfanyl-pyridine-2-carboxylate (0.470 g). LCMS (method E): 237 (M+H)+, retention time 0.84 min. $^1$H NMR (400 MHz, CDCl$_3$) δ ppm 1.44 (t, 3H), 3.01 (q, 2H), 3.90 (s, 2H), 4.04 (s, 3H), 7.77 (d, 1H), 8.43 (d, 1H).

Step P4-C: Preparation of methyl 5-(1-cyanocyclopropyl)-3-ethylsulfanyl-pyridine-2-carboxylate (B1)

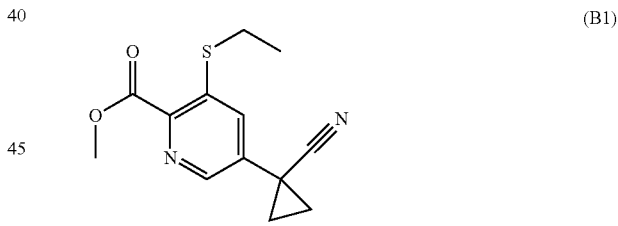

(B1)

To a solution of methyl 5-(cyanomethyl)-3-ethylsulfanyl-pyridine-2-carboxylate (0.470 g, 1.99 mmol) in acetonitrile (16 mL) were added cesium carbonate (1.94 g, 5.97 mmol) and 1,2-dibromoethane (0.346 mL, 3.98 mmol). The brown solution was stirred at 80° C. for 3 hours. The reaction mixture was cooled to room temperature and poured into water (15 mL). The aqueous layer was extracted 3 times with ethyl acetate (each 10 mL). The combined organic layers were washed once with brine (20 mL) and dried over Na2SO4, filtered and concentrated under reduced pressure. The crude product was purified by chromatography over silica gel (60% ethyl acetate in cyclohexane) to afford methyl 5-(1-cyano-cyclopropyl)-3-ethylsulfanyl-pyridine-2-carboxylate (0.455 g, B1). LCMS (method E): 263 (M+H)+, retention time 0.87 min. $^1$H NMR (400 MHz, CDCl$_3$) δ ppm 1.46 (t, 3H), 1.63 (m, 2H), 1.96 (m, 2H), 3.03 (q, 2H), 4.04 (s, 3H), 7.87 (d, 1H), 8.20 (d, 1H).

Step P4-D: Preparation of 5-(1-cyanocyclopropyl)-3-ethylsulfanyl-pyridine-2-carboxylic acid (B2)

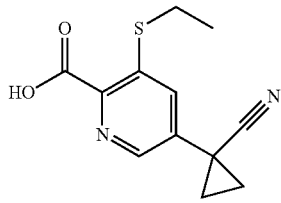

(B2)

To a solution of methyl 5-(1-cyanocyclopropyl)-3-ethylsulfanyl-pyridine-2-carboxylate (B1, 450 mg, 1.716 mmol) in methanol (6 mL) were added lithium hydroxide monohydrate (3.431 mmol) and water (1 mL). The reaction mixture was stirred at room temperature for 2 hours, then concentrated to dryness under reduced pressure. The residue was diluted with water (5 mL) and acidified with an aqueous 2N hydrochloric acid solution (5-10 mL). The aqueous layer was extracted with ethyl acetate (3×20 mL), the combined organic layers dried over sodium sulfate, filtered and concentrated under reduced pressure to afford pure 5-(1-cyanocyclopropyl)-3-ethylsulfanyl-pyridine-2-carboxylic acid (B2) (370 mg, 1.490 mmol) as a solid. This material was used in the next step without further purification. LCMS (method E): 249 (M+H)$^+$, retention time 0.69 min. $^1$H NMR (400 MHz, d6-DMSO) δ ppm 1.26 (t, 3H), 1.74 (m, 2H), 1.86 (m, 2H), 3.03 (q, 2H), 7.63 (d, 1H), 8.36 (d, 1H).

Step P4-E: Preparation of N-[4-bromo-6-(difluoromethyl)-1-methoxy-2-oxo-3-pyridyl]-2,2,2-trifluoro-N-methyl-acetamide

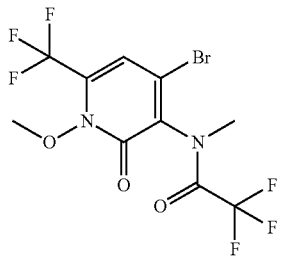 [SMILES: COn1c(C(F)(F)F)cc(Br)c(N(C)C(=O)C(F)(F)F)c1=O]

To a solution of 4-bromo-1-methoxy-3-(methylamino)-6-(trifluoromethyl)pyridin-2-one (Example I1, step I1-F) (5.0 g, 16.61 mmol) in dichloromethane (100 mL) was added trifluoroacetic anhydride (7.09 mL, 49.82 mmol) at room temperature. The reaction mixture was stirred for 30 minutes at room temperature and then evaporated to dryness under reduced pressure. Water (100 mL), then an aqueous saturated potassium carbonate solution (50 mL) were added and the aqueous layer was extracted with ethyl acetate (100 mL). The organic layer was washed with brine (100 mL), dried over sodium sulfate, filtered and concentrated. The crude product was purified over silica gel to afford pure N-[4-bromo-6-(difluoromethyl)-1-methoxy-2-oxo-3-pyridyl]-2,2,2-trifluoro-N-methyl-acetamide.

This material was used in the next step without further purification. LCMS (method E): 397/399 (M+H)$^+$, retention time 0.96 min. $^1$H NMR (400 MHz, CDCl$_3$) δ ppm 3.27 (s, 3H), 4.16 (s, 3H), 6.84 (s, 1H).

Step P4-F: Preparation of N-[4-azido-1-methoxy-2-oxo-6-(trifluoromethyl)-3-pyridyl]-2,2,2-trifluoro-N-methyl-acetamide

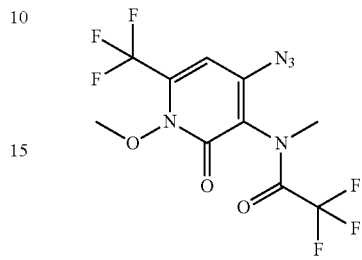

To a solution of N-[4-bromo-1-methoxy-2-oxo-6-(trifluoromethyl)-3-pyridyl]-2,2,2-trifluoro-N-methyl-acetamide (11.8 g, 29.7 mmol) in N,N-dimethylformamide (110 mL) was added sodium azide (2.9 g, 44.6 mmol) at room temperature. The reaction mixture was stirred at room temperature overnight. The above reaction was separately duplicated, then the combined mixtures were diluted with cold water (500 mL) and extracted with ethyl acetate (3×150 mL). The combined organic layers were washed with water (100 mL) and brine, dried over sodium sulfate, filtered and concentrated under reduced pressure below 40° C. to afford N-[4-azido-1-methoxy-2-oxo-6-(trifluoromethyl)-3-pyridyl]-2,2,2-trifluoro-N-methyl-acetamide. This material was used in the next step without further purification. LCMS (method E): 360 (M+H)+, retention time 0.90 min. $^1$H NMR (400 MHz, CDCl$_3$) δ ppm 3.23 (s, 3H), 4.15 (s, 3H), 6.40 (s, 1H).

Step P4-G: Preparation of 4-azido-1-methoxy-3-(methylamino)-6-(trifluoromethyl)pyridin-2-one

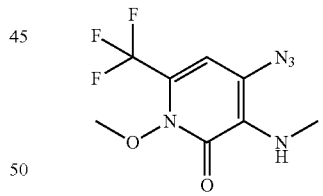

To a solution of N-[4-azido-1-methoxy-2-oxo-6-(trifluoromethyl)-3-pyridyl]-2,2,2-trifluoro-N-methyl-acetamide (4.6 g, 13.0 mmol) in methanol (100 mL) was added potassium carbonate (4.7 g, 33.0 mmol). The reaction mixture was stirred at room temperature overnight, then diluted with water (150 mL). The aqueous layer was extracted with ethyl acetate (2×75 mL), the combined organic layers washed with brine (150 mL), dried over sodium sulfate, filtered and concentrated under reduced pressure. The crude product was purified on silica gel (40% ethyl acetate in cyclohexane) to afford 4-azido-1-methoxy-3-(methylamino)-6-(trifluoromethyl)pyridin-2-one (2.2 g, 8.4 mmol). LCMS (method E): 264 (M+H)$^+$, retention time 0.94 min. $^1$H NMR (400 MHz, CDCl$_3$) δ ppm 3.18 (s, 3H), 4.11 (s, 3H), 6.46 (s, 1H).

Step P4-H: Preparation of 4-amino-1-methoxy-3-(methylamino)-6-(trifluoromethyl)pyridin-2-one

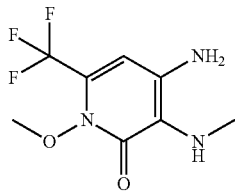 [SMILES: CNc1c(N)cc(C(F)(F)F)n(OC)c1=O]

To a solution of 4-azido-1-methoxy-3-(methylamino)-6-(trifluoromethyl)pyridin-2-one (1.7 g, 6.5 mmol) in tetrahydrofuran (50 mL) and water (5 mL) at room temperature was added triphenylphosphine (5.1 g, 19 mmol) and the resulting mixture stirred at room temperature for 2 hours. A 2M aqueous hydrochloric acid solution (9 mL, 18 mmol, 2 mol/L) was added and stirring continued overnight at room temperature. The reaction mixture was concentrated and quenched using an aqueous saturated potassium carbonate solution (20 mL). The aqueous layer was extracted with ethyl acetate (2×75 mL), the combined organic layers washed with brine (100 mL), dried over sodium sulfate, filtered and concentrated under reduced pressure. The residue was purified on silica gel (50-60% ethyl acetate in cyclohexane) to afford 4-amino-1-methoxy-3-(methylamino)-6-(trifluoromethyl)pyridin-2-one. LCMS (method E): 238 (M+H)$^+$, retention time 0.18 min. $^1$H NMR (400 MHz, d6-DMSO) δ ppm 2.60 (s, 3H), 3.98 (s, 3H), 5.75 (s, 2H), 6.42 (s, 1H).

Step P4-I: Preparation of 5-(1-cyanocyclopropyl)-3-ethylsulfanyl-N-[1-methoxy-3-(methylamino)-2-oxo-6-(trifluoromethyl)-4-pyridyl]pyridine-2-carboxamide and N-[4-amino-1-methoxy-2-oxo-6-(trifluoromethyl)-3-pyridyl]-5-(1-cyanocyclopropyl)-3-ethylsulfanyl-N-methyl-pyridine-2-carboxamide (Isomeric Mixture)

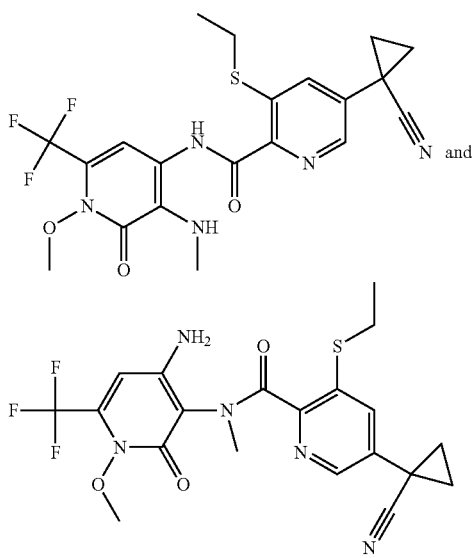

To a suspension of 5-(1-cyanocyclopropyl)-3-ethylsulfanyl-pyridine-2-carboxylic acid (B2) (400 mg, 1.61 mmol) in dichloromethane (16 mL) were added a catalytic amount of N,N-dimethylformamide (2 drops) and oxalyl chloride (3.22 mmol, 0.287 mL) dropwise. The reaction was stirred at room temperature for 6 hours and the solvent was removed in vacuo to afford 5-(1-cyanocyclopropyl)-3-ethylsulfanyl-pyridine-2-carbonyl chloride.

A solution of above 5-(1-cyanocyclopropyl)-3-ethylsulfanyl-pyridine-2-carbonyl chloride (428 mg, 1.60 mmol) in dry tetrahydrofuran (20 mL) was added slowly to a mixture of 4-amino-1-methoxy-3-(methylamino)-6-(trifluoromethyl)pyridin-2-one (456.6 mg, 1.92 mmol) and triethylamine (0.678 mL, 4.81 mmol) in tetrahydrofuran (9.6 mL). The reaction mixture was stirred at room temperature for 2 hours, then quenched with water and extracted with dichloromethane (100 ml). The combined organic layers were washed with water and brine, dried with anhydrous sodium sulfate and concentrated under reduced pressure to afford the desired isomeric mixture of 5-(1-cyanocyclopropyl)-3-ethylsulfanyl-N-[1-methoxy-3-(methylamino)-2-oxo-6-(trifluoromethyl)-4-pyridyl]pyridine-2-carboxamide and N-[4-amino-1-methoxy-2-oxo-6-(trifluoromethyl)-3-pyridyl]-5-(1-cyanocyclopropyl)-3-ethylsulfanyl-N-methyl-pyridine-2-carboxamide (750 mg, 1.60 mmol). This material was used in the next step without further purification. LCMS (method E): 468 (M+H)$^+$, retention time 0.86 min.

Step P4-J: Preparation of 1-[5-ethylsulfanyl-6-[5-methoxy-3-methyl-4-oxo-6-(trifluoromethyl) imidazo[4,5-c]pyridin-2-yl]-3-pyridyl]cyclopropanecarbonitrile (A 18)

(A18)

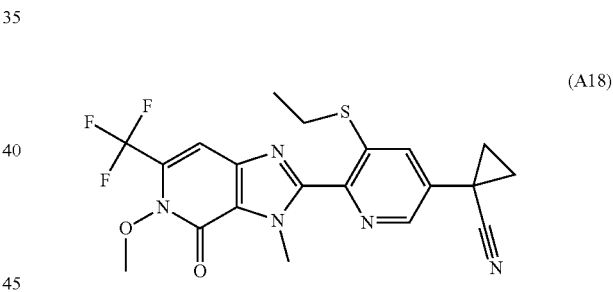

A solution of above isomeric mixture of 5-(1-cyanocyclopropyl)-3-ethylsulfanyl-N-[1-methoxy-3-(methylamino)-2-oxo-6-(trifluoromethyl)-4-pyridyl]pyridine-2-carboxamide and N-[4-amino-1-methoxy-2-oxo-6-(trifluoromethyl)-3-pyridyl]-5-(1-cyanocyclopropyl)-3-ethylsulfanyl-N-methyl-pyridine-2-carboxamide (750 mg, 1.60 mmol) in acetic acid (4.8 mL) was heated to 100° C. for 48 hours. After cooling to room temperature, the reaction mixture was evaporated. The residue was poured into water and extracted with ethyl acetate (3×100 mL), the combined organic layers washed with brine, dried over sodium sulfate and evaporated under reduced pressure. The crude product was purified by chromatography on silica gel (40% ethyl acetate in cyclohexane) to afford the desired product 1-[5-ethylsulfanyl-6-[5-methoxy-3-methyl-4-oxo-6-(trifluoromethyl)imidazo[4,5-c]pyridin-2-yl]-3-pyridyl]cyclopropanecarbonitrile (350 mg) as a solid. LCMS (method E): 450 (M+H)$^+$, retention time 1.03 min. $^1$H NMR (400 MHz, CDCl$_3$) δ ppm 1.37 (t, 3H), 1.59 (m, 2H), 1.93 (m, 2H), 3.01 (q, 2H), 4.20 (s, 3H), 4.21 (s, 3H), 7.25 (s, 1H), 7.76 (d, J=2.0 Hz, 1H), 8.32 (d, J=2.0 Hz, 1H).

Step P4-K: Synthesis of 1-[5-ethylsulfonyl-6-[5-methoxy-3-methyl-4-oxo-6-(trifluoromethyl)imidazo[4,5-c]pyridin-2-yl]-3-pyridyl]cyclopropanecarbonitrile (compound A8)

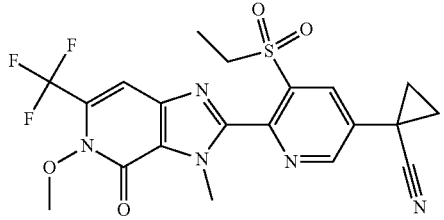
(A8)

To a solution of 1-[5-ethylsulfanyl-6-[5-m ethoxy-3-methyl-4-oxo-6-(trifluoromethyl)imidazo[4,5-c]pyridin-2-yl]-3-pyridyl]cyclopropanecarbonitrile (190 mg, 0.423 mmol) in dichloromethane (15 mL) at 0-5° C. was added meta-chloroperoxybenzoic acid (214 mg, 0.930 mmol, 75%) and the mixture was stirred for 2 hours. The reaction mixture was quenched with an aqueous sodium bicarbonate solution and extracted with dichloromethane (3×50 mL). The combined organic layers were washed with water and brine, dried over anhydrous sodium sulfate and concentrated under reduced pressure. The residue was purified by chromatography on silica gel (50% ethyl acetate in cyclohexane) to afford the desired product 1-[5-ethylsulfonyl-6-[5-methoxy-3-methyl-4-oxo-6-(trifluoromethyl)imidazo[4,5-c]pyridin-2-yl]-3-pyridyl]cyclopropanecarbonitrile (compound A8) as a solid (121 mg), mp 188-190° C. LCMS (method E): 482 (M+H)$^+$, retention time 0.97 min. $^1$H NMR (400 MHz, CDCl$_3$) δ ppm 1.37 (t, 3H), 1.67 (m, 2H), 2.05 (m, 2H), 3.80 (q, 2H), 4.08 (s, 3H), 4.21 (s, 3H), 7.09 (s, 1H), 8.23 (d, J=2.3 Hz, 1H), 9.03 (d, J=2.3 Hz, 1H).

Example P5: Preparation of 2-(5-bromo-3-ethylsulfonyl-2-pyridyl)-5-methoxy-3-methyl-6-(trifluoromethyl)imidazo[4,5-c]pyridin-4-one (compound A17)

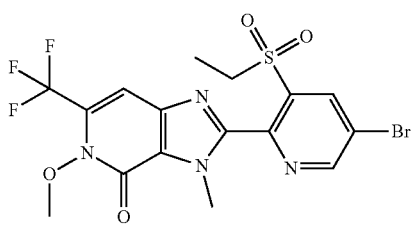
(A17)

Step P5-A: Preparation of 5-bromo-3-ethylsulfanyl-N-[1-methoxy-3-(methylamino)-2-oxo-6-(trifluoromethyl)-4-pyridyl]pyridine-2-carboxamide and N-[4-amino-1-methoxy-2-oxo-6-(trifluoromethyl)-3-pyridyl]-5-bromo-3-ethylsulfanyl-N-methyl-pyridine-2-carboxamide (isomeric mixture)

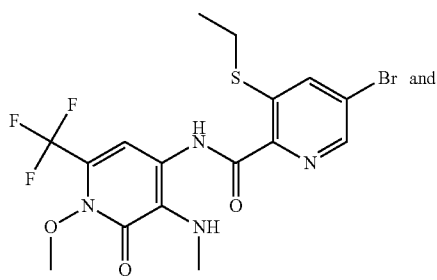

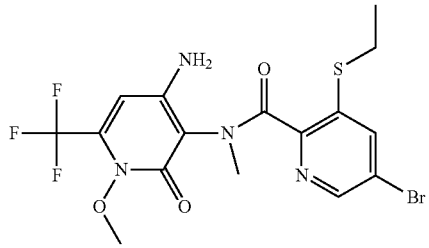

5-Bromo-3-ethylsulfanyl-pyridine-2-carbonyl chloride was obtained from 5-bromo-3-ethylsulfanyl-pyridine-2-carboxylic acid (WO 2016/005263) (300 mg, 1.145 mmol), a catalytic amount of N,N-dimethylformamide (0.01 mL) and oxalyl chloride (1.373 mmol, 0.121 mL) in dichloromethane (15 mL) according to procedure Example P4, Step P4-I. The reaction was stirred at room temperature for 1.5 hours and the solvent was removed in vacuo.

The isomeric mixture of 5-bromo-3-ethylsulfanyl-N-[1-methoxy-3-(methylamino)-2-oxo-6-(trifluoro-methyl)-4-pyridyl]pyridine-2-carboxamide and N-[4-amino-1-methoxy-2-oxo-6-(trifluoromethyl)-3-pyridyl]-5-bromo-3-ethylsulfanyl-N-methyl-pyridine-2-carboxamide was obtained from above 5-bromo-3-ethylsulfanyl-pyridine-2-carbonyl chloride (1.145 mmol), 4-amino-1-methoxy-3-(methylamino)-6-(trifluoromethyl)pyridin-2-one (407 mg, 1.717 mmol) and diisopropylethylamine (0.797 mL, 4.58 mmol) in tetrahydrofuran (20 mL) according to procedure Example P4, Step P4-I. The reaction mixture was stirred at room temperature for 3 hours, poured into an aqueous saturated potassium carbonate solution (10 mL) and water (100 mL), and extracted with ethyl acetate (50 mL). The organic layer was washed with brine (20 mL), dried over anhydrous sodium sulfate and concentrated under reduced pressure. The residue was purified by chromatography on silica gel (40% ethyl acetate in cyclohexane) to afford the isomeric products (392 mg). LCMS (method E): 481/483 (M+H)$^+$, retention time 0.93 min.

Step P5-B: Preparation of 2-(5-bromo-3-ethylsulfa-nyl-2-pyridyl)-5-methoxy-3-methyl-6-(trifluorom-ethyl)imidazo[4,5-c]pyridin-4-one (A19)

Step P5-C: Synthesis of 2-(5-bromo-3-ethylsulfo-nyl-2-pyridyl)-5-methoxy-3-methyl-6-(trifluorom-ethyl)imidazo[4,5-c]pyridin-4-one (compound A17)

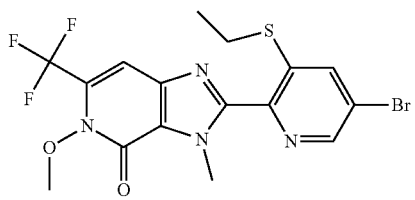
(A19)

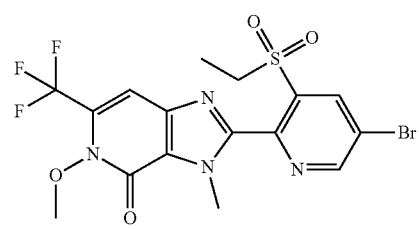
(A17)

Obtained from above isomeric mixture of 5-bromo-3-ethylsulfanyl-N-[1-methoxy-3-(methylamino)-2-oxo-6-(tri-fluoromethyl)-4-pyridyl]pyridine-2-carboxamide and N-[4-amino-1-methoxy-2-oxo-6-(trifluoromethyl)-3-pyridyl]-5-bromo-3-ethylsulfanyl-N-methyl-pyridine-2-carboxamide (300 mg, 0.623 mmol) in acetic acid (1.9 mL) according to procedure Example P4, Step P4-J. The reaction mixture was heated to 100° C. for 24 hours. The residue from the extractive workup was purified by chromatography on silica gel (40% ethyl acetate in cyclohexane) to afford 2-(5-bromo-3-ethylsulfanyl-2-pyridyl)-5-methoxy-3-methyl-6-(trifluo-romethyl)imidazo[4,5-c]pyridin-4-one as a solid (270 mg), mp 167-169° C. LCMS (method E): 463/465 (M+H)$^+$, retention time 1.11 min. $^1$H NMR (400 MHz, CDCl$_3$) δ ppm 1.37 (t, 3H), 2.98 (q, 2H), 4.20 (s, 3H), 4.22 (s, 3H), 7.25 (s, 1H), 7.87 (d, J=1.9 Hz, 1H), 8.55 (d, J=1.9 Hz, 1H).

Obtained from 2-(5-bromo-3-ethylsulfanyl-2-pyridyl)-5-methoxy-3-methyl-6-trifluoromethyl)imidazo[4,5-c]pyri-din-4-one (130 mg, 0.281 mmol) and meta-chloroperoxy-benzoic acid (142 mg, 0.617 mmol, 75%) in dichloromethane (15 mL) according to procedure Example P4, Step P4-K. The residue from the extractive workup was purified by chromatography on silica gel (30% ethyl acetate in cyclohexane) to afford 2-(5-bromo-3-ethylsulfonyl-2-pyridyl)-5-methoxy-3-methyl-6-(trifluoromethyl)imidazo [4,5-c]pyridin-4-one (compound A17) as a solid (88 mg), mp 173-175° C. LCMS (method E): 495/497 (M+H)$^+$, retention time 1.03 min. $^1$H NMR (400 MHz, CDCl$_3$) δ ppm 1.38 (t, 3H), 3.80 (q, 2H), 4.09 (s, 3H), 4.20 (s, 3H), 7.09 (s, 1H), 8.64 (d, J=2.2 Hz, 1H), 9.04 (d, J=2.2 Hz, 1H).

TABLE A

This table discloses compounds of the formula I-2d:

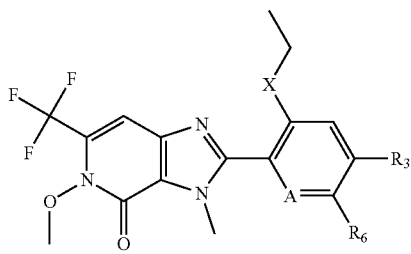
(I-2d)

| Comp. No. | X | R$_3$ | R$_6$ | A | Analytical data & IUPAC name |
|---|---|---|---|---|---|
| A1 (1.001) | S | H | H | N | See preparatory examples 2-(3-ethylsulfanyl-2-pyridyl)-5-methoxy-3-methyl-6-(trifluoromethyl)imidazo[4,5-c]pyridin-4-one |
| A2 (1.002) | SO$_2$ | H | H | N | See preparatory examples 2-(3-ethylsulfonyl-2-pyridyl)-5-methoxy-3-methyl-6-(trifluoromethyl)imidazo[4,5-c]pyridin-4-one |
| A18 | S | cyclopropyl-CN | H | N | LCMS (method E): 450 (M + H)$^+$, retention time 1.03 min. 1-[5-ethylsulfanyl-6-[5-methoxy-3-methyl-4-oxo-6-(trifluoromethyl)imidazo[4,5-c]pyridin-2-yl]-3-pyridyl]cyclopropanecarbonitrile |
| A19 | S | Br | H | N | LCMS (method E): 463/465 (M + H)$^+$, retention time 1.11 min. 2-(5-bromo-3-ethylsulfanyl-2-pyridyl)-5-methoxy-3-methyl-6-(trifluoromethyl) imidazo[4,5-c]pyridin-4-one |

TABLE A-continued

| | | | | | |
|---|---|---|---|---|---|
| A20 | S | H | Cl | N | LCMS (method E): 419/421 (M + H)+, retention time 1.11 min. 2-(6-chloro-3-ethylsulfanyl-2-pyridyl)-5-methoxy-3-methyl-6-(trifluoromethyl)imidazo[4,5-c]pyridin-4-one |
| A21 | S | CF₃ | H | N | LCMS (method D): 453 (M + H)+, retention time 1.56 min. 2-[3-ethylsulfanyl-5-(trifluoromethyl)-2-pyridyl]-5-methoxy-3-methyl-6-(trifluoromethyl)imidazo[4,5-c]pyridin-4-one |
| A22 | S | H | H | CH | LCMS (method E): 384 (M + H)+, retention time 1.08 min. 2-(2-ethylsulfanylphenyl)-5-methoxy-3-methyl-6-(trifluoromethyl)imidazo[4,5-c]pyridin-4-one |
| A23 | S | (cyclopropyl-CN) | H | CH | LCMS (method A): 449 (M + H)+, retention time 1.03 min. 1-[3-ethylsulfanyl-4-[5-methoxy-3-methyl-4-oxo-6-(trifluoromethyl)imidazo[4,5-c]pyridin-2-yl]phenyl]cyclopropanecarbonitrile |
| A24 | S | (C(CH₃)₂CN) | H | N | LCMS (method E): 452 (M + H)+, retention time 1.05 min. 2-[5-ethylsulfanyl-6-[5-methoxy-3-methyl-4-oxo-6-(trifluoromethyl)imidazo[4,5-c]pyridin-2-yl]-3-pyridyl]-2-methyl-propanenitrile |
| A25 | S | (C(CH₃)₂CN) | H | CH | LCMS (method E): 451 (M + H)+, retention time 1.12 min. 2-[3-ethylsulfanyl-4-[5-methoxy-3-methyl-4-oxo-6-(trifluoromethyl)imidazo[4,5-c]pyridin-2-yl]phenyl]-2-methyl-propanenitrile |

Further examples of compounds of formula (I), respectively of formula (I-2d) wherein A, X, R₃ and R₆ are as structurally drawn

| No. | IUPAC name | Structures | LCMS R$_t$ (min) | [M + H]+ (measured) | Method | MP (° C.) |
|---|---|---|---|---|---|---|
| A3 | 2-[3-ethylsulfonyl-6-(1,2,4-triazol-1-yl)-2-pyridyl]-5-methoxy-3-methyl-6-(trifluoromethyl)imidazo[4,5-c]pyridin-4-one | 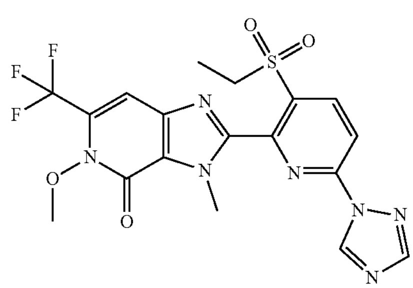 [SMILES: CCS(=O)(=O)c1ccc(-n2cncn2)nc1-c1nc2cc(C(F)(F)F)n(OC)c(=O)c2n1C] | 1.42 | 484 | D | 220-223 |
| A4 | 2-[3-ethylsulfonyl-6-(triazol-1-yl)-2-pyridyl]-5-methoxy-3-methyl-6-(trifluoromethyl)imidazo[4,5-c]pyridin-4-one | 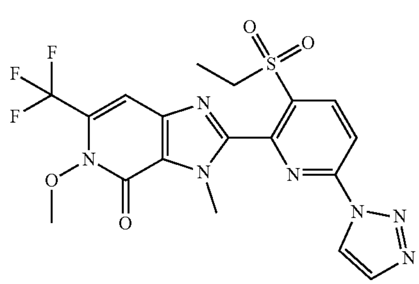 [SMILES: CCS(=O)(=O)c1ccc(-n2ccnn2)nc1-c1nc2cc(C(F)(F)F)n(OC)c(=O)c2n1C] | 0.97 | 484 | E | 166-168 |

TABLE A-continued

| | | | | | | |
|---|---|---|---|---|---|---|
| A5 | 2-[3-ethylsulfonyl-6-(triazol-2-yl)-2-pyridyl]-5-methoxy-3-methyl-6-(trifluoromethyl)imidazo[4,5-c]pyridin-4-one | | 0.96 | 484 | E | 180-182 |
| A6 | 2-[3-ethylsulfonyl-5-(trifluoromethyl)-2-pyridyl]-5-methoxy-3-methyl-6-(trifluoromethyl)imidazo[4,5-c]pyridin-4-one | | 1.05 | 485 | E | 158-160 |
| A7 | 2-(2-ethylsulfonylphenyl)-5-methoxy-3-methyl-6-(trifluoromethyl)imidazo[4,5-c]pyridin-4-one | | 1.36 | 416 | D | 166-168 |
| A8 | 1-[5-ethylsulfonyl-6-[5-methoxy-3-methyl-4-oxo-6-(trifluoromethyl)imidazo[4,5-c]pyridin-2-yl]-3-pyridyl]cyclopropanecarbonitrile | | 0.97 | 482 | E | 188-190 |
| A9 | 1-[3-ethylsulfonyl-4-[5-methoxy-3-methyl-4-oxo-6-(trifluoromethyl)imidazo[4,5-c]pyridin-2-yl]phenyl]cyclopropanecarbonitrile | | 0.94 | 481 | A | 212-214 |
| A10 | 2-(3-ethylsulfonyl-1-oxido-pyridin-1-ium-2-yl)-5-methoxy-3-methyl-6-(trifluoromethyl)imidazo[4,5-c]pyridin-4-one | | 1.29 | 433 | D | solid |
| A11 | 2-(6-chloro-3-ethylsulfonyl-2-pyridyl)-5-methoxy-3-methyl-6-(trifluoromethyl)imidazo[4,5-c]pyridin-4-one | | 1.49 | 451/453 | D | 195-197 |

TABLE A-continued

| A12 | 2-[5-ethylsulfonyl-6-[5-methoxy-3-methyl-4-oxo-6-(trifluoromethyl)imidazo[4,5-c]pyridin-2-yl]-3-pyridyl]-2-methyl-propanenitrile | | 1.00 | 484 | E | 191-193 |
|---|---|---|---|---|---|---|
| A13 | 2-(6-amino-3-ethylsulfonyl-2-pyridyl)-5-methoxy-3-methyl-6-(trifluoromethyl)imidazo[4,5-c]pyridin-4-one | | 0.76 | 432 | E | 210-212 |
| A14 | 2-(6-amino-5-chloro-3-ethylsulfonyl-2-pyridyl)-5-methoxy-3-methyl-6-(trifluoromethyl)imidazo[4,5-c]pyridin-4-one | | 0.96 | 466/468 | E | 211-213 |
| A15 | 2-[3-ethylsulfonyl-4-[5-methoxy-3-methyl-4-oxo-6-(trifluoromethyl)imidazo[4,5-c]pyridin-2-yl]phenyl]-2-methyl-propanenitrile | | 1.02 | 483 | E | 164-166 |
| A16 | 2-(6-amino-5-bromo-3-ethylsulfonyl-2-pyridyl)-5-methoxy-3-methyl-6-(trifluoromethyl)imidazo[4,5-c]pyridin-4-one | | 0.99 | 510/512 | E | 214-216 |
| A17 | 2-(5-bromo-3-ethylsulfonyl-2-pyridyl)-5-methoxy-3-methyl-6-(trifluoromethyl)imidazo[4,5-c]pyridin-4-one | | 1.03 | 495/497 | E | 173-175 |

TABLE B

Examples of intermediates of formula (II), (IIb), repectively (II-4), (II-6), (II-7) and (II-8)

| No. | IUPAC name | Structures | LCMS R$_t$ (min) | [M + H]$^+$ (measured) | Method | MP (° C.) |
|---|---|---|---|---|---|---|
| B1 | methyl 5-(1-cyanocyclopropyl)-3-ethylsulfanyl-pyridine-2-carboxylate | 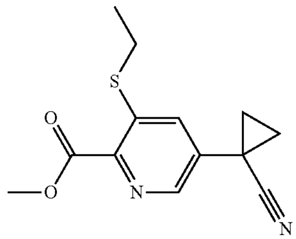 [SMILES: CCSc1cc(C2(C#N)CC2)cnc1C(=O)OC] | 0.87 | 263 | E | — |
| B2 | 5-(1-cyanocyclopropyl)-3-ethylsulfanyl-pyridine-2-carboxylic acid | 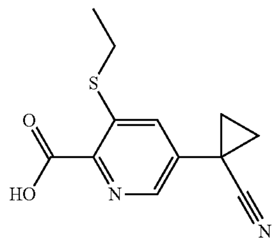 [SMILES: CCSc1cc(C2(C#N)CC2)cnc1C(=O)O] | 0.69 | 249 | E | solid |
| B3 | methyl 4-(1-cyanocyclopropyl)-2-ethylsulfanyl-benzoate | 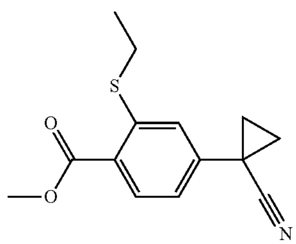 [SMILES: CCSc1cc(C2(C#N)CC2)ccc1C(=O)OC] | 0.98 | 262 | A | — |
| B4 | 4-(1-cyanocyclopropyl)-2-ethylsulfanyl-benzoic acid | 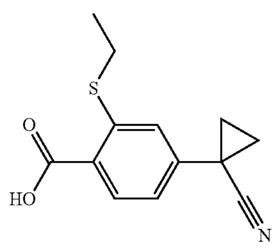 [SMILES: CCSc1cc(C2(C#N)CC2)ccc1C(=O)O] | 0.83 | 246 [M − H]$^-$ | A | solid |
| B5 | methyl 5-(1-cyano-1-methyl-ethyl)-3-ethylsulfanyl-pyridine-2-carboxylate | 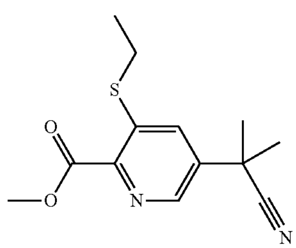 [SMILES: CCSc1cc(C(C)(C)C#N)cnc1C(=O)OC] | 0.91 | 265 | E | — |
| B6 | 5-(1-cyano-1-methyl-ethyl)-3-ethylsulfanyl-pyridine-2-carboxylic acid | 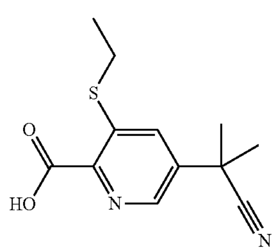 [SMILES: CCSc1cc(C(C)(C)C#N)cnc1C(=O)O] | 0.78 | 251 | E | solid |

TABLE B-continued

Examples of intermediates of formula (II), (IIb), repectively (II-4), (II-6), (II-7) and (II-8)

| No. | IUPAC name | Structures | R$_t$ (min) | LCMS [M + H]$^+$ (measured) | Method | MP (° C.) |
|---|---|---|---|---|---|---|
| B7 | methyl 4-(1-cyano-1-methyl-ethyl)-2-ethylsulfanyl-benzoate | 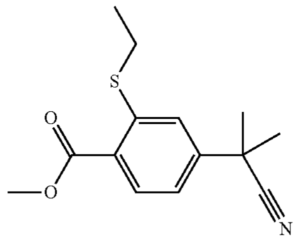 [SMILES: CCSc1cc(C(C)(C)C#N)ccc1C(=O)OC] | | $^1$H NMR (400 MHz, CDCl$_3$) δ = 1.43 (t, 3H)), 1.75 (s, 6H), 3.02 (q, 2H), 3.93 (s, 3H), 7.20 (dd, 1H), 7.46 (d, 1H), 7.99 (m, 1H). | | |
| B8 | 4-(1-cyano-1-methyl-ethyl)-2-ethylsulfanyl-benzoic acid | 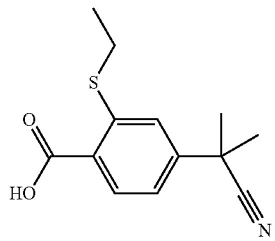 [SMILES: CCSc1cc(C(C)(C)C#N)ccc1C(=O)O] | 0.76 | 250 | E | solid |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Table 1 and A of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+ TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, dorametin [CCN]+TX, endosulfan (294)+TX, endothion (1121)+TX, EPN (297)+TX, eprinomectin [CCN]+TX, ethion (309)+ TX, ethoate-methyl (1134)+TX, etoxazole (320)+TX, etrimfos (1142)+TX, fenazaflor (1147)+TX, fenazaquin (328)+ TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacry-pyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+ TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/ Chemical Abstracts name) (1216)+TX, hexythiazox (441)+ TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+ TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+ TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+ TX, pp'-DDT (219)+TX, parathion (615)+TX, permethrin (626)+TX, petroleum oils (628)+TX, phenkapton (1330)+ TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+ TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+ TX, pyrethrin II (696)+TX, pyrethrins (696)+TX, pyridaben (699)+TX, pyridaphenthion (701)+TX, pyrimidifen (706)+ TX, pyrimitate (1370)+TX, quinalphos (711)+TX, quintiofos (1381)+TX, R-1492 (development code) (1382)+TX, RA-17 (development code) (1383)+TX, rotenone (722)+ TX, schradan (1389)+TX, sebufos+TX, selamectin [CCN]+ TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+ TX, tetranactin (653)+TX, tetrasul (1425)+TX, thiafenox+ TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, dorametin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+ TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+ TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+ TX, *Bacillus thuringiensis* Berliner (scientific name) (51)+ TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia*

*convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. acridum (scientific name) (523)+TX, *Metarhizium anisopliae* var. anisopliae (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11 E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlurel (421)+TX, grandlurell (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B$_1$ (839)+TX, trimedlure B2 (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl) phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, *Bacillus thuringiensis* delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin 1(696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O, O,O',O'-tetrapropyl dithiopyrophosphate (IUPAC name) (1424)+TX, oleic acid (IUPAC name) (593)+TX, ometoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene Ill [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium* verrucaria composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-l1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihyd roxy-4,6a, 12b-trimethyl-1-oxo-9-(3-pyridinyl)-2H, 11 Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX, lancotrione [1486617-21-3]+TX, florpyrauxifen [943832-81-3]]+TX, ipfentrifluconazole[1417782-08-1]+TX, mefentrifluconazole [1417782-03-6]+TX, quinofumelin [861647-84-9]+TX, chloroprallethrin [399572-87-3]+TX, cyhalodiamide [1262605-53-7]]+TX, fluazaindolizine [1254304-22-7]+TX, fluxametamide [928783-29-3]+TX, epsilon-metofluthrin [240494-71-7]+TX, epsilon-momfluorothrin [1065124-65-3]+TX, pydiflumetofen [1228284-64-7]+TX, kappa-bifenthrin [439680-76-9]+TX, broflanilide [1207727-04-5]+TX, dicloromezotiaz [1263629-39-5]+TX, dipymetitrone [16114-35-5]+TX, pyraziflumid [942515-63-1]+TX, kappa-tefluthrin [391634-71-2]+TX, fenpicoxamid [517875-34-2]+TX; fluindapyr [1383809-87-7]+TX; alpha-bromadiolone [28772-56-7]+TX; flupyrimin [1689566-03-7]+TX; benzpyrimoxan [1449021-97-9]+TX; acynonapyr [1332838-17-1]+TX; inpyrfluxam [1352994-65-2]+TX, isoflucypram [1255734-28-1]+TX; rescalure [64309-03-1]+TX; aminopyrifen [1531626-08-0]+TX; tyclopyrazoflor [1477919-27-9]+TX; and spiropidion [1229023-00-0]+TX; and microbials including: *Acinetobacter iwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®, BioNem-WP®, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®)+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, *bacteria* spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX,

*Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo*-miniatus+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C$_9$-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum* rifai (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®, Neemix®)+TX, canola oil (Lilly Miller Vegol®)+TX, *Chenopodium ambrosioides* near ambrosioides (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+

TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®)+TX; and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, Tetradecatrienyl acetate+TX, 13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, CheckMate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha Iongicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (ThriporS®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline Sf®+TX, Scia-Rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, Steinernematid spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used. "CAS Reg. No" means the Chemical Abstracts Registry Number.

The active ingredient mixture of the compounds of formula I selected from Table 1 and A with active ingredients described above comprises a compound selected from Table 1 and A and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Table 1 and A and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table 1 and A and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

Biological Examples

Example B1: Activity Against *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: A1, A2, A3, A4, A5, A6, A7, A8, A9, A12, A13, A14, A15, A16, A17, A19, A21, A22, A23, A24 and A25.

Example B2: Activity Against *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compound gave an effect of at least 80% in at least one of the two categories (mortality or growth inhibition) at an application rate of 200 ppm: A2, A3, A4, A5, A6, A7, A8, A9, A12, A13, A14, A15, A16, A17, A19, A21, A22, A23, A24 and A25.

Example B3: Activity Against *Myzus persicae* (Green Peach Aphid): Feeding/Contact Activity Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: A1, A2, A3, A4, A5, A6, A7, A8, A9, A12, A13, A14, A15, A16, A17, A19, A21 and A22.

Example B4: Activity Against *Myzus persicae* (Green Peach Aphid): Systemic Activity Roots of pea seedlings infested with an aphid population of mixed ages were placed directly into aqueous test solutions prepared from 10'000 DMSO stock solutions. The samples were assessed for mortality 6 days after placing seedlings into test solutions.

The following compound resulted in at least 80% mortality at a test rate of 24 ppm: A2, A3, A4, A5, A6, A7, A8, A9, A12, A13, A14, A15, A17 and A22.

Example B5: Activity Against *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: A1, A2, A3, A4, A5, A6, A7, A8, A9, A12, A13, A14, A15, A16, A17, A19, A21, A22, A23 and A24.

Example B6: Activity Against *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: A1, A2, A3, A4, A5, A6, A7, A8, A9, A12, A13, A14, A16, A17, A19, A21, A22, and A23.

Example B7: Activity Against *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compound gave an effect of at least 80% in at least one of the three categories (mortality, anti-feeding, or growth inhibition) at a test rate of 12.5 ppm: A2.

Example B8: Activity Against *Bemisia tabaci* (Cotton White Fly)

Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm: A3, A4, A8, A9, A12, A13, A14, A15 and A17.

Example B9: Activity Against *Tetranychus urticae* (Two-Spotted Spider Mite)

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm: A3 and A8, and A9.

Example B10: Comparison of the Insecticidal Activity of Compound A2 According to this Invention with the Structurally Closest Compound from the State of the Art The pesticidal activity of compound A2 according to the preparatory examples and of compound A17 from WO 2016/7023954 against *Spodoptera littoralis* (test Example B6 above), *Plutella xylostella* (Example B5), *Diabrotica balteata* (Example B1), *Myzus persicae* (feeding/contact, Example B3) and *Myzus persicae* (systemic, Example B4) is summarized in Table B10:

TABLE B10

| Compound | Concentration (ppm) | Insect | Mortality (%) |
| --- | --- | --- | --- |
| A2 (present invention) | 12.5 | *Spodoptera littoralis* | 80 |
| | 12.5 | *Plutella xylostella* | 80 |
| | 50 | *Diabrotica balteata* | 100 |
| | 50 | *Myzus persicae* (feeding/contact) | 100 |
| | 1.5 | *Myzus persicae* (systemic) | 80 |
| A17, known from WO 2016/023954 (state of the art) | 12.5 | *Spodoptera littoralis* | 0 |
| | 12.5 | *Plutella xylostella* | 0 |
| | 50 | *Diabrotica balteata* | 0 |
| | 50 | *Myzus persicae* (feeding/contact) | 50 |
| | 1.5 | *Myzus persicae* (systemic) | 0 |

Table B10 shows that compound A2 according to the invention exhibits a substantially better insecticidal action on *Spodoptera littoralis, Plutella xylostella, Diabrotica balteata* and *Myzus persicae* (feeding/contact and systemic activity) than the compound from the state of the art at the tested application rates. This enhanced effect was not to be expected on the basis of the structural similarity of these compounds.

Example B11: Activity Against *Frankliniella occidentalis* (Western Flower *Thrips*)

Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: A12.

The invention claimed is:
1. A compound of formula Z-1

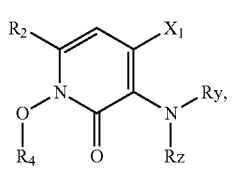

(Z-1)

$R_2$ is $CF_3$;
$R_4$ is unsubstituted alkyl;
$X_1$ is halogen or azido;
Ry is hydrogen or t-butyloxycarbonyl; and
Rz is $C_1$-$C_4$alkyl.

2. The compound of formula Z-1 according to claim 1, wherein $R_4$ is $C_1$-$C_6$alkyl.

3. The compound of formula Z-1 according to claim 2, wherein $R_4$ is $CH_3$.

4. The compound of formula Z-1 according to claim 3, wherein $X_1$ is azide.

5. The compound of formula Z-1 according to claim 4, wherein Rz is $CH_3$.

6. The compound of formula Z-1 according to claim 3, wherein $X_1$ is halogen.

7. The compound of formula Z-1 according to claim 6, wherein Rz is $CH_3$.

* * * * *